(12) United States Patent
Chen et al.

(10) Patent No.: US 7,115,556 B2
(45) Date of Patent: Oct. 3, 2006

(54) USE OF ANTI-PROLACTIN AGENTS TO TREAT PROLIFERATIVE CONDITIONS

(75) Inventors: Wen Y. Chen, Simpsonville, SC (US); Thomas E. Wagner, Greer, SC (US)

(73) Assignee: Greenville Hospital System, Greenville, SC (US)

( * ) Notice: Subject to any disclaimer, the term of this patent is extended or adjusted under 35 U.S.C. 154(b) by 658 days.

(21) Appl. No.: 10/140,293

(22) Filed: May 8, 2002

(65) Prior Publication Data
US 2003/0022833 A1 Jan. 30, 2003

Related U.S. Application Data

(63) Continuation of application No. 09/246,041, filed on Feb. 5, 1999, now abandoned.

(60) Provisional application No. 60/085,128, filed on May 13, 1998.

(51) Int. Cl.
*A61K 38/00* (2006.01)
(52) U.S. Cl. .................................. 514/2; 530/350
(58) Field of Classification Search .................... 514/2; 530/350
See application file for complete search history.

(56) References Cited

U.S. PATENT DOCUMENTS

| 5,350,863 | A | 9/1994 | Kuekenhoehner et al. |
| 5,506,107 | A | 4/1996 | Cunningham et al. |
| 5,681,809 | A | 10/1997 | Kopchick et al. |
| 6,429,186 | B1 | 8/2002 | Fuh et al. |

FOREIGN PATENT DOCUMENTS

| WO | WO 92/21029 A1 | 11/1992 |
| WO | WO 94/19004 A1 | 9/1994 |

OTHER PUBLICATIONS

Burgess et al., J of Cell Bio. 111:2129-2138, 1990.*
Bowie et al. Science, 247:1306-1310, 1990.*
Nicoll et al (Endocr Rev 1986 7:169-203).*
Freshney (Culture of Animal Cells, A Manual of Basic Technique, Alan R. Liss, Inc., 1983, New York, p. 4).*
Dermer (Bio/Technology, 1994, 12:320).*
(MSNBC News Services, "Mixed results on new cancer drug", Nov. 9, 2000).*
Gura (Science, 1997, 278:1041-1042).*
Jain (Sci. Am., 1994, 271:58-65).*
Curti (Crit. Rev. in Oncology/Hematology, 1993, 14:29-39).*
Chen et al (International Journal of Oncology, 2002, 20: 813-818).*
Straub et al (1993, J Biol Chem 268(29): 21997-20003).*
Kouklis et al (1993, J Cell Science, 106(pt 3): 919-28).*
Bontenbal, Feasibility, Endocrine and Anti-Tumour Effects of a Triple Endocrine Therapy with Tamoxifen, a Somatostatin Analogue and an Antiprolactin in Post-menopausal Metastatic Breast Cancer: a Randomized Study with Long-Term Follow-up, 1998, Br. J. Cancer 77:115-122.
Chen, Development of Recombinant Human Prolactin Receptor Antagonists by Molecular Mimicry of the Phosphorylated Hormone, 1998, Endocrinol 139:609-616.
Nevalainen, Prolactin and Prolactin Receptors are Expressed and Functioning in Human Prostate, 1997, J. Clin. Invest. 99: 618-627.
Nevalainen, Androgen-Dependent Expression of Prolactin in rat Prostate Epithelium in vivo and in organ Culture, 1997, FASEB J. 11: 1297-1307.
Ormandy, Coexpression and Cross-Regulation of the Prolactin Receptor and Sex Steroid Hormone Receptors in Breast Cancer, 1997, 3. Clin. Endocrinol. Metab. 82: 3692-369.
Reynolds, Expression of Prolactin and its Receptor in Human Breast Carcinoma, 1997, Endocrinology 138: 5555-5560.
Wennbo, Transgenic Mice Overexpressing the Prolactin Gene Develop Dramatic Enlargement of the Prostate Gland, 1997, Endocrinol. 138: 4410-4415.
Janssen, In Vitro Characterization of Prolactin-Induced Effects on Pro4feration in the Neoplastic LNCaP, DU145, and PC3 Models of the Human Prostate, 1996, Cancer 77: 144-149.
Goffm et al, Antagonistic Properties of Human Prolactin Analogs that Show Paradoxical Agonistic Activity in the Nb2 Bioassay, 1996, J. Biol. Chem. 271: 16573-16579.
Baumann, Editorial: Growth Hormone Binding Protein-Errant Receptor or Active Player?, 1995, Endocrinol. 136: 377-378.
Clevenger, Expression of Prolactin and Prolactin Receptor in Human Breast Carcinoma, 1995, Am. J. Pathol. 146:695-705.
Chen, Amino Acid Residues in the Third x-Helix of Growth Hormone Involved in Growth Promoting Activity, 1995, Mol. Endocrin, 9:292-302.
Fuh and Wells, Prolactin Receptor Antagonists that Inhibit the Growth of Breast Cancer Cell Lines, 1995, J. Biol. Chem. 270:13133-13137.
Ginsburg, Prolactin Synthesis and Secretion by Human Breast Cancer Cells, 1995, Cancer Res. 55:2591-2595.
Oliver, New Directions with Hormone Therapy in Prostate Cancer: Possible Benefit from Blocking Prolactin and Use of Hormone Treatment Intermittently in Combination with Immunotherapy, 1995, Eur. J. Cancer 31A:859-860.
Horseman, Editorial: Prolactin, Proliferation, and Protooncogenes, 1995, Endocrinol., 136: 5249-5251.
Bartke, Neuroendocrine and Reproductive Consequences of Overexpression of Growth Hormone in Transgenic Mice, 1994, Proc. Soc. Exp. Biol. Med. 206:345-359.
Baumann et al., Growth Hormone-Binding Proteins: State of the Art, 1994, J. Endocrinol. 141:1-6.
Chen, In Vitro and In Vivo Studies of Antagonistic Effects of Human Growth Hormone Analogs 1994, J. Biol. Chem. 269:15892-15897.
Costello, Effect of Prolactin on the Prostate ,1994, Prostate 24:162-166.

(Continued)

*Primary Examiner*—Jeffrey Siew
*Assistant Examiner*—Laura B. Goddard
(74) *Attorney, Agent, or Firm*—Foley & Lardner LLP

(57) ABSTRACT

The present invention relates to variant forms of human prolactin which act as antagonists at the prolactin receptor, and to the use of such variants in the treatment of human cancers and proliferative disorders, including both benign and malignant diseases of the breast and prostate.

15 Claims, 32 Drawing Sheets

OTHER PUBLICATIONS

Figure 1B:
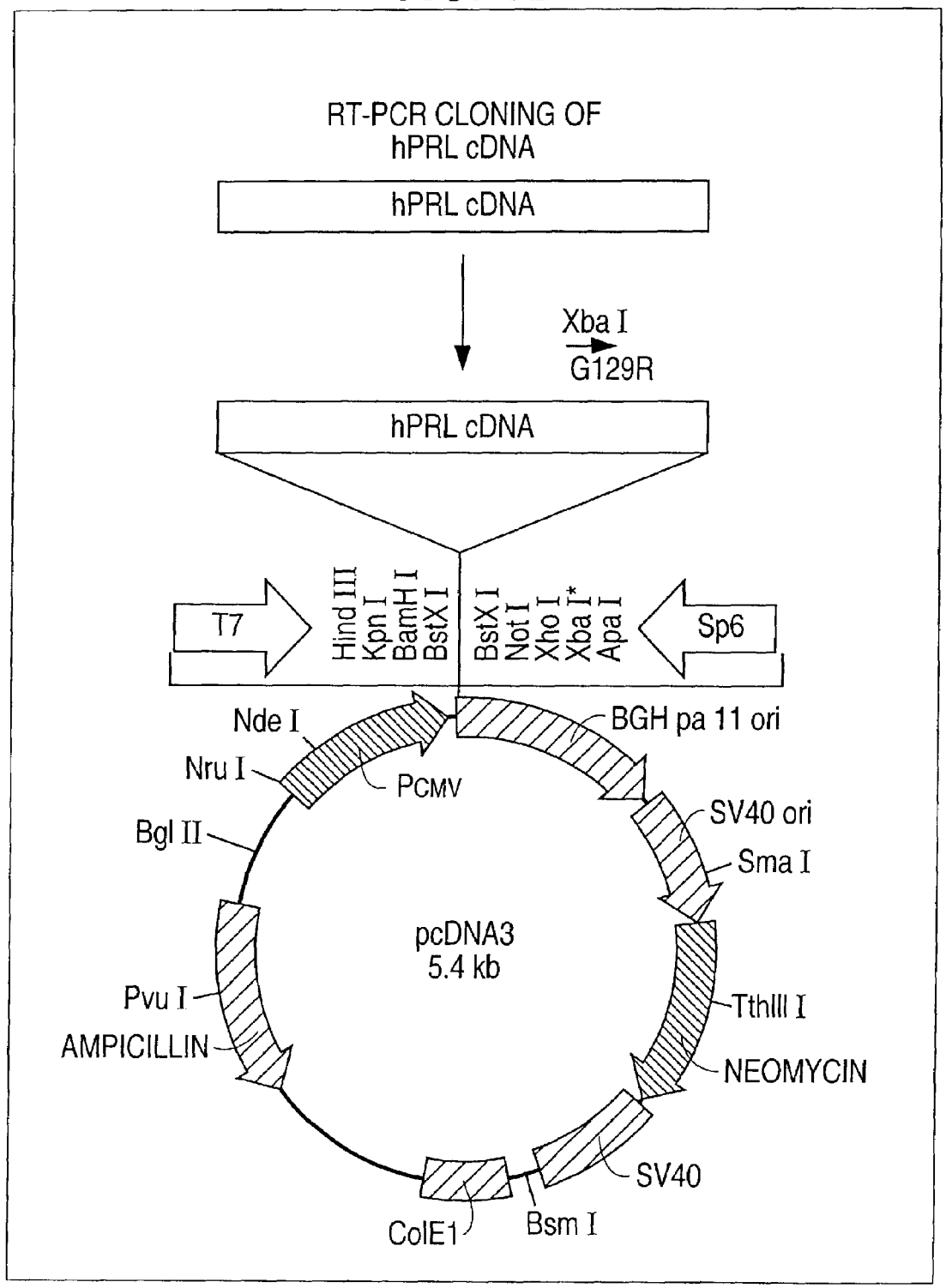

Goffin, Evidence for a Second Receptor Binding Site on Human Prolactin, 1994, J. Biol. Chem. 269:32598-32606.
Horseman, Transcriptional Regulation by the Helix Bundle Peptide Hormones: Growth Hormone, Prolactin, and Hematopoietic Cytokines, 1994, Endocrin. Rev. 15:627-649.
Fields, Detection of Prolactin Messenger RNA in Mammary and other Normal and Neoplastic Tissues by Polymerase Chain Reaction, 1993, Lab Invest. 68:354-360.
Fuh, Mechanism-Based Design of Prolactin Receptor Antagonists, 1993, J. Biol. Chem. 268:5376-5381.
Kelly, The Growth Hormone/Prolactin Receptor Family, 1993, Recent Prog. Horm. Res. 48:123-164.
Wang and Walker, Dephosphorylation of Standard Prolactin Produces a More Biologically Active Molecular: Evidence for Antagonism between Nonphosphoiylated and Phosphorylated Prolactin in the Stimulation of Nb2 Cell Proliferation, 1993, Endocrinol. 133:2156-2160.
Wells, The Molecular Basis for Growth Hormone-Receptor Interactions, 1993, Recent Prog. Hormone Res. 48:253-275.
Amit et al., Growth-Hormone-Binding Protein in Patients with Acromegaly, 1992, Hormone Res. 37:205-211.
Fuh, Rational Design of Potent Antagonists to the Human Growth Hormone Receptor, 1992, Science 256:1677-1680.
Krown, Prolactin Isoform 2 as an Autocrine Growth Factor for GH3 Cells, 1992, Endocrinol, 131:595-602.
Baumann, Growth Hormone Binding Proteins: Biochemical Characterization and Assays, 1991, Acta Endocrinol. 124 (Suppl. 2):21-26.
Chen, Glycine 119 of Bovine Growth Hormone is Critical for Growth-Promoting Activity, 1991, Mol. Endocrinol. 5:1845-1852.
Cunningham et al., Rational Design of Receptor-Specific Variants of Human Growth Hormone, 1991, Proc. Natl. Acad. Sci. USA 88:3407-3411.
Hochberg, The Effect of Human Growth Hormone Therapy on GH Binding Protein in GH-Deficient Children, 1991, Acta Endocrinol. 125:23-27.
Kelly, The Prolactin/Growth Hormone Receptor Family, 1991, Endocrin Rev. 12:235-25 1.
Chen, Expression of a Mutated Bovine Growth Hormone Gene Suppresses Growth of Transgenic Mice, 1990, Proc. Natl. Acad. Sci. USA 87:5061-5065.
Clevenger, Regulation of Interleukin2-Driven T-Lymphocyte Proliferation by Prolactin, 1990, Proc. Natl. Acad. Sci USA 87:6460-6464.
Cunningham, Engineering Human Prolactin to Bind to the Human Growth Hormone Receptor, 1990, Sci. 247:1461-1465.
Biswas, Role of Serum in the Prolactin Responsiveness of MCF-7 Human Breast Cancer Cells in Long-Term Tissue Culture, 1987, Cancer Res. 47:3509-35 14.
Shiu, Biological Actions of Prolactin in Human Breast Cancer, 1987, Recent Prog. Horm. Res. 43:277-303.
Manni, Promotion by Prolactin of the Growth of Human Breast Neoplasms Cultured in vitro in the Soft Agar Clonogenic Assay,1986, Cancer Res. 46:1669-1672.
Buckley, Prolactin is a Tumor Promoter in Rat Liver, 1985, Life Sci. 37:2569-2575.
Odoma, Evidence for the Association Between Blood Prolactin and Androgen Receptors in BPH, 1985,J.Uro l133:717-720.
Welsch, Host Factors Affecting the Growth of Carcinogen-Induced Rat Mammary Carconimas: A Review and Tribute to Charles Brenton Huggins, 1985, Cancer Res. 45:3415-3443.
Peyrat, Effect of Bromocriptin Treatment on Prolactin and Steroid Receptor Levels in Human Breast Cancer, 1984, Eur J. Cancer Clin. Oncol. 20:1363-1367.
Leake et al., Characterization of the Prolactin Receptor in Human Prostate, 1983, J. Endocrinol. 99:321-328.
Malarkey, Physiological Concentrations of Prolactin can Promote the Growth of Human Breast Tumor Cells in Culture, 1983, J. Clin. Endocrinol Metab. 56:673-677.
Saroff, Measurements of Prolactin and Androgens in Patients with Prostatic Diseases, 1980, Oncology 37:46-52.
Shiu and Friesen Mechanism of Action of Prolactin in the Control of Mammary Gland Function, 1980, Annu. Rev. Physiol. 42:83-96.
Hammond et al., Serum FSH, LH and Prolactin in Normal Males and Patients with Prostatic Diseases, 1977, Clin. Endocrinol. 7:129-135.
Harper, Plasma Steroid and Protein Hormone Concentrations in Patients with Prostatic Carcinoma, Before and During Oestrogen Therapy, 1976, Acta Endocrinol. 81:409-426.
Aragona and Friesan, Specific Prolactin Binding Sites in the Prostate and Testis of Rats, 1975, Endocrinol. 97:677-684.
Vekemans and Robyn, Influence of Age on Serum Prolactin Levels in Women and Men, 1975, Br. Med. J. 4:738-739.
Brendler, Adrenalectomy and Hypophysectomy for Prostatic Cancer, 1973, Urology 2:99-102.
Heuson, Clinical Trial of2-Br-a'-Ergocryptine (CB154) In Advanced Breast Cancer, 1972, Eur J. Cancer 8:155-156.

* cited by examiner

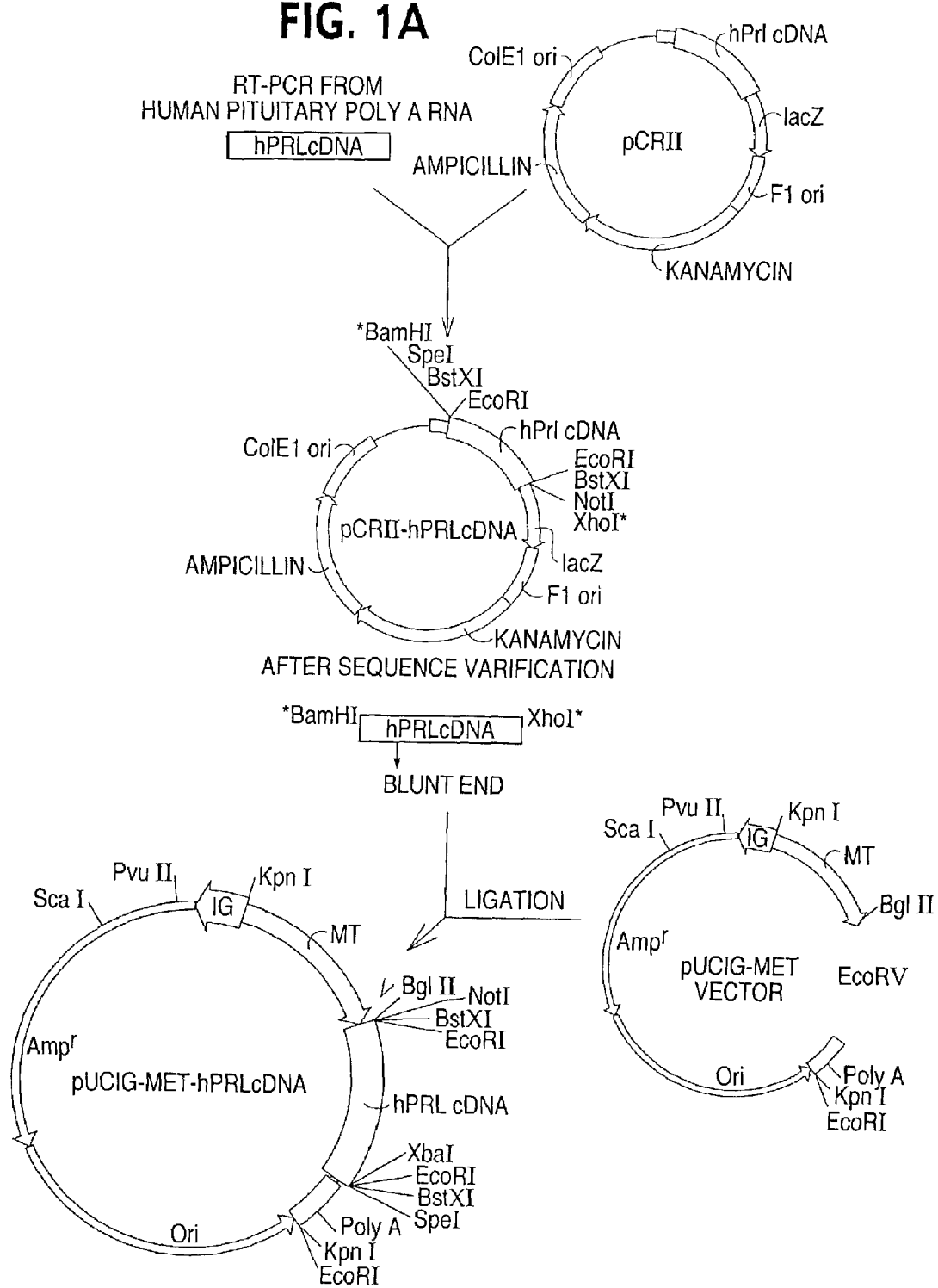

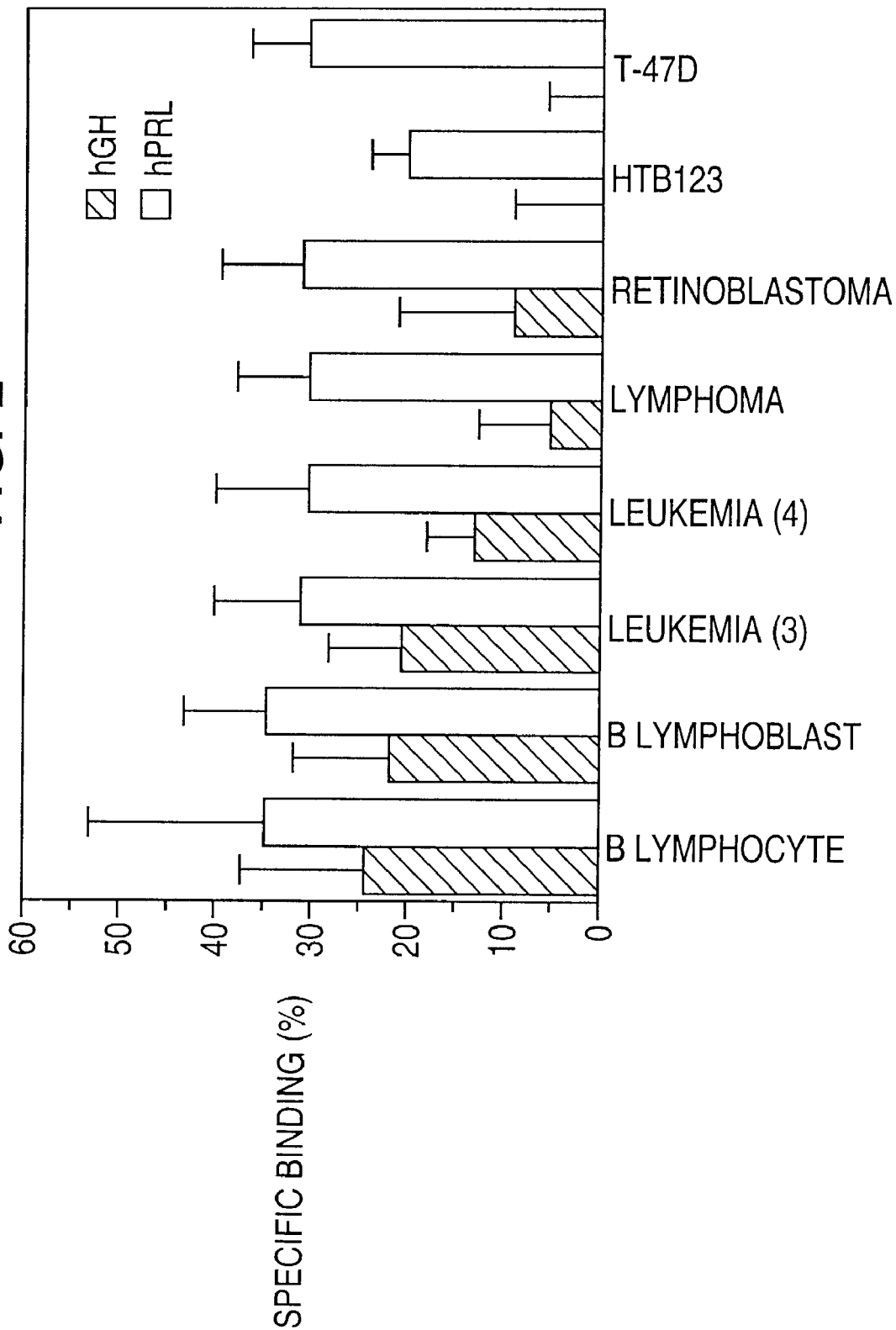

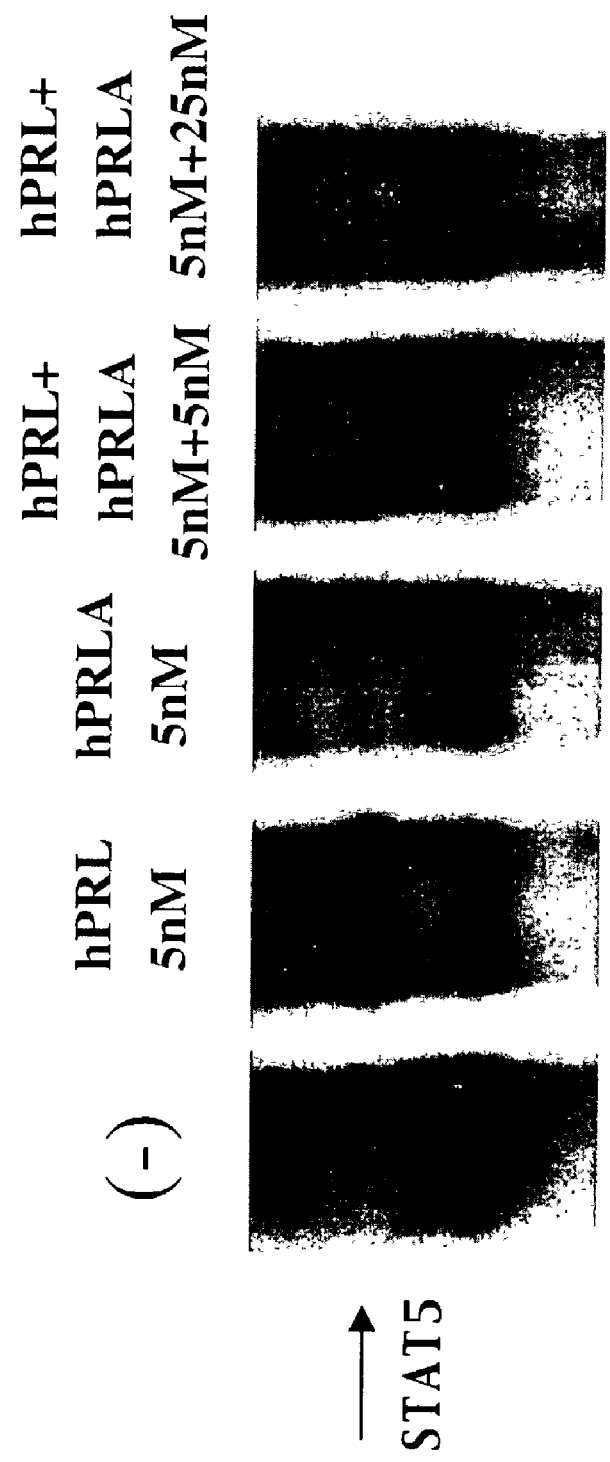

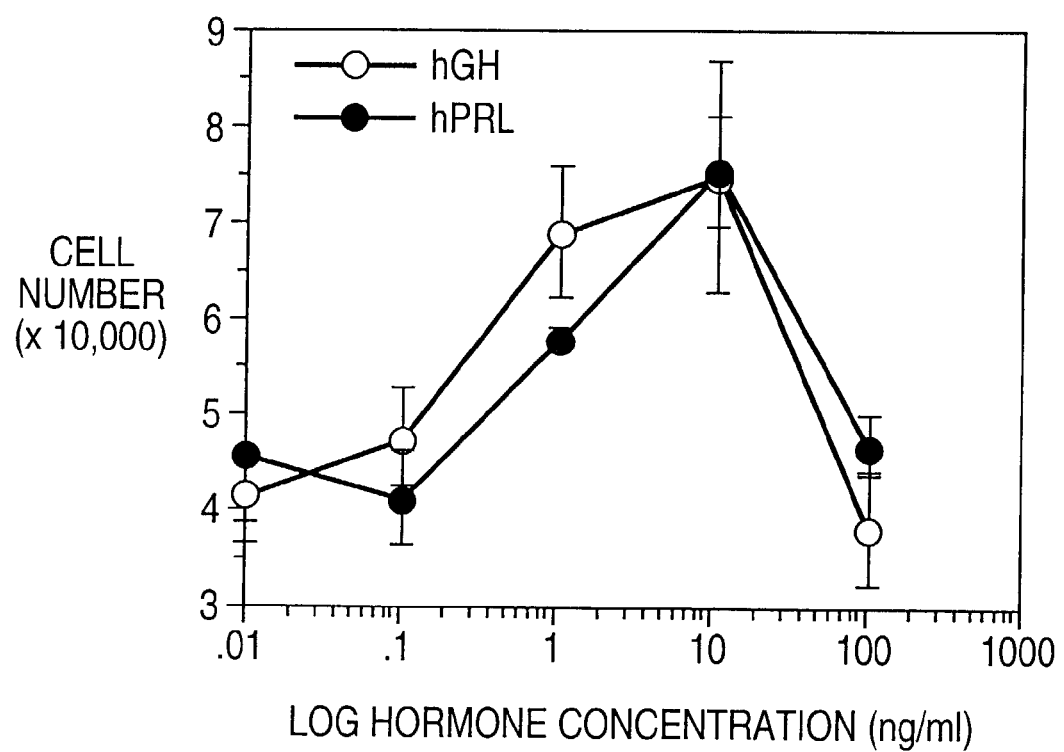

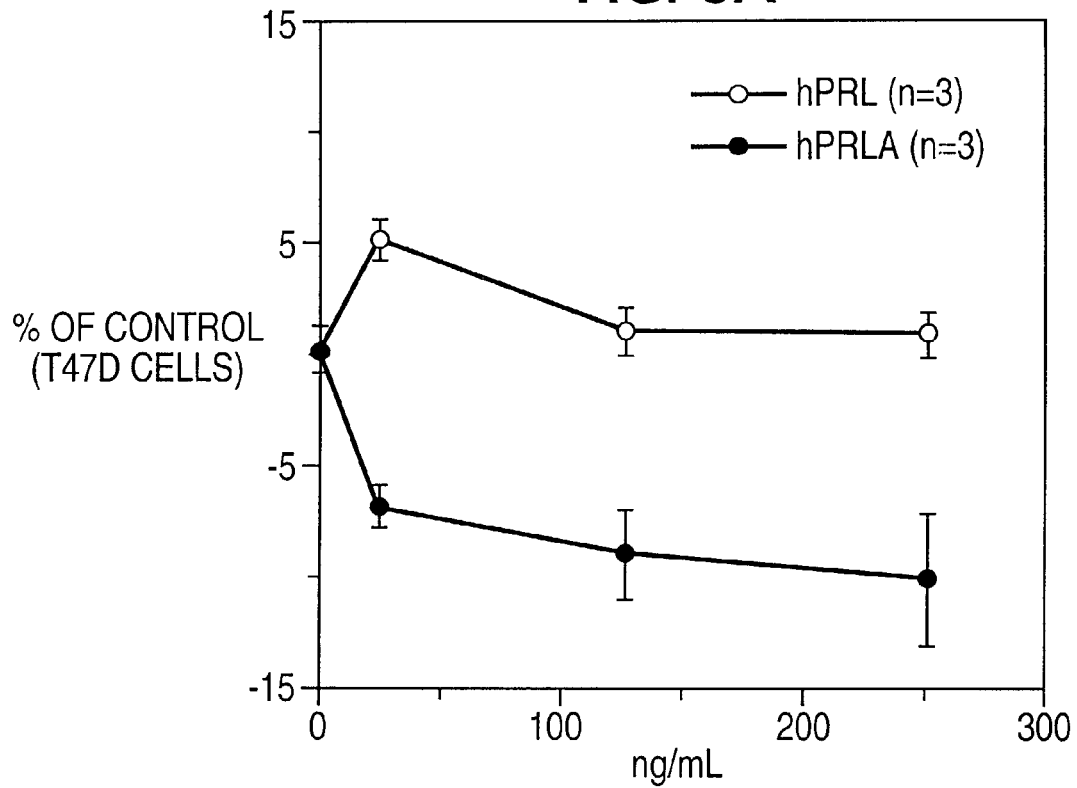
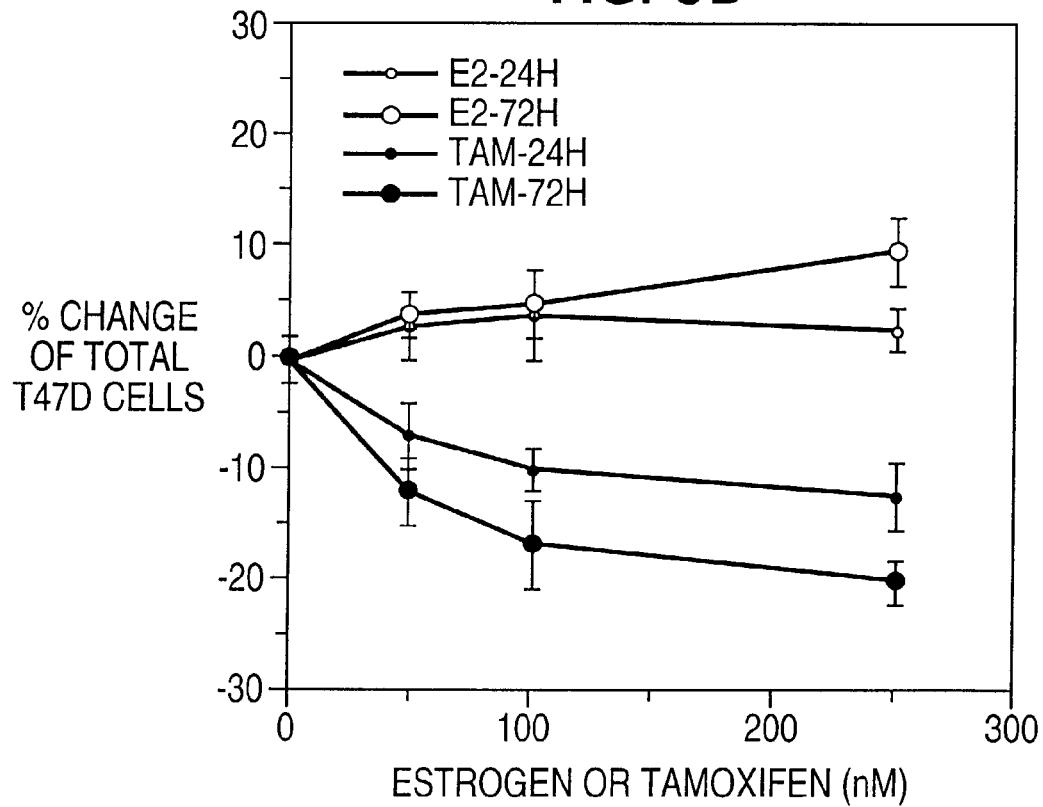

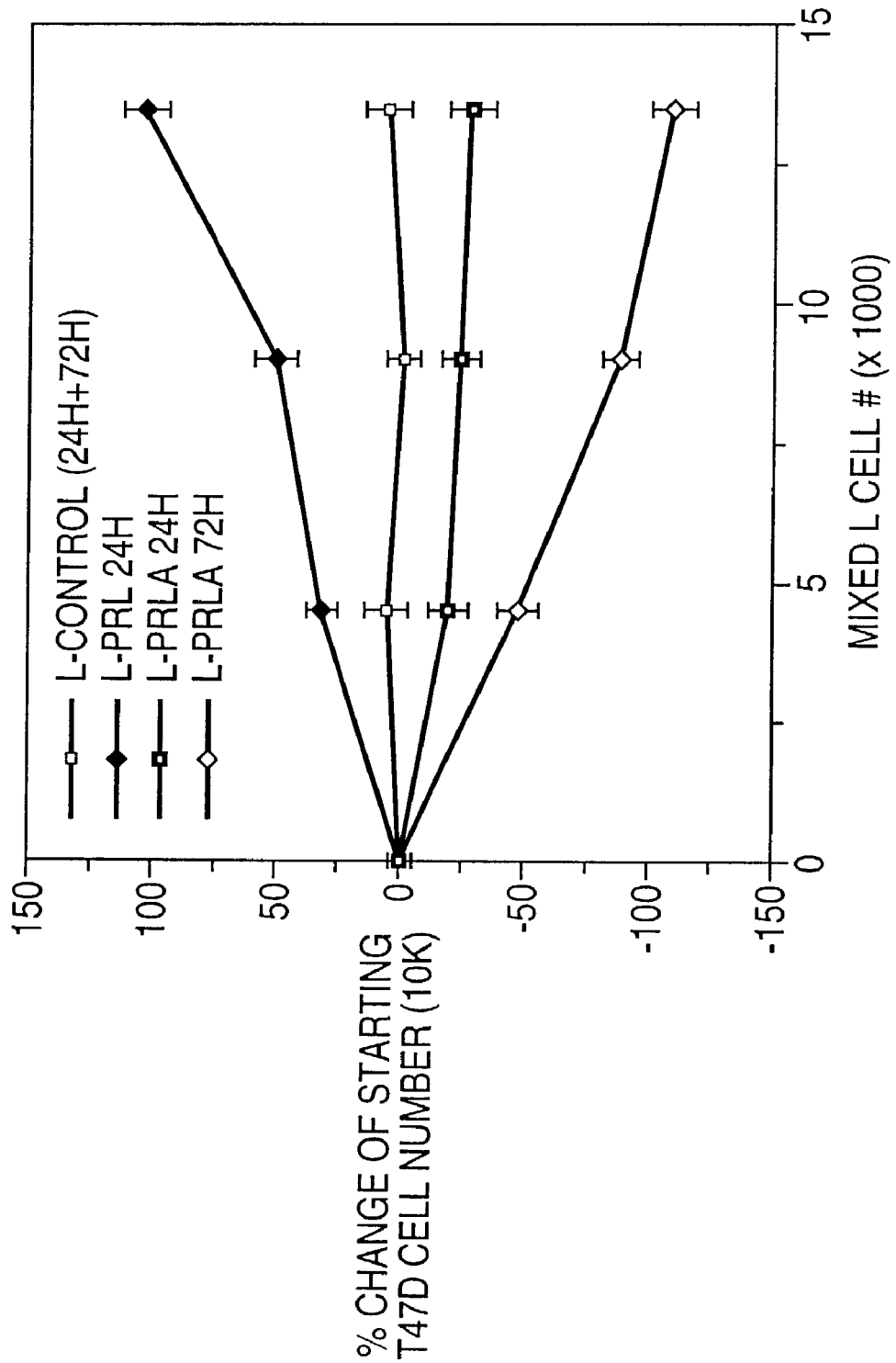

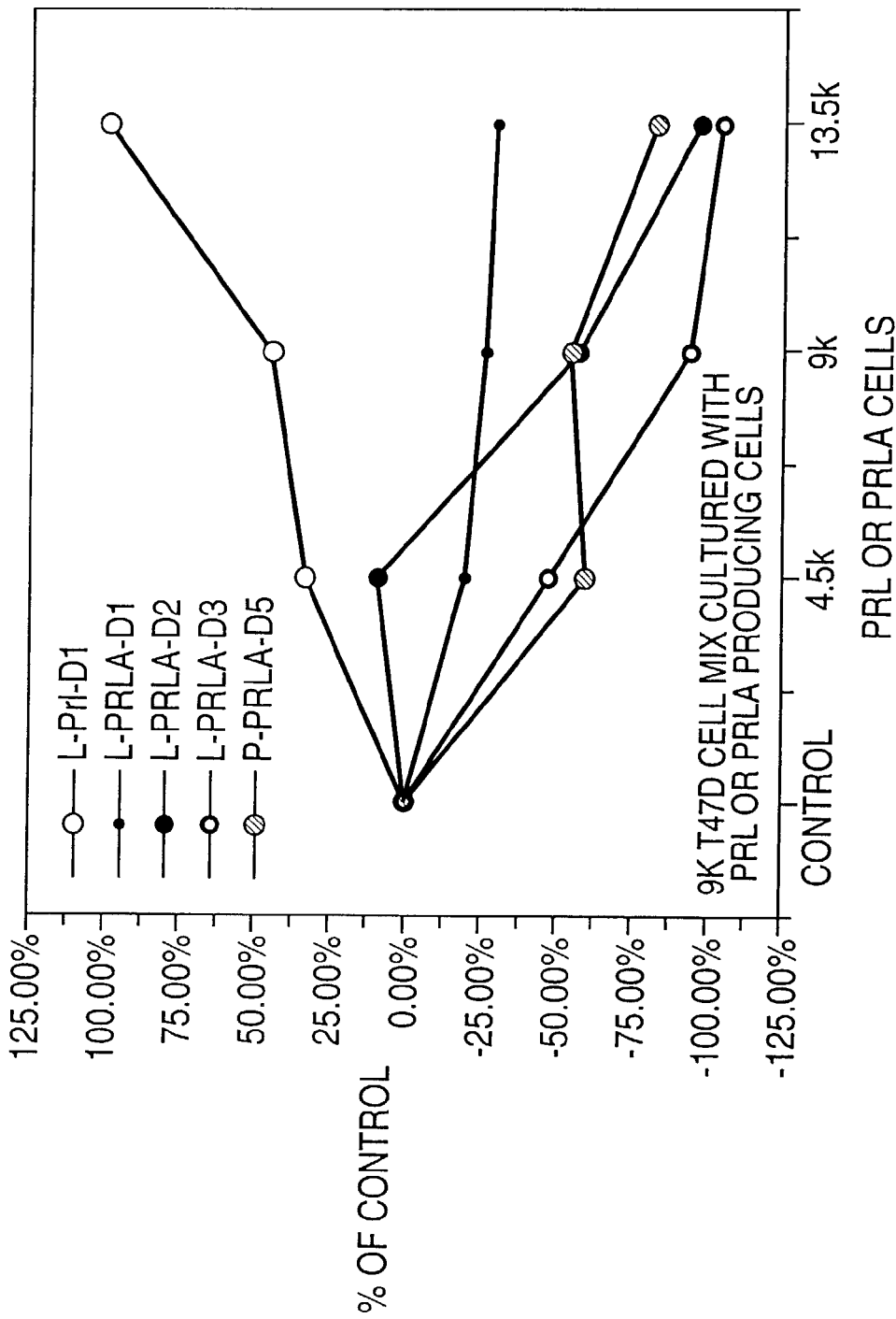

MIXED CULTURE-T47D VS LCELLS/PRLA CELLS-DAY 3

MIXED CULTURE-MCF-7 VS LCELLS/PRLA CELLS-DAY 3

FIG. 10A

FIG. 10B

A. CONTROL

B. hPRL

B. hPRL-G129R

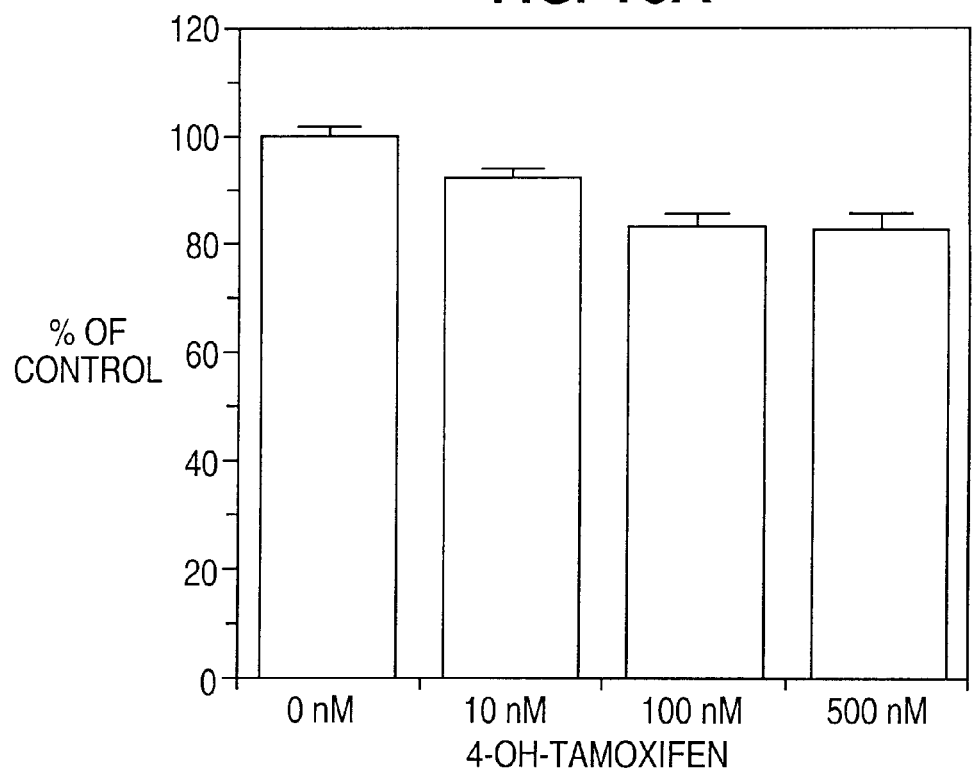
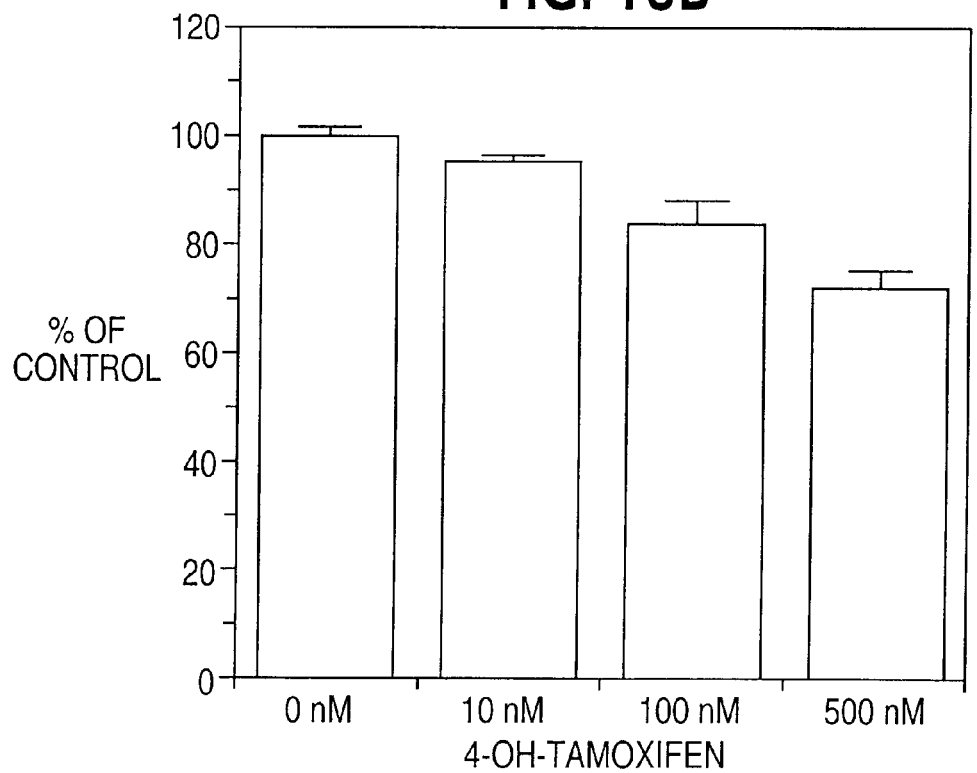

A. T47D Control

B. T47D 50ng G129R

C. T47D 125ng G129R

D. T47D 50ng G129R-24h

E. T47D 50ng G129R-48h

B. BT-474 G129R 250ng

D. MCF-7 G129R 250ng

A. BT-474 Control

C. MCF-7 Control

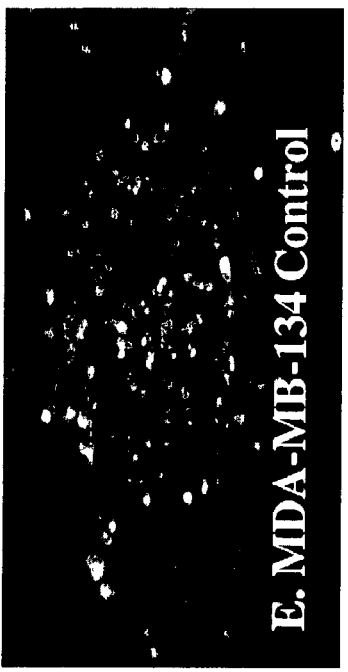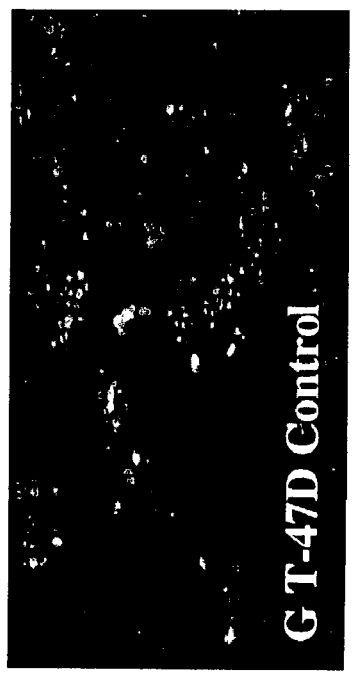

MCF-7-1uM 4-OHT

T-47D -Control

T-47D-1uM 4-OHT

FIG. 25
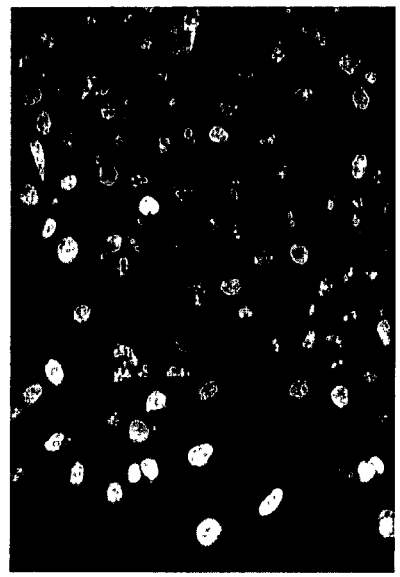
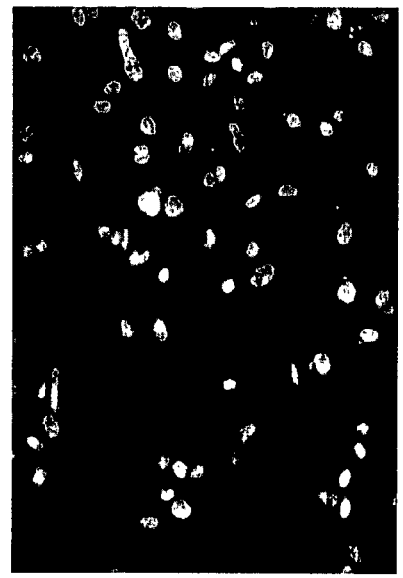
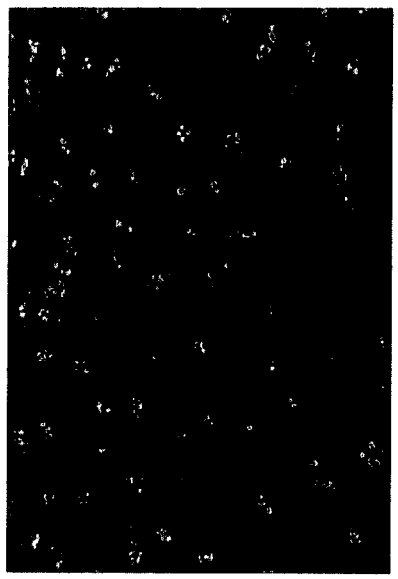
hPRL-G129R Treated (500ng/ml)
Untreated Control
PC-3
LNcap

USE OF ANTI-PROLACTIN AGENTS TO TREAT PROLIFERATIVE CONDITIONS

CROSS REFERENCE TO RELATED APPLICATIONS

This application is a continuation of U.S. application Ser. No. 09/246,041, filed Feb. 5, 1999, now abandoned, which claims benefit of U.S. Provisional Application Ser. No. 60/085,128, filed May 13, 1998.

1. INTRODUCTION

The present invention relates to methods and compositions for inhibiting the cell proliferation-promoting effects of prolactin on its receptor. The methods and compositions of the invention may be used in the treatment of benign as well as malignant conditions which involve unwanted cell proliferation.

2. BACKGROUND OF THE INVENTION

Prolactin ("PRL") is a 23-kDa neuroendocrine hormone which is structurally related to growth hormone and, to a lesser degree, to members of the interleukin family (Reynolds et al., 1997, Endocrinol. 138:5555–5560, Cunningham et al., 1990, Science 247:1461–1465; Wells et al., 1993, Recent Prog. Horm. Res. 48:253–275). Acting via the prolactin receptor, it is required for the proliferation and terminal differentiation of breast tissue (Mani et al., 1986, Cancer Res. 46:1669–1672; Malarkey et al., 1983, J. Clin. Endocrinol. Metab. 56:673–677; Biswas and Vonderhaar, 1987, Cancer Res. 47:3509–3514), promoting the growth and differentiation of the ductal epithelium, proliferation and differentiation of lobular units, and initiation and maintenance of lactation (Kelly et al., 1993, Recent Prog. Horm. Res. 48:123–164; Shiu et al., 1987, recent Pro. Horm. Res. 43:277–303). A diversity of other effects have been attributed to PRL, including roles in reproduction and the immune response (Wennbo et al., 1997, Endocrinol. 138:4410–4415; Nicoll, 1974, in *Handbook of Physiology*, Knobil and Sawyer, eds., American Physiological Society, Washington, D.C.; Shiu and Friesen, 1980, Annu. Rev. Physiol. 42:83–96).

The prolactin receptor ("PRLR") is a member of the cytokine receptor superfamily and binds a group of hormones, including not only PRL but also placental lactogens and primate growth hormone ("GH"), to produce a mitogenic effect (Ormandy et al., 1997, J. Clin. Endocrinol. Metab. 82:3692–3699; Horseman, 1995, Endocrinol. 136:5249–5251; Clevenger et al., 1990, Proc. Natl. Acad. Sci. U.S.A. 87:6460–6464; Buckley et al., 1985, Life Sci. 37:2569–2575; Costello et al., 1994, Prostate 24:162–166). PRLR is homologous to the receptor for GH ("GHR", also referred to as the somatogen receptor) and both belong to the cytokine receptor superfamily (Kelly et al., 1991, Endocrin. Rev. 12:235–251; Kelly et al., 1993, Recent. Prog. Horm. Res. 48:123–164; Horseman and Yu-Lee, 1994, Endocrin. Rev. 15:627–649).

An association between PRL activity and breast cancer has been proposed (Ormandy et al., 1997, J. Clin. Endocrinol. Metab. 82:3692–3699). Elevated PRL levels have been found to accelerate the growth of mammary tumors induced by 7,12 dimethylbenz($\alpha$)antracene in rats, whereas PRL ablation was observed to have an inhibitory effect (Welsch, 1985, Cancer Res. 45:3415–3443). Mammary tumor growth was increased in transgenic mice overexpressing human GH, which binds to the rodent PRLR (Bartke et al., 1994, Proc. Soc. Exp. Biol. Med. 206:345–359). It has been found that the receptors for sex steroids and PRL are co-expressed and cross-regulated, which might explain the synergistic actions of estrogen, progesterone, and PRL in tumor growth control (Ormandy et al., 1997, J. Clin. Endocrinol. Metab. 82:3692–3699).

Nevertheless, to date, therapies which reduce PRL levels, such as hypophysectomy and bromocriptine administration (both directed toward decreasing or eliminating production of PRL by the pituitary gland), have not been successful in the treatment of breast cancer (Peyrat et al., 1984, Eur. J. Cancer Clin. Oncol. 20:1363–1367; Heuson et al., 1972, Eur. J. Cancer 8:155–156). It has been proposed that PRL may nevertheless have a role in breast cancer if an autocrine/paracrine growth regulatory loop exists (that is to say, that the pituitary is only one of several sources for prolactin; see Clevenger et al., 1995, Am. J. Pathol. 146:695–705, Fields et al., 1993, Lab. Invest. 68:354–360; Ginsburg and Vonderhaar, 1995, Cancer Res. 55:2591–2595; Fuh and Wells, 1995, J. Biol. Chem. 270:13133–13137). In this regard, when RNA levels of PRL and PRLR were performed using reverse transcriptase/PCR techniques, it was found that PRL and PRLR were widely expressed in breast cancers (>95 percent) and normal breast tissues (>93 percent), suggesting that interventions in the PRL/PRLR receptor may be useful in the treatment of breast cancer (Reynolds et al., Endocrinol. 138:5555–5560). Indeed, it has recently been reported that a combined regimen combining an anti-estrogen (tamoxifen), a GH analog (octreotide), and a potent anti-prolactin (CV 205-502, a dopamine agonist which inhibits prolactin secretion by the pituitary) had better clinical results in metastatic breast cancer patients compared to tamoxifen therapy alone (Botenbal et al., 1998, Br. J. Cancer 77:115–122).

An association between PRL expression and prostate disease has also been proposed (Wennbo et al., 1997, Endocrinol. 138:4410–4415). PRL receptors are found in prostate tissue (Aragona and Friesen, 1975, Endocrinol. 97:677–684; Leake et al., 1983, J. Endocrinol. 99:321–328). PRL levels have been observed to increase with age (Hammond et al., 1977, Clin. Endocrinol. 7:129–135; Vekemans and Robyn, 1975, Br. Med. J. 4:738–739) coincident with the development of prostate hyperplasia and PRL has been found to have trophic and differentiating effects on prostate tissue (Costello and Franklin, 1994, Prostate 24:162–166). Transgenic mice overexpressing the PRL gene developed dramatic enlargement of the prostate gland (Wennbo et al., 1997, Endocrinol. 138:4410–4415). Nonetheless, the role for PRL in prostate disease remains unclear (Wennbo et al., 1997, Endocrinol. 138:4410–4415). PRL levels in patients having prostate hyperplasia have been reported to be either increased (Odoma et al., 1985, J. Urol. 133:717–720; Saroff et al., 1980, Oncology 37:46–52), increased only in patients with prostate cancer or unchanged (Harper et al., 1976, Acta Endocrinol. (Copenh) 81:409–426). Janssen et al. reported that proliferation of androgen-insensitive human prostate cell lines can be significantly modulated by PRL (1996, Cancer 77:144–149). To explain these discrepancies, it has been proposed that local synthesis of PRL in the prostate (Nevalainen et al., 1997, J. Clin. Invest. 99:618–627) may be an important factor. Androgen-dependent expression of PRL in rat prostate epithelium has been observed, supporting the concept of an autocrine/paracrine loop of prolactin action in the prostate, where it could mediate androgen-associated effects (Nevalainen et al., 1997, FASEB J. 11(14):1297–1307). Further, clinical data appears promising: hypophysectomy has been found to have an additive therapeutic effect when combined with castration and adrenalectomy in prostate cancer patients (Brendler, 1973, Urology 2:99–102), and Rana et al. report that a combined maximal suppression of androgens and prolactin resulted in a significantly improved clinical response over conventional treatments in patients suffering from advanced prostate cancer (Habib et al., 1995, Eur. J. Cancer 31 A:859–860).

In view of the biological relevance of the PRL molecule and its receptor, a number of investigators have evaluated the activity of PRL variants which bear structural differences relative to the native unmodified molecule. It has been reported that naturally phosphorylated rat PRL antagonizes the growth-promoting effects of unmodified PRL in an assay which measures proliferation of rat Nb2 T lymphoma cells and in the autocrine regulation of $GH_3$ cell proliferation (Wang and Walker, 1993, Endocrinol. 133:2156–2160; Krown et al., 1992, Endocrinol. 122:223–229). Further, molecular mimics of phosphorylated PRL having a bulky negatively charged amino acid (namely glutamate or aspartate) substituted for the serine at position 179 antagonized the growth-promoting effects of PRL (Chen et al., 1998, Endocrinol. 139: 609–616).

Other strategies for PRL variant design have been directed at disruption of the interaction between PRL and its receptor. To this end, researchers have drawn analogies between the PRLR and the GHR, for which the structure/function relationships are better understood.

Certain features of the GHR were elucidated by studying the basis for the full GH antagonist activity of the variant of human GH ("hGH") having a substitution of the glycine at position 120 with an arginine residue (Chen et al., 1990, Proc. Natl. Acad. Sci. U.S.A. 87:5061–5065; Chen et al., 1991, Mol. Endocrinol. 5:1845–1852; Chen et al., 1994, J. Biol. Chem. 269:15892–15897; Chen et al., 1995, Mol. Endocrinol. 9:1–7; U.S. Pat. No. 5,350,836 by Kopchick and Chen; U.S. Pat. No. 5,681,809 by Kopchick and Chen). It was deduced that hGH forms a complex with a dimeric form of the hGHR. Fuh and colleagues proposed a sequential dimerization model whereby GH would first bind to one receptor via a first binding site (delimited by portions of helix 1, helix 4 and loop 1 of GH) to form an inactive intermediate 1:1 complex, and then the receptor-bound hGH would interact with a second receptor through binding site 2 (involving the helix 3 glycine of GH mutated in the G120R variant) to produce the active 1:2 hormone/receptor complex (Fuh et al., 1992, Science 256:1677–1680; Fuh et al., 1993, J. Biol. Chem. 268:5376–5381, Goffin et al., 1994, J. Biol. Chem. 269:32598–32606). When the helix 3 glycine at position 120 of GH is substituted with an arginine residue, the second binding site is sterically hindered and the GH can no longer induce receptor dimerization.

Although less is known about the structure of the PRLR, it has been suggested that it, too, is activated by hormone-mediated sequential dimerization (Cunningham et al., 1991, Proc. Natl. Acad. Sci. U.S.A. 88:3407–3411; Fuh et al., 1992, Science 256: 1677–1680; Fuh et al., 1993, J. Biol. Chem. 268:5376–5381). Variants of human PRL ("hPRL") were produced containing mutations in the region believed to correspond to the helix 3/helix 1 interface of GH, including mutations of the alanine at position 22, the leucine at position 25, the serine at position 26 and the glycine at position 129 of PRL to tryptophan and/or arginine (specifically, to create A22W, L25R, L25W, S26R, S26W and G129R; Goffin et al., 1994, J. Biol. Chem. 269:32598–32606). It was reported in that paper that the point mutations at A22, S26 and G129 drastically decreased the mitogenic potency of the variant (as compared to native PRL) by 2–3 orders of magnitude (as tested in the Nb2 proliferation assay), although the G129R variant (positionally analogous to G120R of GH) was reported to act as a weak agonist rather than as an antagonist. It was subsequently reported that when tested in an assay for PRLR activity in which cells, co-transfected with nucleic acid encoding the hPRLk and a reporter gene under the control of PRL-responsive DNA sequences, were exposed to the G129R hPRL variant, an antagonist effect was observed (Goffin et al., 1996, J. Biol. Chem. 271:16573–16579).

Naturally occurring antagonists of GH action may exist. A cell-free truncated form of the GHR (termed "GH-BP") has been identified in man and certain animals (Baumann, 1991, Acta Endocrinol. 124(suppl 2):21–26; Baumann et al., 1994, J. Endocrinol. 141:1–6; Baumann, 1995, Endocrinol. 136:377–378). The human form of GH-BP encompasses the extracellular domain of the receptor, and could be the result of proteolytic cleavage of the native receptor or alternative RNA splicing. It has been suggested that GH-BP acts to inhibit binding of GH to its receptors (Baumann, 1991, Acta Endocrinol. 124(suppl 2):21–26; Baumann et al., 1994, J. Endocrinol. 141:1–6). Supportive of this hypothesis is the observation that GH-BP levels in patients suffering from acromegaly (due to overexpression of GH) have an inverse correlation with serum GH levels (that is to say, the less GH-BP, the more serum GH present; Amit et al., 1992, Hormone Res. 37:205–211). Lower levels of GH-BP may render the acromegalic serum GH relatively more active in the GH receptor assay and therefore contribute negatively to the disease (Hochberg et al., 1994, Acta Endocrinol. 125: 23–27). Soluble forms of other receptors in the cytokine receptor superfamily have also been observed (Baumann, 1995, Endocrinol. 136:377–378). Nevertheless, there has not been, prior to the present invention, any evidence suggesting the existence of a naturally occurring cell-free from of the PRLR.

3. SUMMARY OF THE INVENTION

The present invention relates to methods and compositions for inhibiting the cell proliferation-promoting effects of prolactin on its receptor.

In a first set of embodiments, the present invention provides for a prolactin variant which acts as an antagonist at the prolactin receptor, and for the use of such a prolactin variant in inhibiting the proliferation of a cell which expresses a prolactin receptor. The invention is based in the observation that a prolactin variant is capable of inhibiting cell proliferation in a dose dependent manner. Further, it was observed that the prolactin variant was able to induce apoptosis in cancer cells. In preferred embodiments, the prolactin variant is a mutated form of human prolactin in which the glycine amino acid at position 129 is substituted with another amino acid. In specific nonlimiting embodiments, the glycine at position 129 of human prolactin is substituted with arginine.

In a second set of embodiments, the present invention provides for a truncated form of the prolactin receptor which is capable of binding to prolactin and thereby decreases the availability of prolactin to bind to its receptor. The prolactin variants and truncated prolactin receptors of the invention may be used in methods of inhibiting the proliferation of cells expressing prolactin receptors.

The present invention further provides methods for inducing apoptosis in cells expressing the prolactin receptor. The invention is based on the observation that a prolactin variant is capable of inducing cellular apoptosis in human breast cancer cells.

In yet another embodiment of the invention, the present invention provides methods of inhibiting the proliferation of cells expressing prolactin receptor comprising the use of a prolactin variant in conjunction with an anti-estrogen. Such anti-estrogens include, but are not limited to, tamoxifen, raloxifene, or ICI 164384 (Imperial Chemical Industries). The method is based on the observation that the administration of a prolactin variant together with an anti-estrogen induces a synergistic inhibitory effect on cell proliferation. In addition, a prolactin variant may be used in conjunction with an anti-androgen. Such anti-androgens include, but are not limited to, flutamide, anandron or cyproterone acetate to induce a synergistic inhibition of cellular proliferation (see, Smith, D. C., 1997, Semin. Urol. Oncol. 15:3–12 for review of anti-androgen therapy; Gomella, I. M., 1997, 3:16–24; Suciu, S., 1993, Cancer 15:3841–6),.

Accordingly, such methods may be used in the treatment of clinical disorders in humans and non-human animals which involve unwanted cell proliferation. In specific non-limiting embodiments, the present invention may be used in the treatment of breast and prostate cancers in humans.

4. BRIEF DESCRIPTION OF THE DRAWINGS

FIG. 1A. Schematic representation of the cloning and construction of the expression plasmid pUCIG-MT-hPRL-cDNA.

FIG. 1B. Plasmid map and general strategy of PCR-directed mutagenesis. pcDNA3, the parental vector, contains human immediate-early cytomegalovirus (CMV) transcriptional regulatory sequences and a polyadenylation signal and transcription termination sequence from bovine GH gene (BGH pA). hPRL cDNA was cloned using RT-PCR from human pituitary mRNA and inserted into BstX1 sites. Mutation was generated by designing PCR primers at Xba I sites.

FIG. 2. Data from competitive radioreceptor binding experiments for hGH and hPRL using various human cancer cell lines (listed along the x-axis). HTB123 and T47D are human breast cancer cell lines. The y axis represents the percent specific binding. Each point represents the mean of three experiments which were each carried out in duplicate.

FIG. 3. Western blot analysis showing phosphorylation of STAT proteins (band at arrow) in T47D human breast cancer cells under various conditions. Reading from left to right, lane 1 depicts a control culture, lane 2 depicts a culture receiving 5 nM of HPRL, lane 3 depicts a culture receiving 5 nM of hPRLA, lane 4 depicts the competitive effects when the culture is exposed to 5 nM of hPRL and 5 nM of hPRLA, and lane 5 depicts the competitive effects when the culture is exposed to 5 nM hPRL and 25 nM hPRLA.

FIG. 4. Effects of growth hormone and prolactin on breast cancer cell proliferation. The x-axis represents the concentration of hGH or HPRL present in the culture media of T-47D human breast cancer cells. The y axis represents the total cell number at the end of the incubation period. Points are the average (+SD) of three experiments, each of which was carried out in duplicate.

FIGS. 5A–B. (A) Effects of various concentrations of hPRL or the G129R prolactin variant hPRLA on the proliferation of T47D human breast cancer cells in culture. (B) Effects of various concentrations of estrogen (E2) and tamoxifen (Tam) on the proliferation of T47D cells over a period of 24 or 72 hours.

Figure 6:
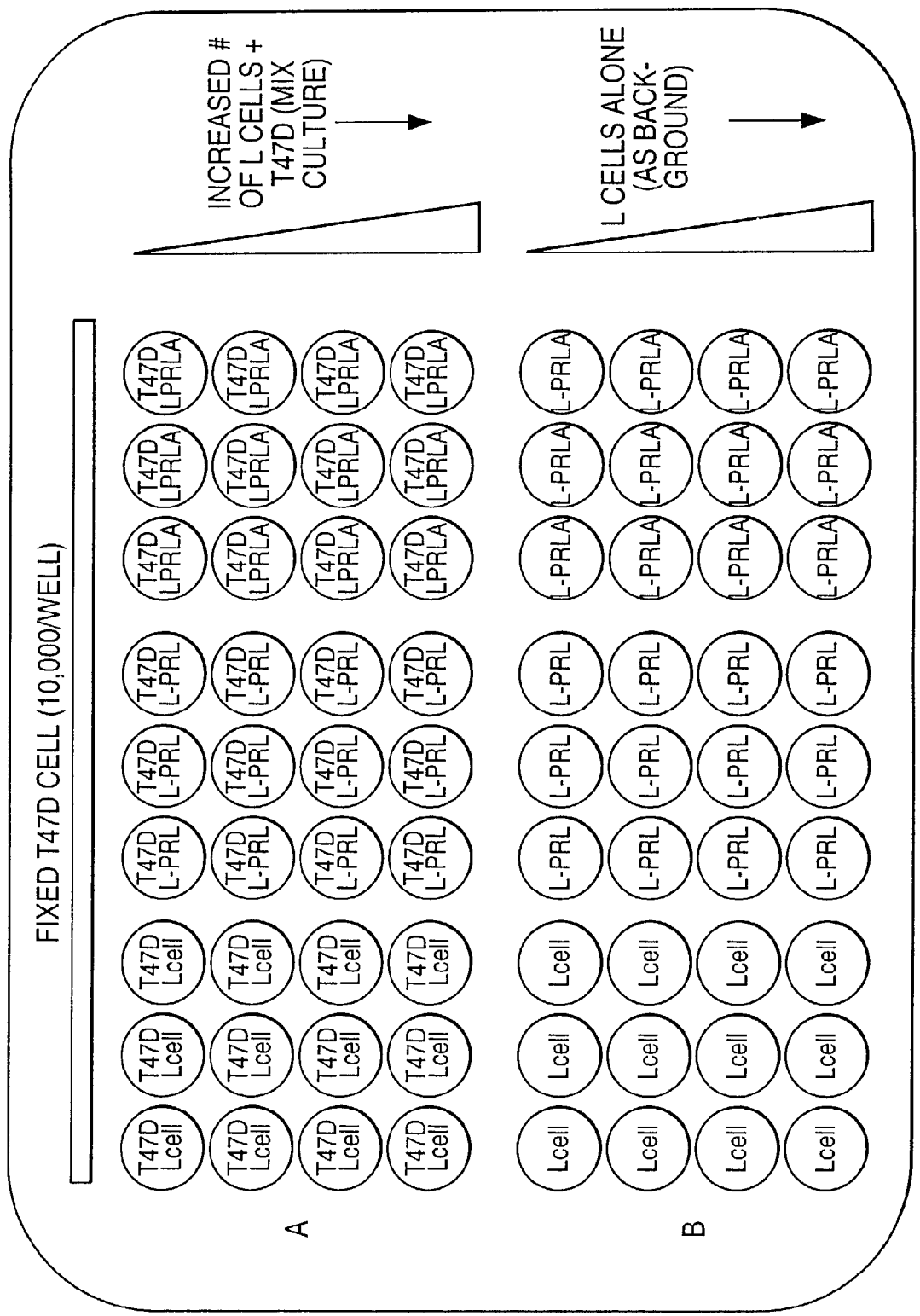

FIG. 6. Diagram of a mixed cell culture assay for evaluating the effects of recombinant hPRL and the G129R prolactin variant hPRLA on T47D cell proliferation.

FIG. 7. Effects of recombinantly expressed hPRL (L-PRL) and the G129R prolactin variant hPRLA (L-PRLA) on T47D breast cancer cell proliferation in a mixed cell culture assay after 24 and 72 hours.

FIG. 8. Effects of recombinantly expressed hPRL (L-PRL) and the G129R prolactin variant (L-PRLA) on T47D breast cancer cell proliferation in a mixed cell culture assay after one (D1), two (D2), three (D3) or five (D5) days.

Figure 9A:
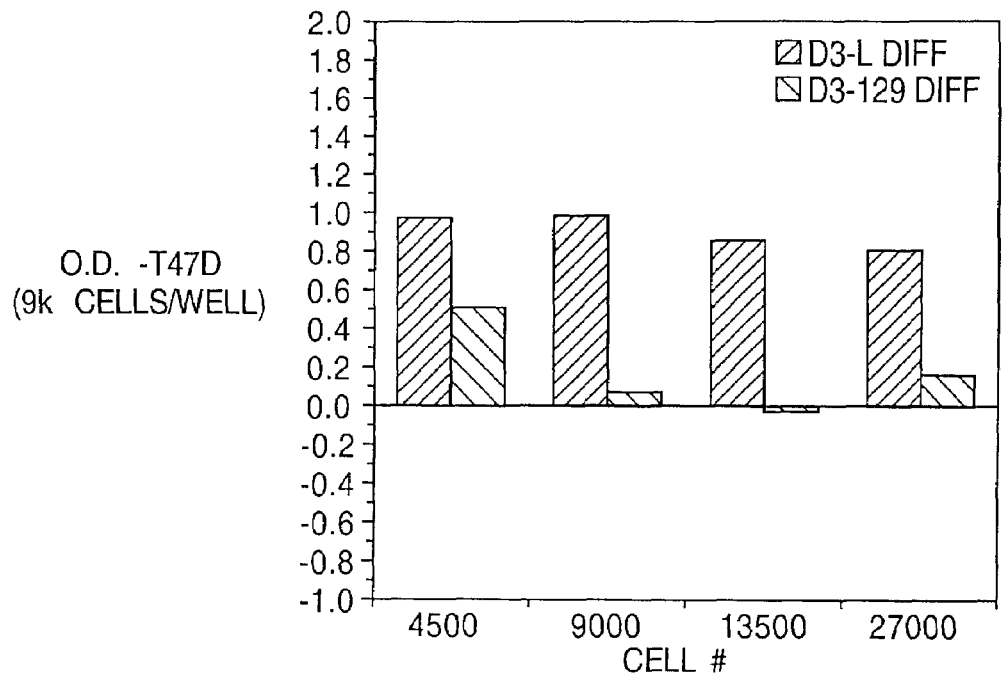
Figure 9B:
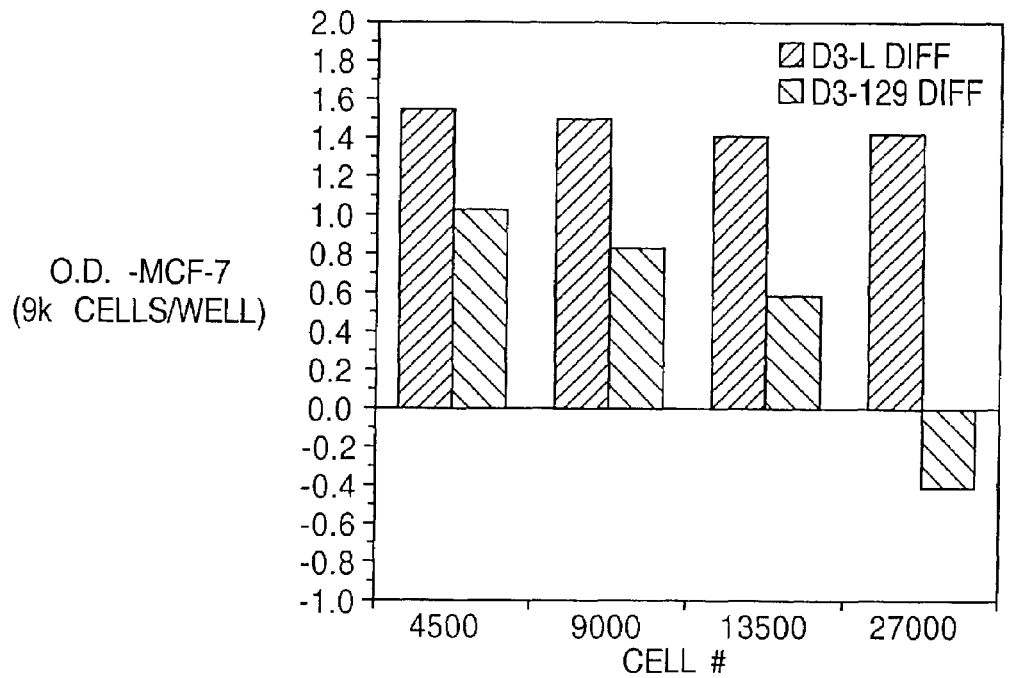

FIGS. 9A–B. Proliferation of either (A) T47D human breast cancer cells or (B) MCF-7 human breast cancer cells in mixed cell culture assays with L cells which express recombinant G129 human prolactin variant hPRLA after three days in culture.

Figure 10A:
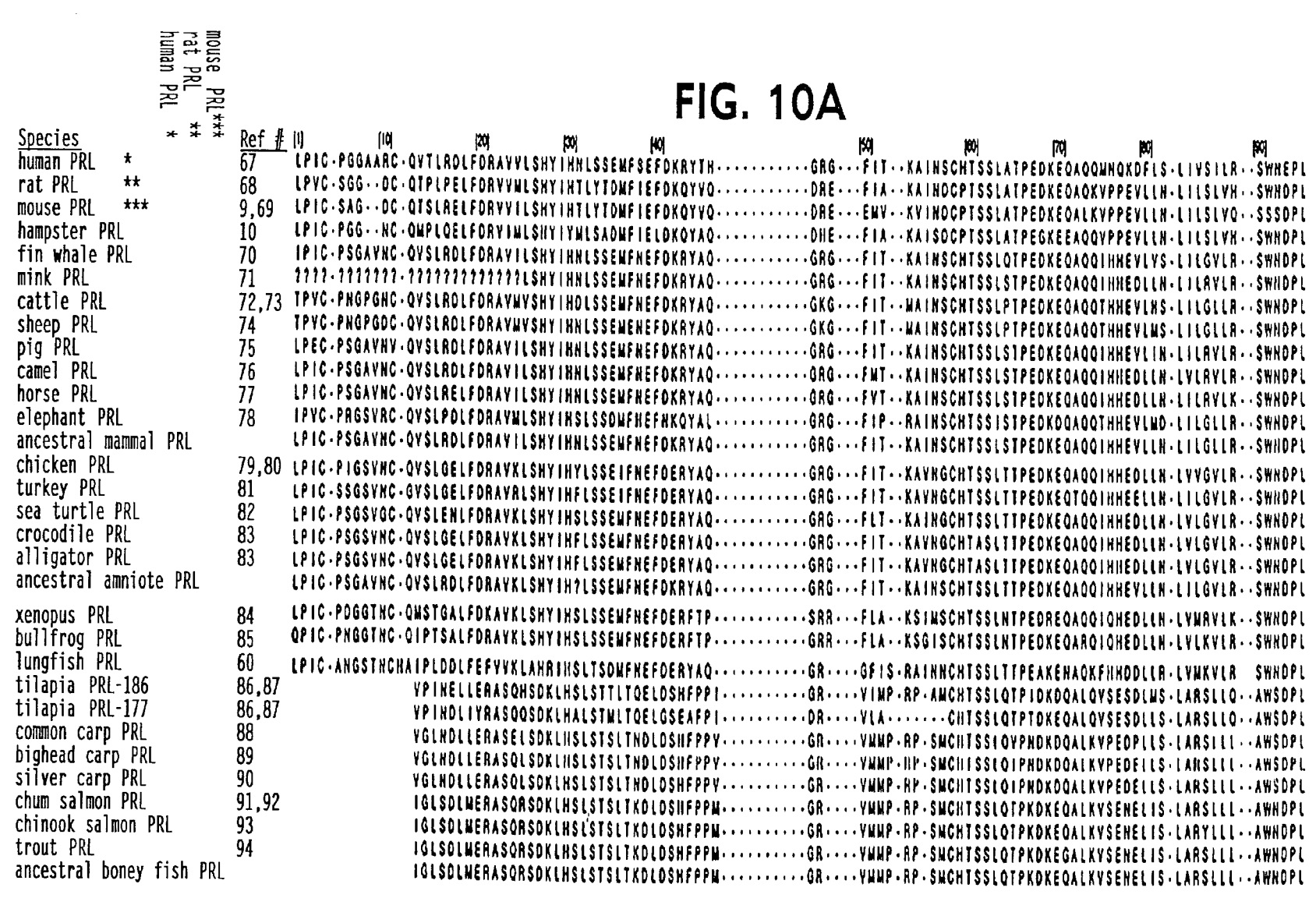
Figure 10B:
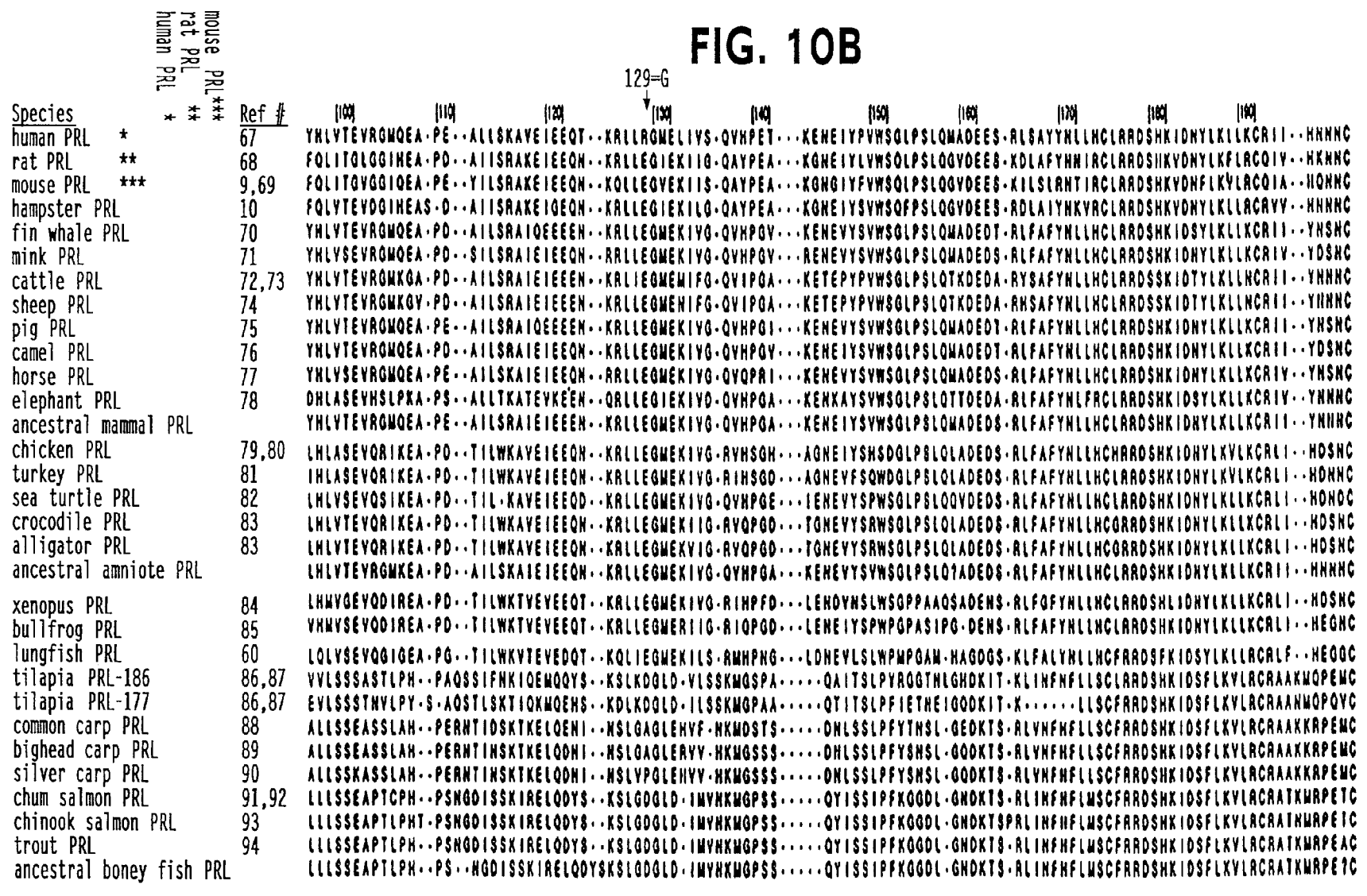

FIGS. 10A–B. Amino acid sequences (SEQ ID NOS 1–31) of various human and non-human forms of prolactin.

Figure 11:
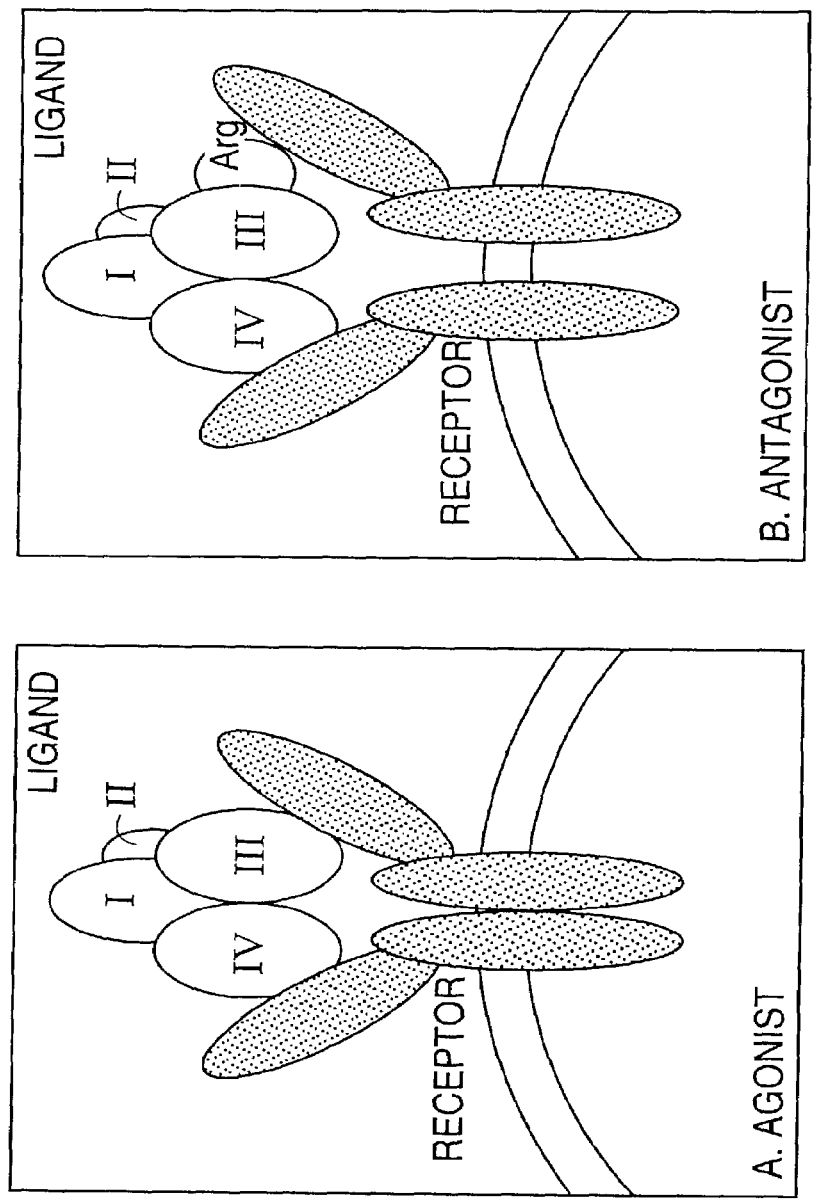

FIG. 11. Schematic illustration of the mechanism of GH or hPRL (ligand) antagonist. Four helical regions in the ligand (dotted ovals) are labeled as I, II, III and IV. Two membrane bond receptors (shaded ovals) are also shown in the figure. Arg represents the substitution mutation in the third α-helix resulting in hindering a second receptor to form a functional complex (from A to B).

Figure 12:
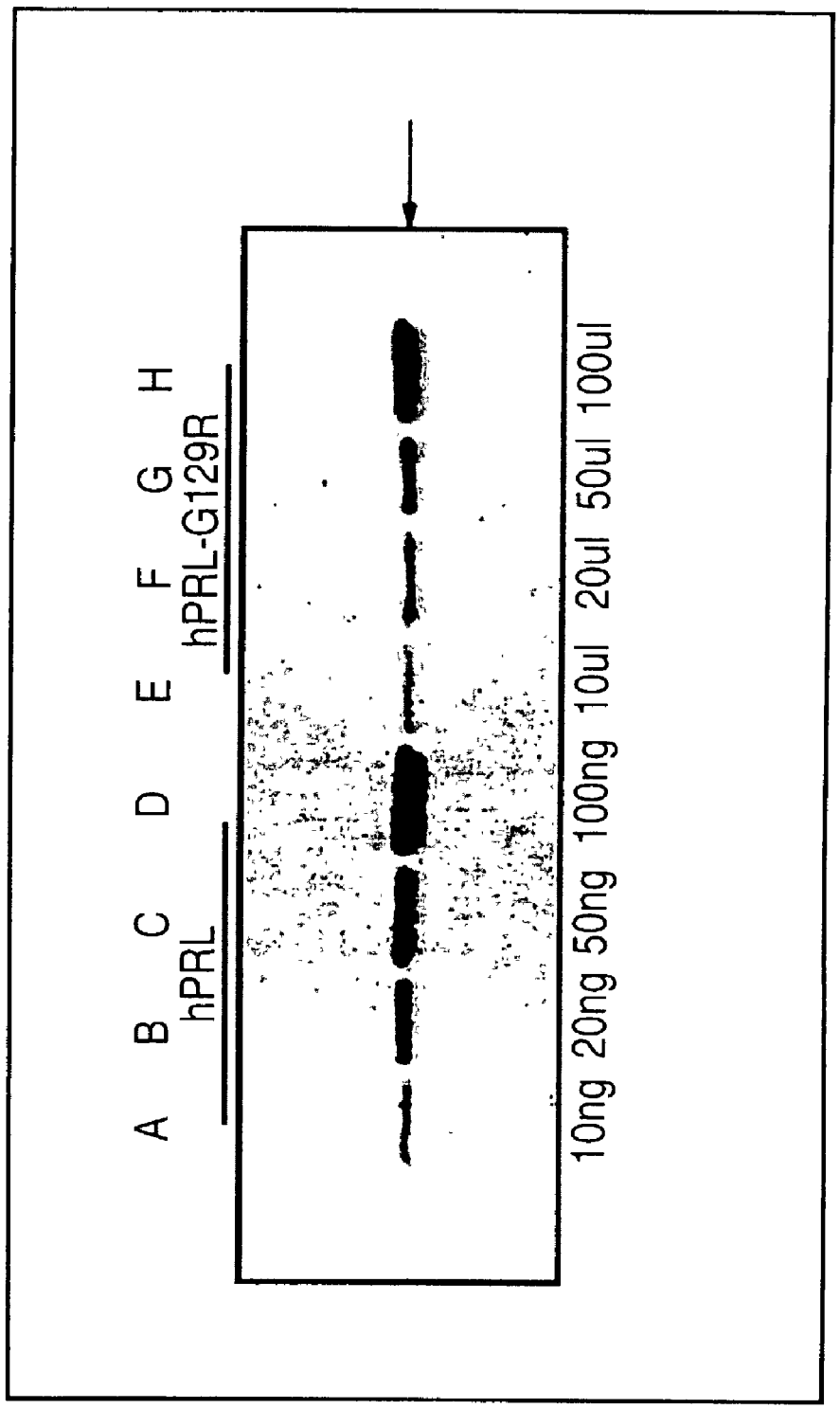

FIG. 12. Immunoblot analysis of hPRL-G129R gene expression by mouse L cells transfected with the pcDNA3 vector genetically engineered to encode the G129R variant. Lanes A–D represent samples containing purified hPRL (from NIH) as standards. Lanes E–H represent culture media from stably transfected mouse L cells.

Figure 13:
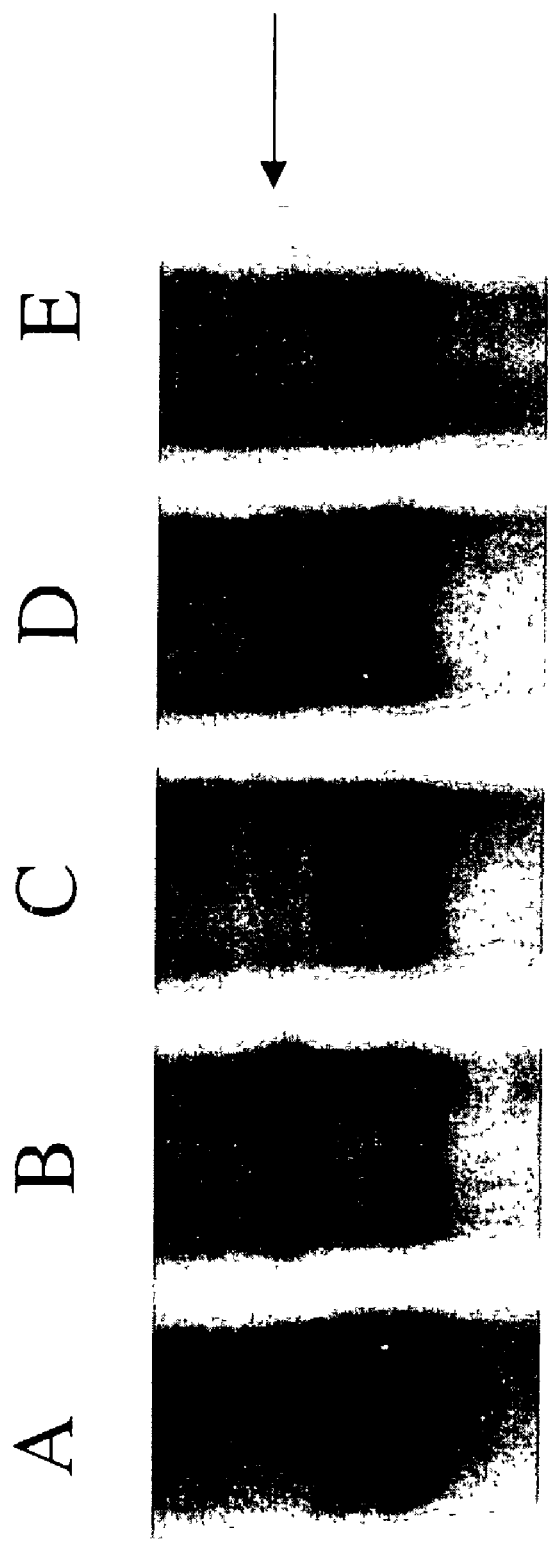
Figure 14A:
Figure 14B:
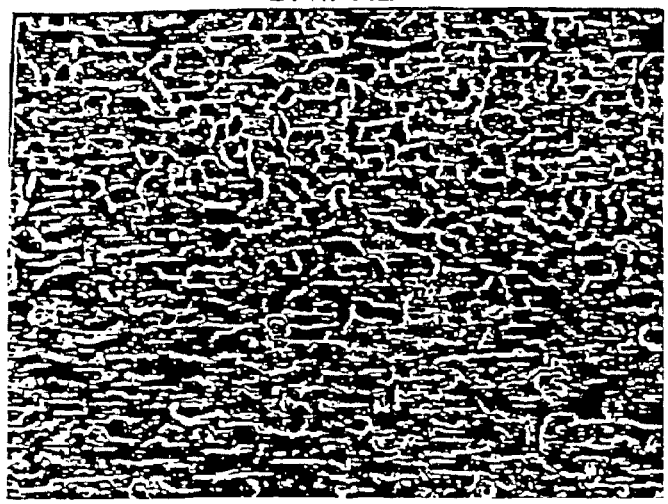
Figure 14C:
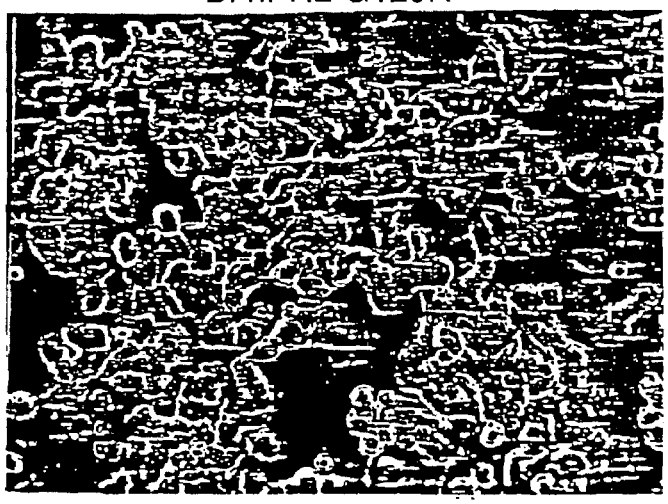
Figure 14D:
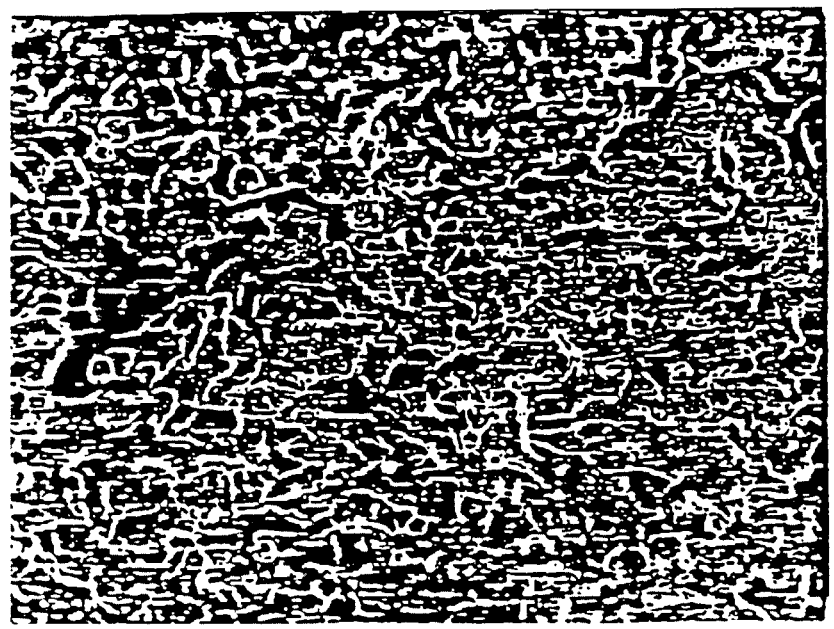
Figure 14E:
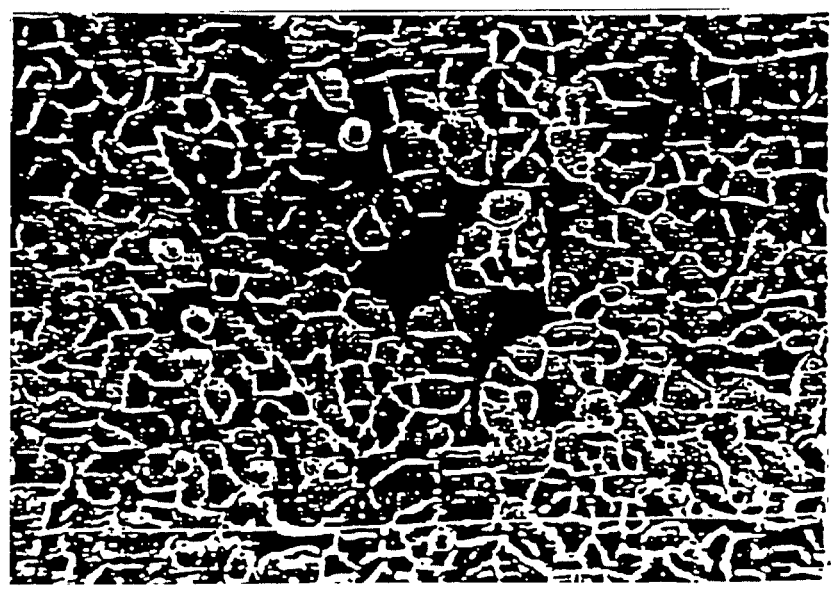

FIG. 13. Antagonistic effects of hPRL-G129R on tyrosine phosphorylation of STAT proteins induced by hPRL in human breast cancer cells (T47-D). Lane assignments are A, negative control; B, cells stimulated with 100 ng/ml HPRL; C, cells treated with 100 ng/ml of hPRL-G129R; D, cells treated with 100 ng/ml of hPR1 and 100 ng/ml of hPRL-G129R; E, cells treated with 100 ng/ml of hPRL and 500 ng/ml of hPRL-G129R. Arrow indicates the position of 95 kDa proteins.

FIGS. 14A–E. Light microscopic examination of T47-D human breast cancer cells after single dose of 200 ng/ml hPRL (15B); 200 ng/ml of HPRL-G129R (15C); 200 nM of E2 (15D); or 200 nM of 4-OH-Tamoxifen (15E) treatment after 4-day incubation as compared to control (15A).×200.

Figure 15:
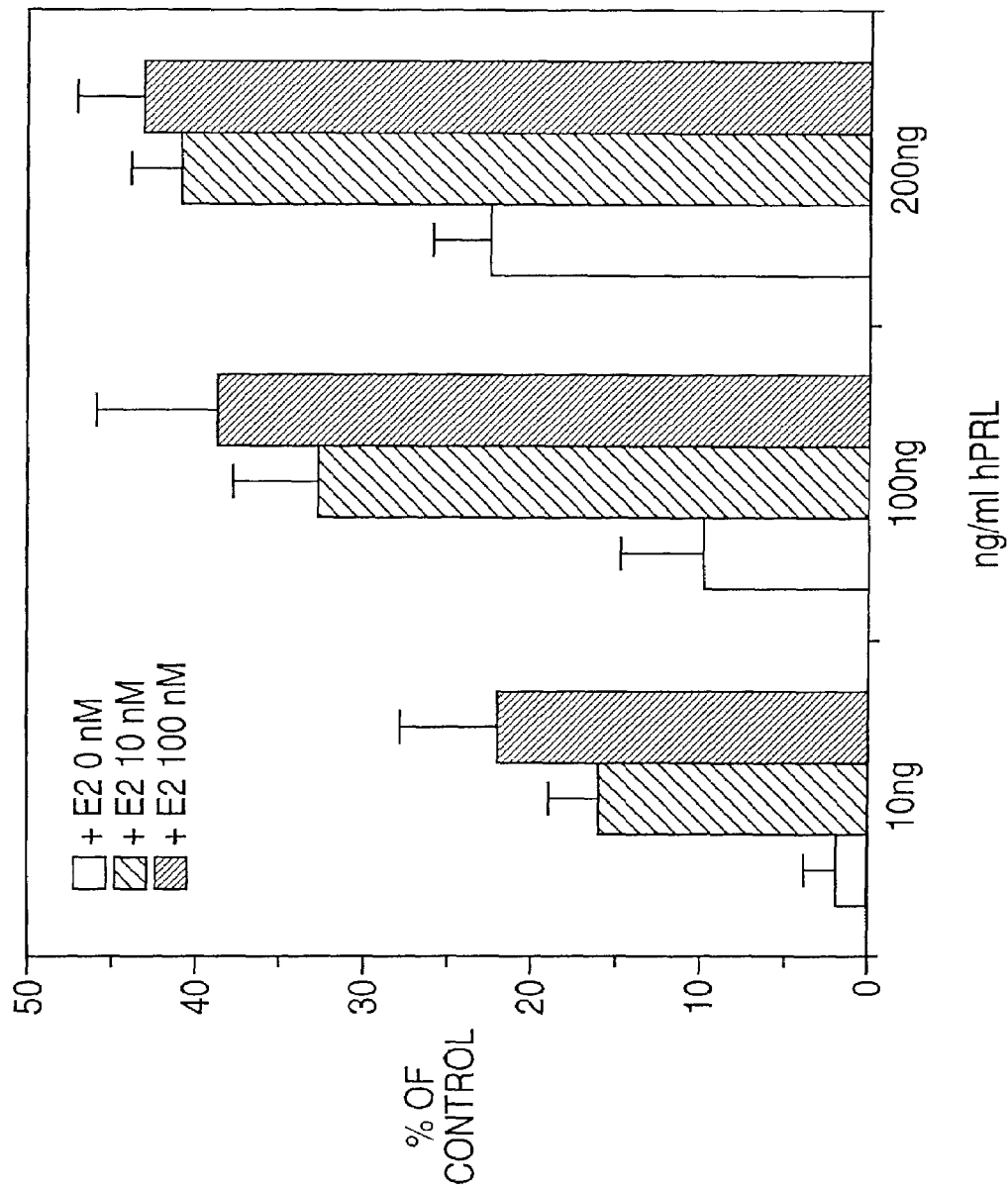

FIG. 15. Dose-response effects of hPRL and its synergistic effects with E2 in T47-D human breast cancer cell proliferation assay. The x-axis represents the HPRL concentration either in the absence (open bars) or presence of E2. Each data point represents a mean of at least three independent experiments with triplicate wells. Bars, SD.

FIGS. 16A–B. Dose-response effects of 4-OH-Tamoxifen (17A) and hPR1-G129R (17B). The x-axis represents the concentration of 4-OH-Tamoxifen (17A) and hPR1-G129R (17B). Each data point represents a mean of at least three independent experiments with triplicate wells. Bars, SD.

Figure 17:
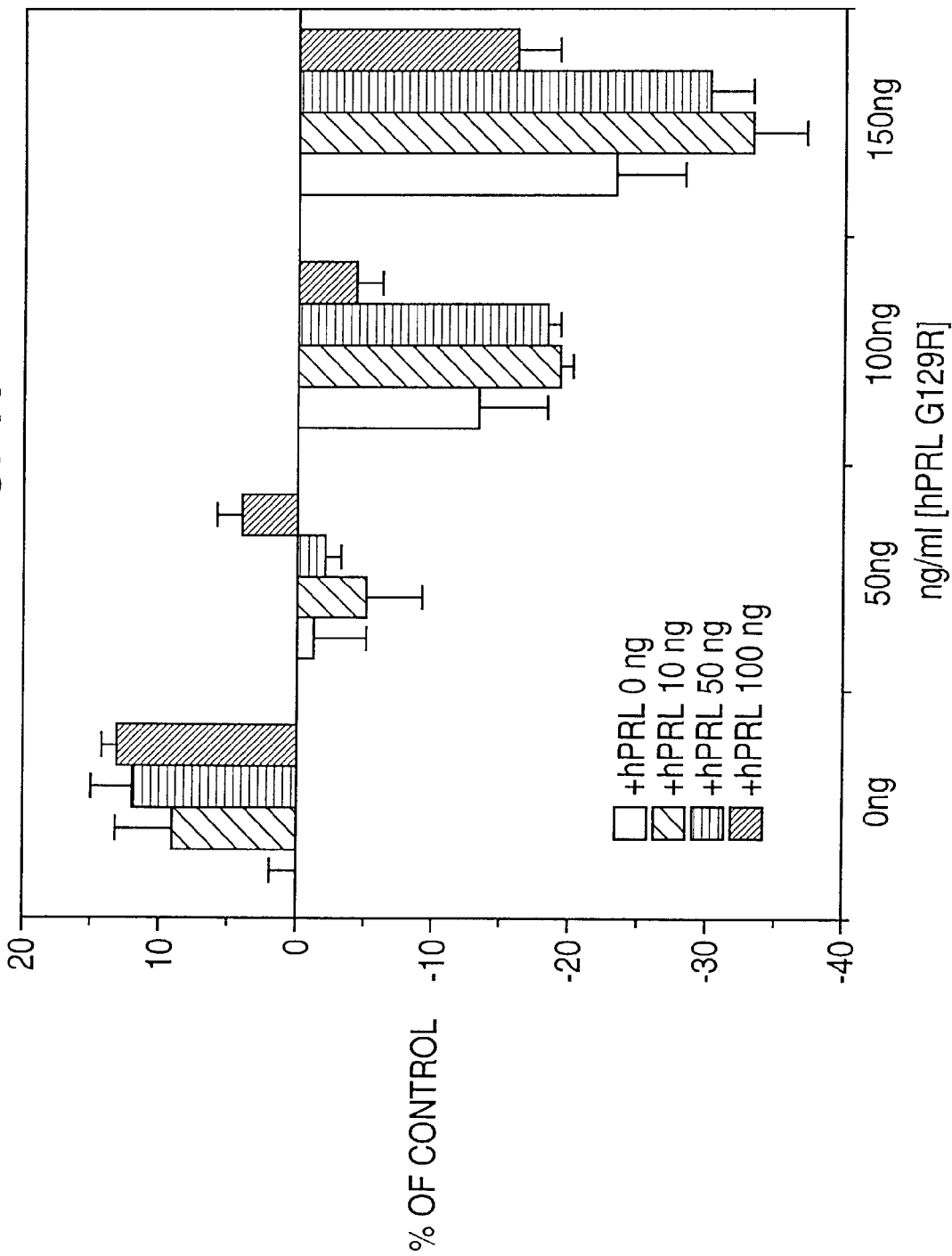

FIG. 17. Dose-response inhibitory effects of hPRL-G129R on hPRL induced T47-D cell proliferation. The x-axis represents the concentration of HPRL-G129R either in the absence of hPRL (open bars) and the presence of hPRL. Each data point represents a mean of at least three independent experiments with triplicate wells. Bars, SD.

Figure 18:
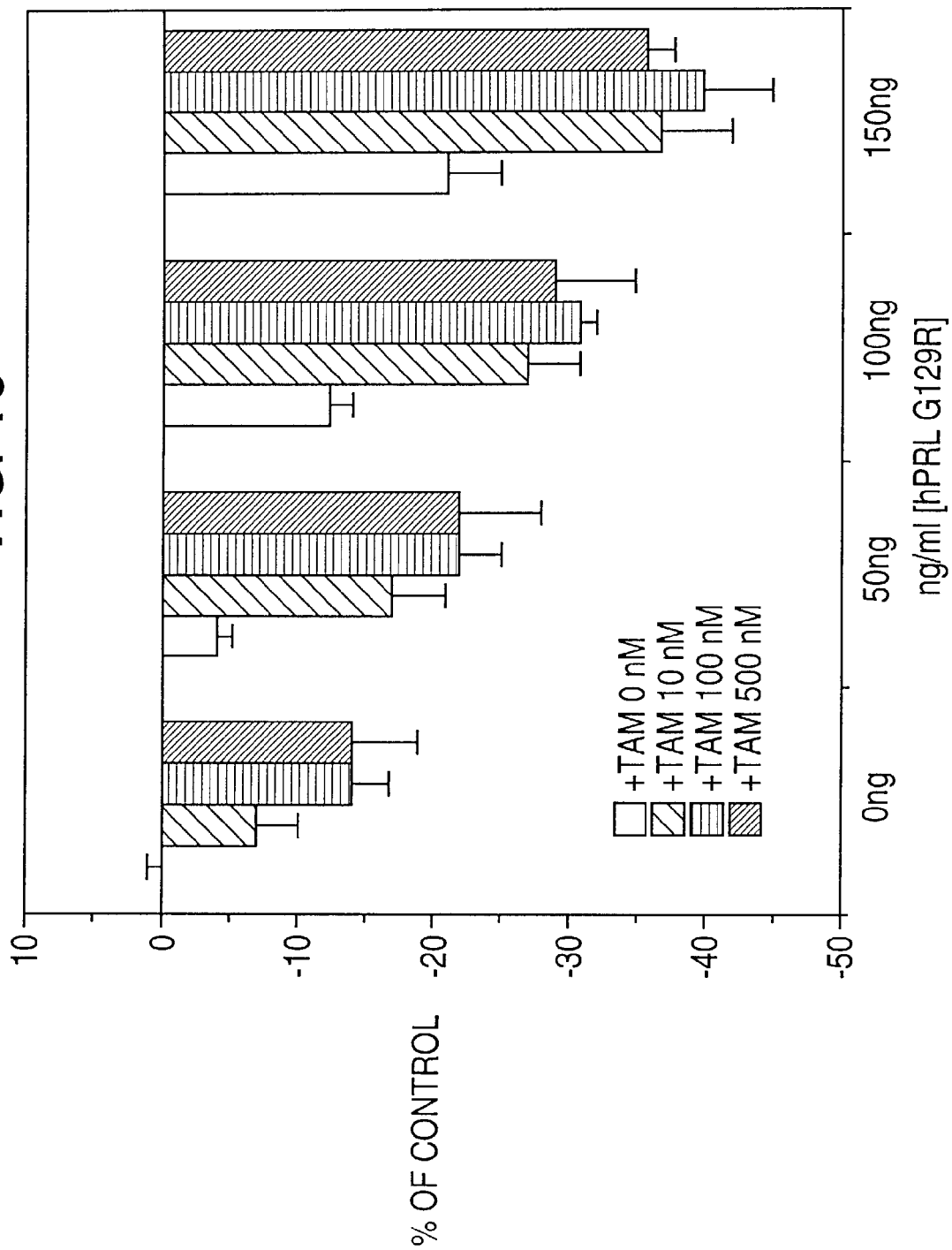

FIG. 18. Dose-response inhibitory effects of hPRL-G129R and its synergistic effects with 4-OH-Tamoxifen in T47-D human breast cancer cell proliferation assay. The x-axis represents the hPRL-G129R concentration either in the absence (open bars) or presence of 4-OH-Tamoxifen.

Each data point represents a mean of at least three independent experiments with triplicate wells. Bars, SD.

Figure 19A:
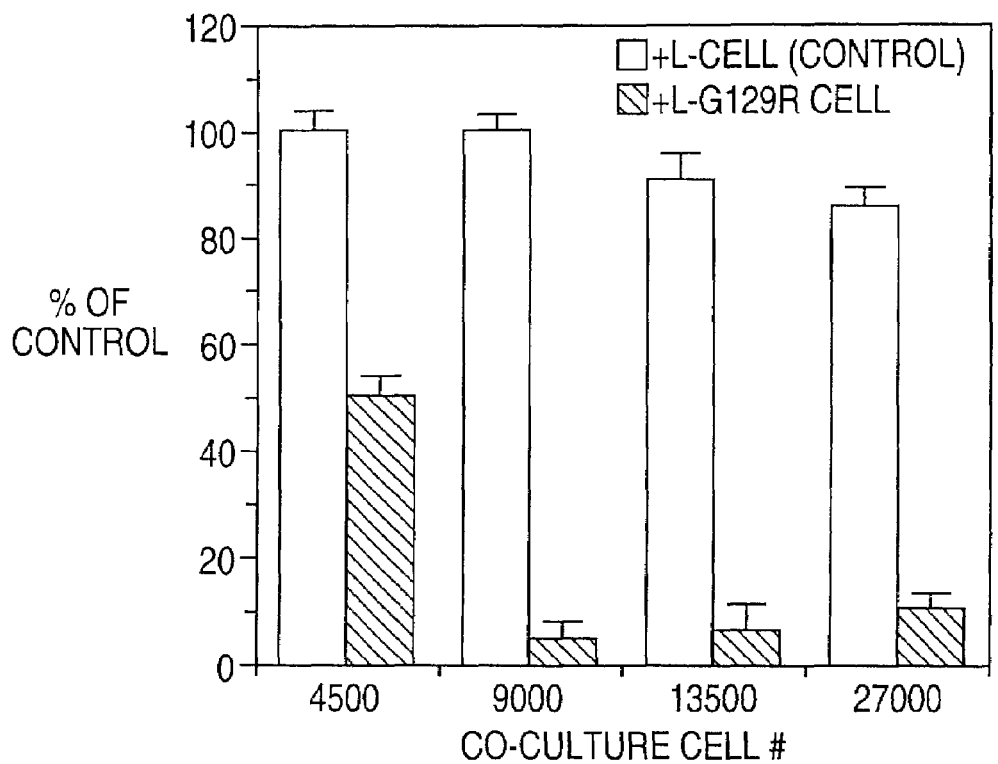
Figure 19B:
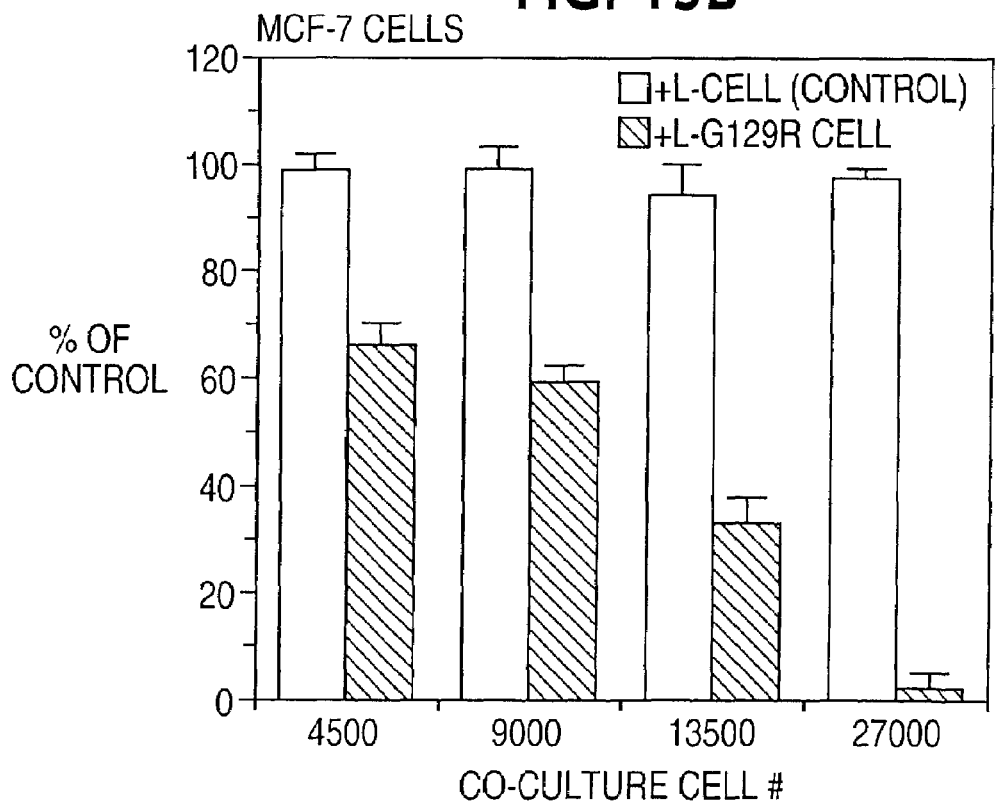

FIGS. 19A–B. Dose-response inhibitory effects of hPR1-G129R in two human breast cancer cell lines using co-culture method. The x-axis represents the co-cultured L cell (control) or L-hPRL-G129R cell numbers. Each data point represents a mean of at least three independent experiments with triplicates wells. Bars, SD.

FIGS. 20A–F. Dose response of T-47D human breast cancer cells to hPRL-G129R after 24 hours treatment using TUNEL assay (panels A–F). Panel (G) and (H) shows results of competition between hPRL and hPRL-G129R at 1:1 ratio (125 ng/ml hPRL+125 ng/ml hPRL-G129R; panel G) and 1:4 ratio (125 ng/ml hPRLG129R+500 ng/ml hPRL, panel H).

FIGS. 21A–E. Time course of T-47D human breast cancer cells responding to hPRL-G129R treatment (50 ng/ml) using TUNEL assay.

FIG. 22A–H. Response of multiple breast cancer cells to 4-OH-Tamoxifen treatment (1 µM for 24 hours) using TUNEL assay. Labels C and T stand for control and treated cells, respectively.

FIGS. 23A–F. Response of multiple breast cancer cells to treatment with 250 ng hPRL-G129R for 24 hours using TUNEL assay. Labels C and T stand for control and treated cells, respectively.

Figure 24:
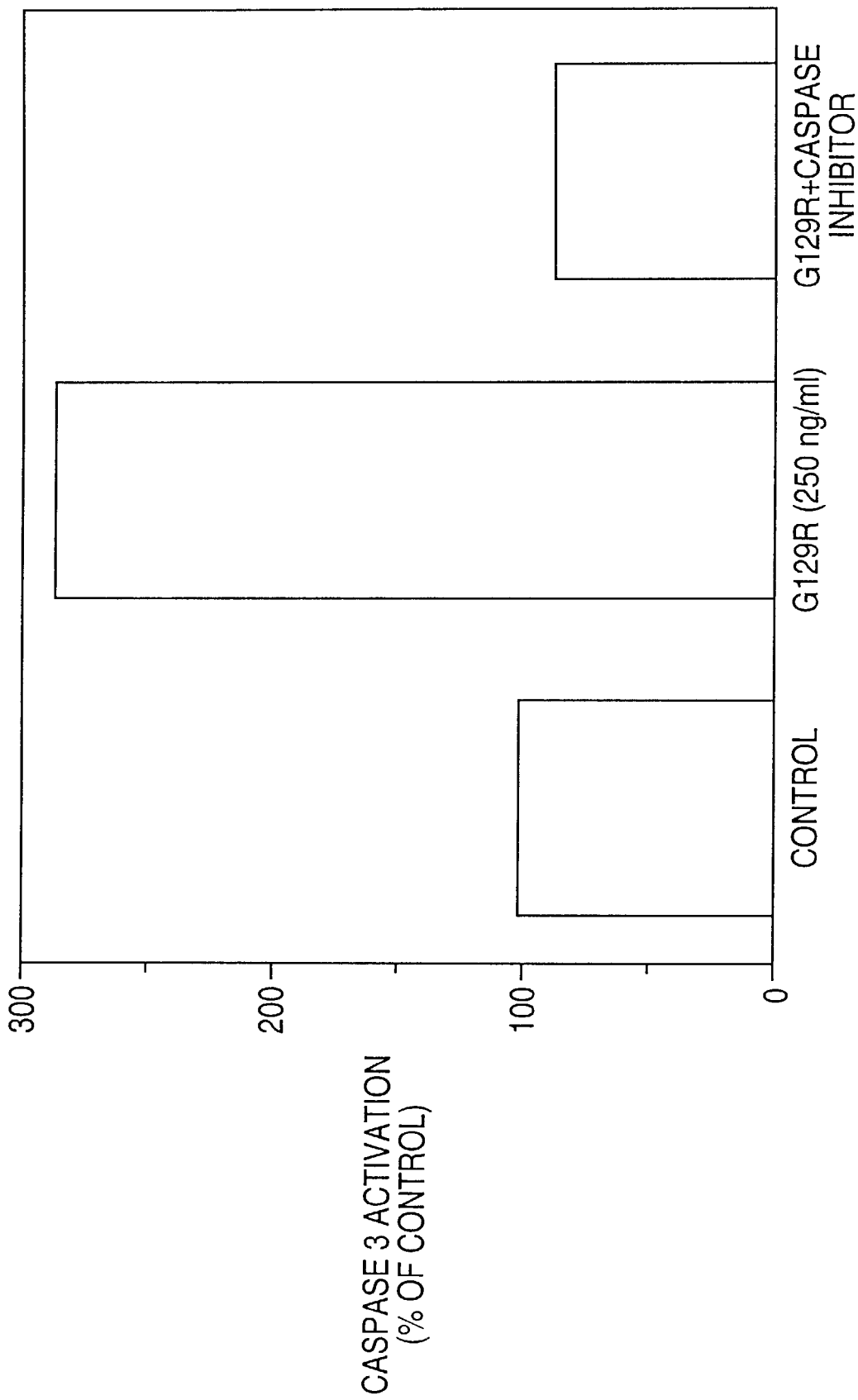

FIG. 24. Induction of Caspase-3 by bPRL-G129R. The effect of hPRL-G129R on Caspase-3 activation in T-47D cells using an ApopAlert CPP32/Caspase-3 assay kit (Clontech, Palo Alto, Calif.) is shown. T-47D cells were treated with 250 ng/ml of hPRL-G129R for 2 h. The assay was performed in the presence of DEVD-CHO (caspase-3 inhibitor) to demonstrate that the Caspase-3 induction by hPRL-G129R is a specific event. The samples were in duplicate and each sample constituted about 2 million cells.

FIG. 25. Response of two prostate cancer cells to treatment with 250 ng hPRL-G129R for 24 hours using TUNEL assay.

5. DETAILED DESCRIPTION OF THE INVENTION

For purposes of clarity, and not by way of limitation, the detailed description of the invention is divided into the following subsections:
(i) prolactin variants;
(ii) truncated prolactin receptors; and
(iii) utility of the invention.

5.1. Prolactin Variants

The present invention provides for prolactin (PRL) variants which antagonize the action of PRL at its receptor.

The term prolactin (PRL) refers herein to human and nonhuman animal forms of the hormone prolactin. Such prolactins include, but are not limited to, pro lactins for which the amino acid sequences are set forth in FIG. 10 (see also Cooke et al., 1981, J. Biol. Chem. 256:4007; Cooke et al., 1980, J. Biol. Chem. 225:6502; Kohmoto et al., 1984, Eur. J. Biochem. 138:227; Tsubokawa et al., 1985, Int. J. Peptide Protein Res. 25:442; Bondar et al., 1991, GenBank Accession No. #X63235; Sasavage et al., 1982, J. Biol. Chem. 257:678; Miller et al., 1980, Endocrinol. 107:851; Li et al., 1970, Arch. Biochem. Biophys. 141:705; Li, 1976, Int. J. Peptide Protein Res. 8:205; Martinant et al., 1991, Biochim. Biophys. Acta 1077:339; Lehrman et al., 1988, Int. J. Peptide Protein Res. 31:544; Li et al., 1989, Int. J. Peptide Protein Res. 33:67; Hanks et al., 1989, J. Mol. Endocrinol. 2:21; Watahiki et al., 1989, J. Biol. Chem. 264:5535; Karatzas et al., 1990, Nucl. Acids Res. 18:3071; Yasuda et al., 1990, Gen. Comp. Endocrinol. 80:363; Noso et al., Int. J. Peptide Protein Res. 39:250; Buckbinder et al., 1993, Proc. Natl. Acad. Sci. U.S.A. 90:3820; Takahashi et al., J. Mol. Endocrinol. 5:281; Yamaguchi et al., 1988, J. Biol. Chem. 263:9113; Rentler-Delrue et al., DNA 8:261; Yasuda et al., 1987, Gen. Comp. Endocrinol. 66:280; Chang et al., 1991, GenBank Acc. No. #X61049; Chang et al., 1991, GenBank Acc. No. #X61052; Yasuda et al., 1986, Arch. Biochem. Biophys. 244:528; Kuwana et al., 1988, Agric. Biol. Chem. 52:1033; Song et al., 1988, Eur. J. Biochem. 172:279; Mercier et al., 1989, DNA 8:119).

The term prolactin (PRL) variant refers to a form of prolactin which has been structurally altered relative to its native form, including where the amino acid sequence of the native form has been altered by the insertion, deletion, and/or substitution of amino acids.

The ability of such a variant to antagonize the action of PRL at its receptor is defined as the ability of the variant to inhibit an effect mediated, under normal conditions, by PRL. For example, where PRL has a proliferative effect on a species of cell, a PRL variant according to the invention inhibits the proliferation of the species of cells; without being limited by the following theory, it is believed that PRL is present at some level for an inhibitory effect to be observed. FIG. 5A illustrates a working example of the invention in which human prolactin (hPRL) induces the proliferation of T47D human breast cancer cells, whereas a variant of hPRL having a substitution of the glycine at position 129 with an arginine residue, termed hPRLA, inhibits proliferation of T47D cells relative to T47D cells lacking the added HPRL or hPRLA; it is believed that T47D levels produce PRL (Ginsberg and Vonderharr, 1995, Cancer Res. 55:2591–2595).

As a specific non-limiting example, a PRL variant may be identified as an antagonist of PRL by determining the ability of the variant to block the ability of PRL to act via its receptor when both PRL and the PRL variant are present. As an example, where a given concentration X of PRL is associated with an increase Y in the proliferation of cells expressing the PRLR in culture, when a comparable sample of cells are exposed to PRL at concentration X, and a PRL variant at a concentration V, the proliferation of the cells will increase by Z, where Z is less than Y and may be a negative number.

In one non-limiting embodiment of the invention, the PRL variant is a variant of human PRL having a substitution of the glycine at position 129 with another amino acid. The substitution, represented in shorthand form by G129*, where * is a naturally occurring or synthetic amino acid other than glycine, may be the sole variation from the native sequence or one of several alterations (including insertions, deletions, and/or substitutions of amino acids). The substituent amino acid may be neutral-polar amino acids such as alanine, valine, leucine, isoleucine, phenylalanine, proline, methionine; neutral non-polar amino acids such as serine, threonine, tyrosine, cysteine, tryptophan, asparagine, glutamine, aspartic acid; acidic amino acids such as aspartic and glutamic acid; and basic amino acids such as arginine, histidine or lysine. In preferred embodiments of the invention, the glycine at position 129 of hPRL may be substituted with valine, leucine, isoleucine, serine, threonine, proline, tyrosine, cysteine, methionine, arginine, histidine, tryptophan, phenylalanine, lysine, asparagine, glutamine, aspartic acid, and glutamic acid. In a most preferred embodiment of the invention, the substitution replaces the glycine at position 129 with arginine (G129R). In a further specific nonlimiting embodiment, the present invention provides for a prolactin variant wherein the glycine at position 129 is deleted.

In yet other nonlimiting embodiments, a prolactin variant is linked to another protein as part of a fusion protein. As one specific embodiment, the prolactin variant may be linked to interleukin 2. One nonlimiting example of such an embodiment is a G129R variant of human prolactin linked to interleukin 2.

The PRL variants of the invention may be prepared by chemical synthesis or by recombinant DNA techniques. Generally, a cDNA of PRL may be prepared using standard PCR amplification techniques, RNA or cDNA prepared from a cell which produces PRL (such as a pituitary cell) as a template, and oligonucleotide primers designed based on known PRL nucleic acid or amino acid sequence. A nonlimiting example of the preparation of a cDNA encoding HPRL is set forth in Section 7, below. Alterations may then be introduced into the PRL cDNA either randomly or by directed mutagenesis. An example of the use of oligonucleotide mediated site-directed mutagenesis is also set forth in Example 7, and illustrates the introduction of the G129R substitution into hPRL.

Where the PRL variant is to be produced by recombinant techniques, a nucleic acid encoding the PRL variant may be incorporated into an expression vector, operatively linked to a suitable promoter/enhancer sequence. The expression vector may further contain one or more elements which aid in the expression of the PRL variant, including a transcription termination site, a polyadenylation site, a ribosome binding site, a signal sequence, etc. Suitable expression systems include mammalian cells, insect cells, plant cells, yeast cells, slime mold, and organisms, including transgenic plants and transgenic animals. Suitable expression vectors include herpes simplex viral based vectors such as pHSV1 (Geller et al., 1990, Proc. Natl. Acad. Sci. U.S.A. 87:8950–8954); retroviral vectors such as MFG (Jaffee et al., 1993, Cancer Res. 53:2221–2226), and in particular Moloney retroviral vectors such as LN, LNSX, LNCX, LXSN (Miller and Rosman, 1989, Biotechniques 7:980–989); vaccinia viral vectors such as MVA (Sutter and Moss, 1992, Proc. Natl. Acad. Sci. U.S.A. 89:10847–10851); adenovirus vectors such as pJM17 (Ali et al., 1994, Gene Therapy 1:367–384; Berker, 1988, Biotechniques 6:616–624; Wand and Finer, 1996, Nature Medicine 2:714–716); adeno-association virus vectors such as AAV/neo (Mura-Cacho et al., 1992, J. Immunother. 11:231–237); lentivirus vectors (Zufferey et al., 1997, Nature Biotechnology 15:871–875); plasmid vectors such as pCDNA3 and pCDNA1 (InVitrogen), pET 11a, pET3a, pET11d, pET3d, pET22d, and pET12a (Novagen); plasmid AH5 (which contains the SV40 origin and the adenovirus major late promoter), pRC/CMV (InVitrogen), pCMU II (Paabo et al., 1986, EMBO J. 5:1921–1927), pZipNeo SV (Cepko et al., 1984, Cell 37:1053–1062), pSRα (DNAX, Palo Alto, Calif.) and pBK-CMV; and baculovirus expression vectors (O'Reilly et al., 1995, Baculovirus Expression Vectors, Oxford University Press), such as p2Bac (InVitrogen).

A PRL variant produced in a recombinant expression system may then be purified by standard techniques, including electrophoresis, chromatography (including affinity chromatography), and ultrafiltration.

5.2. Truncated Prolactin Receptors

The present invention provides for cell-free truncated prolactin receptors (referred to herein as PRL-BP(s)), which retain the ability to bind to PRL and therefore are able to compete with the cell surface forms of PRLR for PRL binding, thereby inhibiting the ability of PRL to interact with its receptor.

A PRL-BP may be prepared by removing all or a part of the transmembrane and/or intracellular domains of the PRLR, either enzymatically or using recombinant DNA techniques. In a specific, nonlimiting embodiment of the invention, the PRLR to be truncated is as described in Boutin et al., 1989, Mol. Endocrinol. 3:1455–1461.

For recombinant preparation, nucleic acid molecules encoding the native prolactin receptor may be prepared and then altered to encode a PRL-BP. For example, but not by way of limitation, the PRLR may be cloned using techniques as set forth in Example 9, below.

The amino acid sequence of PRLR from a variety of different organisms is known. The human PRLR sequence is obtainable from Genbank Accession No: 13032. Further, the amino acid residues which delineate the extracellular, transmembrane and cytoplasmic domains of the PRLR are also known (see for example, Kelly et al., 1989, Biol Reprod 40:27–32). Given the elucidation of these domains, one skilled in the art would readily be capable of producing a truncated form of PRLR which retains the ability to bind PRL, but which may by used to inhibit the effects of PRL.

Recombinant DNA methods which are well-known to those skilled in the art can be used to construct expression vectors containing PRL-BP coding sequences and appropriate transcriptional/translational control signals. The efficiency of expression can be enhanced by the inclusion of appropriate transcriptional enhancer elements, transcriptional terminators, etc. The methods may include in vitro recombinant DNA and synthetic techniques and in vivo recombinants (See, for example, Sambrook et al., 1989, Molecular Cloning: A Laboratory Manual, Cold Spring Harbor Press, Cold Spring Harbor, N.Y., and Glover, D. M., (ed.), 1985, DNA Cloning: A Practical Approach MRL Press, LTD., Oxford, U.K., Vol. I,II) which are incorporated by reference herein in their entirety.

When recombinant DNA technology is used to produce PRL-BP, it may be advantageous to engineer fusion proteins that can facilitate, for example, solubility or purification. Such fusion proteins can be made by ligating the appropriate nucleic acid sequences encoding the desired amino acid sequences to each other by methods known in the art, in the proper reading frame, and expressing the fusion protein by methods commonly known in the art. The PRL-BP gene product contained within such fusion proteins can comprise, for example, one or more of the extracellular domains or portions, preferably the ligand-binding portion.

In one specific example, for hPRL-BP expression, a mammalian expression vector such as pcDNA3.1/His Xpress (Invitrogen Corp., San Diego, Calif.) may be used. This vector contains a human immediate-early cytomegaiovirus promoter and bGH poly A addition signal. In addition, it offers an in frame (His)6 (SEQ ID NO: 32) peptide at the N-terminus which allows an easy detection after purification of hPRL-BP. Recombinant hPRL-BP produced using such a vector in cell culture may be concentrated by ultrafiltration, using techniques as set forth in Section 7 below. The concentration of hPRL-BP following ultrafiltration may be determined by protein assay and confirmed by Western Blot analysis using anti-His antibody (Santa Cruz, Calif.) and may be quantified by densitometric methods (Fernadez and Kopchick, 1990, Anal. Biochem. 191:268–271).

Alternatively, a truncated PRL-BP may be made by protein synthesis techniques, e.g., by use of a peptide synthesizer. In addition, truncated PRL-BP may be prepared by purification of full length PRLR protein, from either naturally occurring or genetically engineered PRLR producing cells, followed by enzymatic cleavage of the purified protein using proteolytic enzymes, such as trypsin, to form PRL-BP.

5.3. Screening Assays for Identification of PRLR Agonists and Antagonists

The present invention provides a cell-based assay system that can be used to identify compounds or compositions that modulate PRLR activity, and therefore, may be useful for regulation of cell proliferation and treatment of diseases associated with aberrant cell proliferation. The cell-based assay system of the invention is designed to assay for cellular apoptosis. The assay system is based on the observation that the PRLR antagonist G129R is capable of inducing apoptosis in cells expressing the PRLR.

In accordance with the present invention, a cell-based assay system is provided to screen for compounds that modulate the activity of PRLR, and thereby, modulate cell proliferation. Compounds that may affect PRLR activity include but are not limited to compounds that bind to the PRLR and either activate signal transduction (agonists) or block activation (antagonists). The invention assay systems provide rapid, reliable methods to identify compounds which interact with, and thereby affect the function of PRLR.

A method for identifying a compound capable of modulating prolactin receptor activity, comprises the following steps:
a. contacting a compound to a cell that expresses the prolactin receptor;
b. measuring the level of apoptosis in the cell; and
c. comparing the level of apoptosis obtained in (b) to the level obtained in the absence of the compound;

such that if the level obtained in (b) differs from that obtained in the absence of a compound, a compound capable of modulating prolactin receptor activity has been identified. If the level of apoptosis is increased in such an assay an antagonist of the prolactin receptor has been identified.

In yet another embodiment of the invention, a method for identifying a compound capable of inducing the activity of the prolactin receptor, is provided that comprises the following steps:
a. contacting a compound to a cell that expresses the prolactin receptor, in the presence and absence of a compound that induces prolactin receptor mediated apoptosis;
b. measuring the level of apoptosis in the cell in the presence and absence of the compound that induces prolactin receptor mediated apoptosis; and
c. comparing the levels of apoptosis obtained in (b));

such that if the level of apoptosis is decreased in the presence of the compound that induces prolactin receptor mediated apoptosis, a compound capable of activating the activity of the prolactin receptor has been identified.

To this end, cells that endogenously express PRLR can be used to screen for compounds that modulate the activity of the receptor. In a preferred embodiment of the invention the cells are transformed cells, such as for example, breast cancer cells or prostate cancer cells. In addition, cells that do not normally express PRLR can be genetically engineered to express the PRLR gene and such cells may be used for screening purposes. Those of skill in the art recognize that any cell line capable of transfection, and having low to no background level of the PRLR is acceptable.

In utilizing such cell-based assay systems, the cells expressing PRLR are exposed to a test compound or to vehicle controls (e.g., placebos). In assays designed for identification of PRLR agonists, compounds that induce PRLR mediated apoptosis, such as G129R, are also added to the assay. After exposure, the cells can be assayed to measure for the level of apoptosis. Assays designed to measure apoptosis include the terminal deoxynucleotidly transferase mediated dUTP nick end labeling (TUNEL) assay (Kebers et al., 1998, Experimental Cell Research 240:197–205); assays to detect activated caspases (Janicke et al., 1998, J. Biol. Chem. 273:9357–9360); DNA ladder gel assays to detect fragmented DNA by gel electrophoresis (Bursch et al., 1996, Carcinogenesis 17:1595–1607); assays to detect bcl-2 and bax protein levels (Wuerzberger et al., 1998, Cancer Research 58:1876–1885); Hoechst/DAPI staining to detect nuclear condensation in apoptotic cells (Bursch et al., 1998, Carcinogenesis 17:1595–1607); Annexin V staining of phospatidyl serine on the cytoplasmic membrane (van Engeland et al., 1996, Cytometry 24:131–139); analysis of DNA content by propidium iodide staining followed by flow cytometry (Sherwood et al., Methods in Cell Biology 46:77–97; and morphological studies using electron and phase contrast microscopy (Bursch et al., Carcinogenesis 17:1595–1607).

The ability of a test compound to induce the level of apoptosis, above those levels seen with cells treated with a vehicle control, indicates that the test compound acts as an antagonist to inhibit signal transduction mediated by PRLR. In contrast, the ability of a test compound to reduce the level of apoptosis in the presence of compounds such as G129R, above those levels seen with cells treated with a vehicle control, indicates that the test compound induces signal transduction mediated by PRLR.

High throughput screening can be accomplished by plating the test cells into wells of microtiter plates, each of which will contain a potential PRLR antagonist or agonist. The wells will also contain complete medium, and in instances where an agonist is to be identified a compound such as G129R is included. After incubation with potential antagonists or agonists, the cells are assayed for apoptosis using methods such as those described above. Potential antagonists are those compounds that induce apoptosis in cells expressing the PRLR. Potential agonists are those compounds that compete with G129R for receptor binding and thereby inhibit G129R induced apoptosis.

The compounds which may be screened in accordance with the invention include, but are not limited to inorganic compounds, peptides, antibodies and fragments thereof, and other organic compounds (e.g., peptidomimetics) that bind to PRLR and either activate the activity of PRLR (i.e., agonists) or inhibit the activity of PRLR (i.e., antagonists). Compounds may include, but are not limited to, peptides such as, for example, soluble peptides, including but not limited to members of random peptide libraries; (see, e.g., Lam et al., 1991, Nature 354:82–84; Houghten et al., 1991, Nature 354:84–86), and combinatorial chemistry-derived molecular library made of D- and/or L-configuration amino acids, phosphopeptides (including, but not limited to, members of random or partially degenerate directed phosphopeptide libraries; see, e.g., Songyang et. al., 1993, Cell 72:767–778). Screening the libraries can be accomplished by any of a variety of commonly known methods. In a specific embodiment of the invention, peptide variants of PRL may be screened for their ability to regulate the activity of the PRLR.

Compounds identified via assays such as those described herein may be useful, for example, for ameliorating diseases associated with aberrant cell proliferation. Assays for testing the efficacy of compounds identified in the screens can be tested in animal model systems for proliferative disorders, such as cancer.

5.4. Utilities of the Invention

The present invention provides for methods and compositions whereby a PRL variant (which acts as a PRL antagonist) or a truncated form of the PRLR (which competes with endogenous receptor for PRL binding) may be used to inhibit the effects of PRL, and in particular, may be used to inhibit PRL-mediated cell proliferation. The method of the invention comprises the administration of a prolactin variant, or a truncated form of the PRLR, to a subject having a proliferative condition wherein the proliferating cells express a prolactin receptor.

In particular specific nonlimiting embodiments, a PRL variant or a truncated PRLR (also referred to as a PRL-BP) of the invention may be tested for the ability to antagonize PRL activity in a panel of cell lines expressing different levels of the PRLR and/or PRL, so as to permit the inference of an effect which varies according to PRL/PRLR availability. For example, the activity of a hPRL variant or a truncated hPRLR may be tested in all or a subset of the following five different human breast cancer cell lines (T-47D, MCF-7, HTB19, HTB20, and HTB123 from ATCC). The hPRL receptor numbers on these cell lines have been reported to be: T-47D (25,800/cell), MCF-7 (8,300/cell), HTB19 (6,435/cell), HTB20 (5,480/cell), HTB123 (1,094/cell, normal breast cell=1,700/cell). Therefore, these cell lines represent a spectrum of hPRL receptor levels on human breast cancer cells. It should be noted that the use of human breast cancer cell lines is preferred over the use of the rat Nb2 T-cell lymphoma cell line, widely used in the lactogenic hormone studies, in order to avoid the potential confusing effects caused by species specificity. Assays which may be used to determine the effects of the PRL variant or the truncated PRLR include (i) (for variant PRL) a competitive receptor binding assay, to examine if the antagonists are competing at the receptor level; (ii) detection/quantitation of phosphorylation of STAT 5 protein to examine if the putative antagonist inhibits the intracellular signal transduction induced by PRL; and (iii) a cell proliferation assay, which is used as an overall test for the potential inhibitory effects of a variant PRL or a truncated PRLR. One preferred method of testing the proliferative or anti-proliferative effects of PRL, variant PRL; or truncated PRLR is a mixed cell culture assay such as that diagramed in FIG. 6 and explained in Section 8 below.

Conditions which may benefit from the administration of a PRL variant or a PRL-BP of the invention include both benign and malignant proliferation of cells which express a PRLR. Such conditions include but are not limited to proliferative diseases of the breast, including benign conditions such as breast adenomas and fibrocystic disease, and malignant conditions such as breast cancer, including ductal, scirrhous, medullary, colloid and lobular carcinomas (local or metastatic); and proliferative diseases of the prostate, including benign prostatic hypertrophy and prostate cancer (local or metastatic). Proliferative conditions involving cells which express a receptor homologous to the PRLR may also be treated, including conditions involving cells which express a growth hormone receptor.

As set forth in Example 11, below, prolactin variants are capable of inducing cellular apoptosis in human breast cancer cells and prostate cancer cells. Thus, the present invention provides methods for inducing apoptosis in cells expressing the prolactin receptor, as well as cells expressing a receptor homologous to the prolactin receptor, thereby inhibiting proliferation of such cells. In an embodiment of the invention, expression of the PRLR receptor can be targeted to a specific cell population targeted for apoptosis, such as a cancer cell population. Nucleic acid molecules expressing PRLR can be transferred into the targeted cell population using methods such as those employed in gene therapy protocols. Once expressed on the surface of the targeted cell population, the receptor can be activated through contact with prolactin variants to induce apoptosis of the targeted cell.

In the treatment of proliferative conditions, the PRL variant or PRL-BP may be administered either in isolation or as part of a sequential or combined treatment regimen. As nonlimiting examples, where the condition to be treated is breast cancer, additional agents used in a combined regimen may include anti-estrogens such as tamoxifen and/or a chemotherapeutic agent. Where the condition to be treated is prostate cancer, additional agents used in a combination regimen may include an anti-androgen and/or a chemotherapeutic agent. A combined treatment regimen is based on the observation that the use of a prolactin variant, in combination with an anti-estrogen, such as 4-OH tamoxifen, exhibited a synergistic inhibitory effect.

The present invention accordingly provides for compositions comprising a PRL variant or PRL-BP, in a suitable pharmaceutical carrier, for use in the foregoing methods. Such compositions may be administered by any suitable technique, including local application, intravenous, intraarterial, intrathecal, intraperitoneal, oral, etc.

Pharmaceutical compositions suitable for use in the present invention include compositions containing a PRL variant or PRL-BP in an effective amount to achieve its intended purpose. More specifically, an effective dose refers to that amount of PRL variant or PRL-BP required to inhibit proliferation of cells expressing the PRLR thereby decreasing the symptoms associated with a proliferative condition. Determination of effective amounts is well within the capability of those skilled in the art.

The effective concentrations of the compounds of the invention may be established in cell culture systems and/or in transgenic animals. The effective dose may be determined using a variety of different assays. For example, cell proliferation assays may be conducted to quantitate the concentration of PRL variant or PRL-BP required to inhibit cell proliferation. In addition, assays may be performed to quantitate the concentration of PRL variant or PRL-BP required to induce cellular apoptosis. Inhibition of tumor cell growth can be assayed to detect PRL variant or PRL-BP mediated inhibition of tumor cell proliferation. In such instances, the effective dose of PRL variant or PRL-BP is that amount required to inhibit the proliferation of cancer cells and inhibit the growth of a tumor in a patient. In certain instances, it may be desirable to co-administer to a subject exhibiting a proliferative condition, prolactin variants or PRL-BP in conjunction with, one or more, additional agent. Such agents include, for example, anti-estrogens, such as tamoxifen, or anti-androgens. Determination of effective amounts of these additional compounds is well within the capability of those skilled in the art.

The amount of the composition will, of course, also be dependent on the subject being treated, the proliferative disorder being treated, the severity of the disorder symptoms and the judgment of the prescribing physician. In some instances it may be necessary to adjust the treatment to a lower dose due to undesirable side effects as well as adjusting the treatment to higher levels if the clinical response is not adequate.

6. EXAMPLE

Design of a Variant Prolactin Having Antagonist Activity

Since there is no crystal structural data presently available regarding hPRL, a computer algorithm program developed by Gamier et al., 1978, J. Mol. Biol. 120:97–120, was used to analyze and compare the secondary structures of hPRL and hGH. The results showed that the overall α-helix regions are very similar, suggesting that these hormones share a similar overall conformation. When the amino acid sequences in the third α-helix were compared between GHs and PRLs, it is clear that the Gly 129 of hPRL corresponds to Gly 120 of hGH and it is absolutely conserved among the GH/PRL family (Chen et al., 1994, J. Biol. Chem. 269: 15892–15897). Therefore, a Gly to Arg substitution mutation in hPRL was prepared in order to generate a hPRL receptor specific antagonist.

7. EXAMPLE

Preparation of the G129R Prolactin Variant

7.1. Cloning of the Human Prolactin Gene

Human PRL was successfully cloned using reverse transcription (RT) followed by polymerase chain reaction (PCR). Briefly, human pituitary polyA RNA (CloneTech, Ins. Palo Alto, Calif.) was used as template. A hPRL antisense primer was designed starting 2 bases from the stop codon (TAA) of hPRL cDNA (5'GCTTAGCAGTTGTTGT-TGTG 3') (SEQ ID NO: 33) and a sense primer was designed from ATG (5'ATGAACATCAAAGGAT 3') (SEQ ID NO: 34). RT/PCR was carried out using a kit from Perkin-Elmer Cetus, Inc. (Norwalk, Conn.). The nucleotide sequence of the resulting hPRL was determined by the dideoxy chain-termination method using modified T7 DNA polymerase (Sequenase, United States Biochemical), and was found to be identical to that reported in GenBank except for a one base difference which results in a silent mutation at codon 21 (CTG→CTC). A schematic representation of the cloning process, including preparation of the pUCIG-Met expression vector, is summarized in FIG. 1.

7.2. Creation of the G129R Prolactin Variant

The parental plasmid which contains the hPRL cDNA and a M13 F1 origin of replication (FIG. 1) was transformed into E. coli (CJ236). Single stranded plasmid DNA containing uridine was isolated from the transformed CJ236 bacteria using the helper bacteriophage, M13k07. Six pmol of oligonucleotide containing sequence directing the G129R mutation was annealed with 0.2 pmol of single stranded DNA in annealing buffer (200 mM Tris-HCl, 20 mM $MgCl_2$, 100 mM NaCl) by heating to 70° for 5 minutes followed by slow cooling. The oligonucleotide (5'GGGCTCCTA-GAGAGGATG-GAGCT3')(SEQ ID NO: 35), which encodes the G129R mutation was used to prime synthesis of a complementary strand of DNA, using single stranded DNA as a template, that is catalyzed by T4 DNA polymerase. After synthesis, the double stranded DNA was used to transform E. Coil (DH5a). Individual clones were isolated and screened for hPRL-G129R by DNA nucleotide sequencing. The G129R hPRL variant is hereafter referred to as hPRLA, the "A" referring to its antagonist activity.

7.3. Expression of Cloned Proteins

The hPRL and hPRLA-encoding nucleic acids were each inserted into a mammalian cell expression vector in which transcription of the cDNAs is controlled by the mouse metallothionein enhancer/promoter sequence and bGH poly A addition signal (Chen et al., 1991, J. Biol. Chem. 266: 2252–2258; Chen et al., 1991, Endocrinol. 129:1402–1408; Chen et al., 1991, Mol. Endocrinol. 5:1845–1852; Chen et al., 1994, J. Biol. Chem. 269:15892–15897). To establish stable mouse L cell lines which produce hPRL and hPRLA, mouse L cells [thymidine kinase-negative (TK) and adenine phosphoribosyl transferase-negative (APRT)] were selected as an in vitro expression system. Stable cell lines which express HPRL (which will be used as positive control) and hPRLA (~5–10 mg/1/24 h/million cells) were prepared.

Membrane ultrafiltration was used to partially purify as well as concentrate hPRL and hPRLA from conditioned cell culture media, using techniques as set forth in Chen et al., 1994, J. Biol. Chem. 269:15892–15897. The separation is based on the relative molecular size and the pore size of membrane. The ultrafiltration membranes were obtained from Amicon, Inc. (Northorough, Mass.). Two types of membranes were used, YM10 and YM100. A 200 ml stirred cell with Amicon YM100 under 20 psia transmembrane pressure was first used for removal of large impurities from the culture media. The permeate (>90% of recovery of hPRL) was applied onto a second filtration protocol which uses YM10 membrane to reduce the volume of solution and thus concentrate the protein. The concentration of HPRL or hPRLA was determined using an immunoradiometric assay (IRMA) kit from Diagnostic Products Corp. (Los Angeles, Calif.).

8. EXAMPLE

Inhibitory Activity of the G129R Prolactin Variant

8.1. Materials and Methods

Radioreceptor binding assay. Purified hPRL was labeled with $Na^{125}I$ by the lactoperoxidase method to a specific activity of 80–105 µCi/µg as described in Harding et al., 1996, J. Biol. Chem.271:6708–6712. Briefly, 1.0 mCi of $Na^{125}I$ was added to 1 mg of hPRL. Lactoperoxidase (10 µg dissolved in 10 µl of 0.4 mol/liter acetate butter, pH 5.6) and $H_2O_2$ (5 µl of 1.76 mmol/liter) were then added. After 30 min, the reaction was terminated by the addition of 100 µl of transfer buffer (0.47 mol/liter sucrose, 0.06 mol/liter KI, sodium azide 0.02%, pH 7.6). Radiolabeled hpRL was then separated by Sephadex G-100 chromatography. Human breast cancer cells were plated in 6-well plates. After pre-incubation in serum-free DMEM for 2–3 hours to deplete serum, the monolayer of cells was exposed to serum-free conditioned medium containing $^{125}I$-hPRL (50,000 cpm) in the presence of various concentration of hPRL or hPRLA for 2–3 hours at 37° C. After incubation at room temperature for 3 hours, the cells were washed with phosphate-buffered saline (P)BS) two times, and then lysed in 1 ml of 1% SDS/0.1N NaOH. The CPM in lysates were then determined. Non-specific binding was measured by adding 5 µg/ml of unlabeled hPRL in regular mouse L cell conditioned media to control nonspecific displacement.

Assay of hPRL induction of tyrosine phosphorylation of STAT5 protein. STAT proteins represent a family of proteins, having molecular masses of approximately 92–95 kDa, which have been found to be tyrosyl phosphorylated when GHR or PRLR containing cells are treated with GH or PRL, respectively. Tyrosyl phosphorylation of STAT 5 is a receptor mediated event and is thought to be an important step in ligand-induced signal transduction (Wakao et al., 1994, EMBO J. 13: 2182–2191; Kazansky et al., 1995, Mol. Endocrinol. 9:1598–1609; Waxman et al., 1995, J. Biol. Chem. 270:13262–13270). This assay was used to evaluate the ability of hPRL and hPRLA to inhibit induction of STAT 5 phosphorylation by wild type PRL.

Briefly, human breast cancer cells were plated in 12-well plates. After pre-incubation in serum-free DMEM for 2–3 hours, the cells were exposed to various concentration of hPRL and hPRLA in serum-free DMEM. The cells were incubated for 15 min at 37° C., washed once with PBS, and lysed in 300 µl lysis buffer (50 mM Tris-HCl, pH 6.8, 1% SDS, 1% β-mecaptoethanol, 0.1M DTT, 5% Sucrose, 100 uM Sodium Orthovanadate, and 0.6% bromphenol blue). Thirty microliters of cell lysates were subjected to 4–12.5% SDS-PAGE and immunoblot analysis using horse radish peroxidase (HRP)-conjugated anti-phosphotyrosine antibody PY20 and ECL reagent kit (Amersham, Ill.). Blots were then exposed to X-ray films and developed using standard procedures (Kodak, Rochester, N.Y.). This assay has been described in Chen et al., 1994, J. Biol. Chem. 269: 15892–15897; Chen et al., 1995, Endocrinol. 136:660–667; Wang et al., 1994, Proc. Natl. Acad. Sci. U.S.A. 91:1391–1395; Chen et al., 1995, Mol. Endocrinol. 9(3): 292–302; Harding et al., 1996, J. Biol. Chem. 271(12): 6708–6712.

Cell proliferation assays. hPRLA was tested for its ability to inhibit breast cancer cell proliferation in tissue culture. The human breast cancer cells were grown in corresponding culture media according to ATCC recommendations. Cells were maintained at 37° C. in a humidified atmosphere of 5% $CO_2$ in air. The assay conditions were essentially as described by Ginsburg and Vonderharr (1995, Cancer Res. 55:2591–2595). For individual growth experiments, cells were plated in 12 well culture plates at a density of approximately $2 \times 10^4$ /ml, 1 ml/ well. Cells were then allowed to attach for one day (T-47D, MCF-7, HTB19, and HTB20 cells, except for HTB 123, which is a suspension cells), then the overlying media was removed and changed to serum-free conditions with media containing ITS$^+$ (insulin-transferring-selenium-BSA-linoleic acid culture supplement; Collaborative Research Bedford, Mass.). Varying concentrations of hPRL alone or in combination with hPRLA were introduced. After an additional three days in culture, cells were harvested after brief trypsinization and counted in a cell counter.

For certain experiments, a mixed cell culture assay was used, diagramatically represented in FIG. 6. In this assay, breast cancer cells were co-cultured with expresser cells which had been transfected with nucleic acid encoding PRL or a PRL variant and expressing those recombinant proteins. By varying the number of expresser cells, the amount of PRL or PRL variant present in the mixed cell culture was increased or decreased. As shown in FIG. 6, a fixed number of breast cancer cells (T47D) were added to wells of a multi-well cell culture plate. In certain wells, which served as a control, no expresser cells were added. Then, increasing numbers of expresser cells (transfected L cells expressing either HPRL (L-PRL) or hPRLA (L-PRLA)) were added to breast cancer cell-containing wells to create mixed cultures. The same numbers of expressor cells were cultured in parallel (without T47D cells) to serve as controls. After culturing under standard conditions for a period of time, the number of cells present in the wells was counted, and the number of L cells in the corresponding control culture was subtracted. The resulting number could then be compared to the number of T47D cells in the T47D control culture to evaluate the effects of the recombinant product on breast cancer cell proliferation.

8.2. Results and Discussion

Results of radioreceptor binding assay. The results of the assay performed using T-47D and HTB123 cells along with a panel of human cancer cells are shown in FIG. 2. They demonstrate that two cell lines (T-47D and HTB123) among those tested contain minimum hGH receptor specific binding as compared to human leukemia cells, lymphoma cells and retinoblastoma cells.

Phosphorylation of STAT5 proteins. Experiments testing the abilities of hPRL and hPRLA, and combinations thereof, to induce phosphorylation of STAT5 proteins in T-47D human breast cancer cells have demonstrated that hPRLA is able to block the signal transduction induced by hPRL (FIG. 3), thereby demonstrating the antagonistic activity of PRLA. In particular, FIG. 3 shows that the induction of phosphorylation of STAT5 proteins induced by hPRL (lane 2) was absent in the presence of hPRLA only (lane 3), is partially eliminated when equal amounts of hPRL and hPRLA were present (lane 4), and is undetectable when there was an excess of hPRLA (lane 5).

Cell proliferation assays. Cell proliferation assay results from experiments in which T-47D cells were exposed to either hGH or hPRL are shown in FIG. 4. The bell shaped dose response curves suggest that similar mechanisms (i.e., one ligand leading to dimerization of receptors) are used by both GH and PRL signal transduction. Since the affinity of binding site one of the ligand is apparently much higher than the affinity at binding site two, at high concentrations of hormone, all receptors are occupied by a single ligand via the high affinity site (the "self-antagonism" phenomenon). FIGS. 5A–B compares the effects of HPRL and hPRLA (the G129R variant of human prolactin) (FIG. 5A) to the effects of estrogen and the estrogen antagonist tamoxifen (FIG. 5B). While HPRL and estrogen increased proliferation of T47D cells (relative to untreated control cultures), hPRLA and tamoxifen had a comparable inhibitory effect.

FIGS. 7 and 8 depict the results of mixed cell culture assays in which a varying number of transfected L cells (shown on the y-axis) expressing hPRL or hPRLA (the G129R variant of human prolactin) were co-cultured with T47D human breast cancer cells for 24 or 72 hours (FIG. 7) or for one, two, three or five days (FIG. 8). While hPRL resulted in an increase in T47D proliferation (relative to untreated T47D cell cultures), hPRLA inhibited proliferation by up to 100 percent.

FIGS. 9A–B compares the inhibitory effects of hPRLA in mixed cell culture on the two different human breast cancer cell lines T47D and MCF-7 (FIGS. 9A and 9B, respectively). hPRLA expressed by transfected L cells had an inhibitory effect on both cell lines, but the effect was greater on T47D cells, probably because there are a greater number of prolactin receptors on T47D cells relative to MCF-7 cells (Shiu et al., 1979, Cancer Res. 39:4381–4386); Ormandy et al., 1997, J. Clin. Endocrinol. Metab. 82:3692–3699).

9. EXAMPLE

Cloning of the Prolactin Receptor

HPRL-BP cDNA was cloned using reverse transcription (RT) followed by the polymerase chain reaction (PCR). The hPRL-BP antisense primer was designed at a NcoI restriction enzyme cutting site which is located 66 bases from the putative transmembrane domain and a stop codon (TGA) was incorporated (5'GCACTTCAGTATCCATGGTCTGGT 3')(SEQ ID NO: 36). The sense primer was designed including translational start codon ATG (5'AGAAGGCAGC-CAACATGAAG 3') (SEQ ID NO: 37). RT/PGR was carried out by using a kit from Perkin-Elmer Cetus, Inc. (Norwalk, Conn.). The nucleotide sequence hPRL-BP was determined by the dideoxy chain-termination method using modified T7 DNA polymerase (Sequenase, United States Biochemical).

10 EXAMPLE

Inhibitory Effects of a Prolactin Antagonist and its Synergistic Action in Conjunction with Tamoxifen The subsection below describes data derived from cell proliferation assays demonstrating that a prolactin variant, when added together with an anti-estrogen agent, induces a synergistic inhibitory effect on cell proliferation.

10.1. Materials and Methods

RT-PCR. The RT-PCR technique was used to clone hPRL cDNA. Human pituitary mRNA was purchased from Clontech Laboratory, Inc. (Palo Alto, Calif. 94303). A RT-PCR kit was from Perkin-Elmer, Inc. (Norwalk, Conn.). The hPRL antisense primer (for the RT reaction) was designed 2 bases from the stop codon (in bold) of hPRL cDNA (5'GCT-TAGCAGTTGTTGTTGTG 3')(SEQ ID NO: 33) and the sense primer was designed from the translational start codon ATG (5'ATGAACATCAAAGGAT 3')(SEQ ID NO: 34). The RT-PCR reaction was carried out following the manufacturer's recommendation. The PCR product was then cloned into an expression vector pcDNA3.1 from Invitrogen Corp. (Carlsbad, Calif.). The expression of hPRL cDNA was controlled by the human immediate-early cytomegalovirus (CMV) enhancer/promoter and a polyadenylation signal and transcription termination sequence from the bovine GH gene. This vector also contains a neomycin gene that allows for selection of neomycin resistant mammalian cells (FIG. 1B).

Rational Design of Hprl-G129R. The amino acid sequences of all known PRLs in the third α-helical region and aligned them with GH sequences. It is clear that Gly 129 of hPRL is invariable among PRLs and corresponds to hGH 120 suggesting a potentially important role in its function. We, therefore, decided to make a single amino acid substitution mutation at Gly 129 of hPRL (hPRL-G129R). We have used a similar approach to that which we have successfully previously used in the discovery of hGH antagonists, in hope of producing a hPRLR specific antagonist (FIG. 11).

Oligonucleotide Directed Mutagenesis hPRL-G129R cDNA was generated using PCR mutagenesis protocol. Oligonucleotides containing the desired mutation (5'CT-TCTAGAGCGCATGGAGCTCATA 3') (SEQ ID NO: 38); and (5'CCCTCTAGACTCGAGCGGCCGCC3')(SEQ ID NO: 39) were synthesized by National Biosciences, Inc. (Plymouth, Minn.). The codon for 129 Arg is in bold and the restriction site XbaI is underlined. The PCR product was digested with XbaI and ligated back into the previously described vector (FIG. 1B). The mutation was then confirmed by DNA nucleotide sequencing.

Cell Lines. Two human breast cancer cell lines (T47-D and MCF-7) and a mouse L fibroblast cell line were acquired from ATCC. Both human breast cancer cell lines have been characterized as estrogen receptor (ER) positive and PRLR positive cell lines (Ormandy, C. J., et al., 1997, J. Clin. Endocrinol. Metabo 82:3692–99). Cells were grown routinely as a monolayer culture in Dulbecco's Modified Eagle's medium (DMEM) for MCF-7 and L cells and RPMI-1640 medium was used for T47-D after supplement with 10% fetal calf serum that was treated with dextran-coated charcoal (DCC-FCS). Media for human breast cancer cells were used without phenol red (to avoid its potential estrogen-like activities). Cell cultures were maintained at 37° C. in a humidified atmosphere with 5% $CO_2$ and passed twice a week.

Expression and Production of hPRL and bPRL-G129R Proteins Mouse L cell transfection and stable cell selection were performed as previously described with minor modifications (Zhou, Y. et al., 1996, Gene 177:257–129; Sun, X. Z. et al., 1997, J. Steroid Biochem. Mol. Biol. 63:29–36). Briefly, cells were plated in a 6-well plate and cultured until the culture was 50% confluent. On the day of transfection, cells were washed once with serum free media and cultured in 1 ml serum free media containing 1 μg of pcDNA3-hPRL or pcDNA3-hPRL-G129R and 10 μl LipofectAmine (GibcoBRL) for 5 h. Two milliliters of growth medium were added to the DNA/lipofectAmine solution and incubation continued. After 18–24 hours of incubation, fresh growth medium was used to replace the medium containing DNA/lipofectAmine mixture. At 72 hours after transfection, cells were diluted 1:10 and passed into the selective medium (400 μg/ml G418) to select for neo gene expression. Individual colonies were isolated and expanded. The expression levels of the individual cell lines were determined by using an immunoradiometric assay (IRMA) kit from Diagnostic Products Corp. (Los Angeles, Calif.). The cell lines with high expression levels were expanded.

Conditioned media containing hPRL and hPRL-G129R was prepared as follows. Stable cells were plated in T-150 culture flasks at 85 to 90% confluency. The growth medium were then replaced with 50 ml of RPMI-1640 containing 1% DCC-FCS and collected every other day for three times. The collected media were then pooled and filtered through a 0.2 μm filter unit to remove cell debris and stored at −20° C. until use. The concentration of hPRL or hPRL-G129R was determined by hPRL IRMA. Each batch product was further verified using a Western blot analysis protocol (Fernandex, E. et al., 1990, Anal. Biochem. 191:268–271). We have used this protocol in hGH analog studies including hGH antagonist for in vitro studies (Chen, W. Y. et al., 1994, J. Biol. Chem. 269:15892–15897).

Tyrosine Phosphorylation of STAT Proteins in T47-D cells. This assay is designed to examine the effects of HPRL and hPRL-G129R on signal transduction using T47-D cells as model target cells. Briefly, T47-D cells were plated in 12-well plates. After pre-incubation in serum-free medium for 2–3 hours, cells were exposed to various concentrations of hPRL or hPRL-G129R or a combination of hPRL and hPRL-G129R in serum-free medium. The cells were incubated for 15 min at 37° C., washed once with PBS, and lysed in 200 µl lysis buffer (50 mM Tris-HCl, pH 6.8, 1% SDS, 1% β-mecaptoethanol, 0.1M DTT, 5% sucrose, 100 µM sodium orthovanadate, and 0.6% bromophenol blue). Thirty microliters of cell lysate are then subjected to 4–12.5% SDS-PAGE using the Bio-Rad Protein II system. After electrophoresis, the gels were transferred to a Hybond-ECL membrane (Amersham, Ill.) at 100 volts constant voltage for 2 hrs. Blots were incubated in a blocking solution of 4% BSA (Boehringer Mannheim, Ind.) in rinsing buffer (10 mM Tris-HCl pH 7.5, 75 mM NaCl, 0.1% Tween 20, 1 mM EDTA) for 2 hrs and subsequently washed twice with rinsing buffer for 15 min. Blots were incubated with horseradish peroxidase (HRP)-conjugated antiphosphotyrosine antibody PY20 (Amersham, Ill.) at a concentration of 0.1 µg/ml in the blocking solution for 1 hr. After incubation, blots were washed with rinsing buffer (15 min. each for 2 times) and developed with an ECL reagent kit according to manufacturer's suggestions (Amersham, Ill.). Blots were then exposed to X-ray film and developed using standard procedures (Kodak, Rochester, N.Y.).

HPRLG129R Conditioned Media. The assay conditions were modified from that described by Ginsburg and Vonderharr (1995, Cancer Res. 55:2591–2595). T47-D cells were trypsinized and passed into 96 well plates in RPMI-1640 media containing 1% DCC-FCS in a volume of 100 µl/well. The optimal cell number/well for each cell line was predetermined after titration assay. For T47-D cells, 15,000 cells/well were plated. The cells were allowed to settle and adhere overnight (12–18 hours) and subsequently various concentrations of either hPRL, hRPL-G129R, E2 or 4-OH-Tamoxifen in a total volume of 100 µl of culture media were added. Purified hPRL (kindly provided by Dr. Parlow, National Hormone & Pituitary Program, NIH) was used as a positive control for hPRL produced from stable L cells. Cells were incubated for an additional 96 hours at 37° C. in a humidified 5% $CO_2$ incubator. After incubation, MTS-PMS solution (Cell Titer 96 Aqueous kit, Promega Corp.) was added to each well, following the manufacturer's instructions. Plates were read at 490 nm using a BIO-RAD benchmark microplate reader. The experiments were carried out in triplicates and repeated three to six times for each cell line.

10.2. Results

Cloning and Mutagenesis of hPRL hPRL cDNA was cloned from human pituitary mRNA using RT-PCR technique. The size of the corresponding PCR product was 663 base pairs in length and it was cloned into the pcDNA 3.1 expression vector. The nucleotide sequence of hPRL was determined by the dideoxy chain-termination method using an automatic sequencer (PE Applied Biosystems, Foster City, Calif.). The hPRL cDNA sequence was found to be identical to that reported in GenBank except for one base difference that results in a silent mutation at codon 21 (CTG→CTC). HPRL-G129R cDNA was also generated by PCR and sequenced.

Expression of hPRL and hPRL-G129R Mouse L cell were stably transfected with either hPRL or hPRL-G129R cDNAs and neo-resistant clones were selected and expanded. Conditioned media were collected and tested for expression by use of an RIMA kit. hPRL and hPRL-G129R stable mouse L cell lines were generated that produced hPRL and hPRL-G129R in a quantity of approximately ~1 mg/L/24 h/million cells (FIG. 12).

Inhibition of Tyrosine Phosphorylation of the STAT Protein by hPRL-G129R STAT proteins represent a family of proteins with a molecular mass of approximately 92–95 kDa. The inhibitory effects of GH antagonist can be assayed by measuring the levels of inhibition of tyrosine phosphorylation of STAT protein (Chen et al., 1994, J. Biol. Chem. 269:15892; Wang et al., Proc. Natl. Acad. Sci. USA 91:1391–1395; Silva 1993, Endocrinology 133:2307–2312). Using such an assay, the GH antagonist hGH-G120R, was demonstrated to inhibit GH induction of STAT protein phosphorylation in a dose dependent manner.

The results using hPRL and hPRL-G129R on T47-D human breast cancer cells have demonstrated that hPRL-G129R was not active in stimulating STAT protein phosphorylation. However, when hPRL-G129R was added together with hPRL, it was able to block the signal transduction induced by hPRL in a dose dependent manner (FIG. 13) suggesting that it is functioning as a hPRL antagonist. At a 5:1 ratio, hPRL-G129R completely inhibited STAT protein phosphorylation induced by hPRL.

Human Breast Cancer Cell Proliferation Assays. Human PRL and hPRL-G129R were tested further for their ability to stimulate/inhibit breast cancer cell proliferation in cell culture. Light microscopic examination of breast cancer cell proliferation after hPRL, hPRL-G129R, E2 and 4-OH-Tamoxifen is shown in FIGS. 14A–E. It is clear that there is a significant difference in cell density between hPRL (15B), hPRL-G129R(15C) and E2 (15D), 4-OH-Tamoxifen (15E) treated cells. It is also noteworthy to point out that the overall cell condition of hPRL-G129R treated cells was not as healthy under light microscopy examination.

96 well cell proliferation assay results are shown in FIGS. 15–18. hPRL stimulated T47-D proliferation in a dose dependent manner. The maximum stimulation of hPRL (250 ng/ml) was approximately 20% over basal levels after a single dose/ four-day incubation. However, when hPRL and E2 were applied simultaneously, a synergistic effect was observed. The maximum response of hPRL (100 ng/ml) in the presence of 10 nM of E2 was more than tripled as compared to hPRL alone (FIG. 15).

hPRL-G129R, on the other hand, exhibited dose dependent inhibitory effects on cell proliferation (FIG. 16A). It is noteworthy to point out that the inhibitory effect of hPRL-G129R (150 ng/ml) was more potent than the maximal 500 nM dose of 4-OH-Tamoxifen in the assay system (FIG. 16B). The maximum inhibition of a single dose of 4-OH-Tamoxifen (500 nM) is approximately 15% of control (FIG. 16B) whereas the maximum inhibition by a single dose of hPRL-G129R resulted in 25% of control (FIG. 16A). hPRL-G129R was also able to competitively inhibit HPRL induced cell proliferation. At a 1:1 molar ratio, hPRL-G129R was able to stop the stimulatory effect of hPRL and at 2:1 molar ratio, it inhibited cell proliferation (FIG. 17). More importantly, when hPRL-G129R was applied together with 4-OH-Tamoxifen, the inhibitory effects were doubled as compared to either the maximum dose of hPRL-G129R or 4-OH-Tamoxifen (FIG. 18). For example, 100 nM of 4-OH-Tamoxifen resulted in a 15% inhibition, yet, in the presence of 100 ng/ml of hPRL-G129R the inhibitory effect resulted in approximately 32% of control.

Co-culture Experiments Stable mouse L cell lines grow at a similar rate as do regular L cells regardless of whether they are producing either hPRL or hPRL-G129R due to the fact that mouse L cells possess non-detectable PRLR (Chen, 1994, J. Biol. Chem. 269:15892–15897). The co-culture experimental set-up provides a sustained presence of biologically active hPRL-G129R, thereby resulting in a maximal response in these tumor cells.

Both human cancer cell lines after co-culture with L-G129R cells demonstrated dose dependent growth inhibition (FIGS. 19A–B). The responses were rather dramatic as compared to conditioned media experiments. Complete inhibition of cell proliferation was achieved in both cell lines. It is noteworthy that the response pattern of MCF-7 cells was shifted to the right as compared to that of T47-D cells, i.e. it required more hPRL-G129R to elicit the same inhibitory effects. These results can be explained by the fact that the total hPRLR number on MCF-7 cells is much less than that found on T47-D cells (Ormandy et al., Genes Dev. 15:167–178; Shih, 1981, In: Hormones and Breast Cancer, Cold Spring harbor Laboratory, Pike, Siiteri, and Walsh (eds) pp 185–194).

11. EXAMPLE

Human Prolactin Receptor Antagonist G129R Induces Apoptosis in Multiple Human Breast Cancer Cell Lines and Prostate Cancer Cells

11.1. Materials and Methods

Cell Lines. The human breast cancer cell lines MDA-MB-134, T-47D, BT-474 and MCF-7 were obtained from ATCC. These breast cancer cell lines were chosen based on their PRLR levels. The cell line MDA-MB-134 has the highest PRLR level followed by T-47D, BT-474, MCF-7 in decreasing order of PRLR levels (Ormundy, J Clinical Endocrinology and Metabolism 82:3692–3699).

Cell Culture. T-47D cells obtained from ATCC were grown in RPMI 1640 (phenol red free), supplemented with 10% FBS (GIBCO BRL). BT-474 cells were grown in RPMI 1640 medium (phenol red free) supplemented with 10% FBS and ATCC recommended supplements. MCF-7 cells were grown in DMEM medium (phenol red free), supplemented with 10% FBS. The cells were grown at 37° C. in a humid atmosphere in the presence of 5% $CO_2$. The MDA-MB-134 cells were grown in Leibovitz's L-15 medium supplemented with 20% FBS and grown in $CO_2$ free atmosphere. The breast cancer cells were trypsinized (0.02% Trypsin—EDTA) and grown in their respective media (phenol red free) supplemented with 10% CSS (Charcoal stripped serum) for a week. Subsequently the cells were trypsinized again and plated onto an 8 chambered slide system (Lab Tek II) at a confluence of 60–70% per chamber. The next day treatments were performed on the breast cancer cells using their respective media(phenol red free), supplemented with 1% CSS. The MDA-MB-134 VI cells were grown in phenol red containing medium, but with the same serum conditions as the other breast cancer cells.

Terminal deoxynucleotidly transferase mediated dUTP nick end labeling (TUNEL) assay. Nicks of the fragmented DNA are labeled at their 3-OH ends. The fluorescein-labeled dUTP is incorporated at the 3-OH ends by using the enzyme terminal deoxynucleotidyl transferase. After the assigned period of treatment the chambers were dismantled as per the manufacturer's instructions and the TUNEL assay (Apoptosis detection system, Fluorescein- Promega) was performed as per the manufacturer's instructions. The slide was examined under a FITC filter using an Olympus IX 70 microscope system.

11.2. Results

Apoptosis (programmed cell death) is one of the central physiological mechanisms that regulates the timely and orderly death of cells (Stellar, H., 1995, Science 267:1445). The biochemical hallmark of apoptosis is internucleosomal DNA cleavage (Wyllu, 1980, Nature 284:555; Roy et al., 1992, Exp. Cell Res. 200:416–424; Wyllu, 1980, Int. Rev. Cytol. 68:251–306) and it can be detected by the TUNEL assay or by conventional gel electrophoresis (Chen, 1996, J. Cell. Biochem. 61:9–17). Cancer is a disease in which the malignant cells have a decreased ability to undergo apoptosis in response to at least some physiological stimuli (Hoffman et al., 1994, Oncogene 9:1807). Drugs that can induce cancer cells to undergo apoptosis could prove to be effective in cancer therapy.

Figure 20A:
Figure 20B:
Figure 20C:
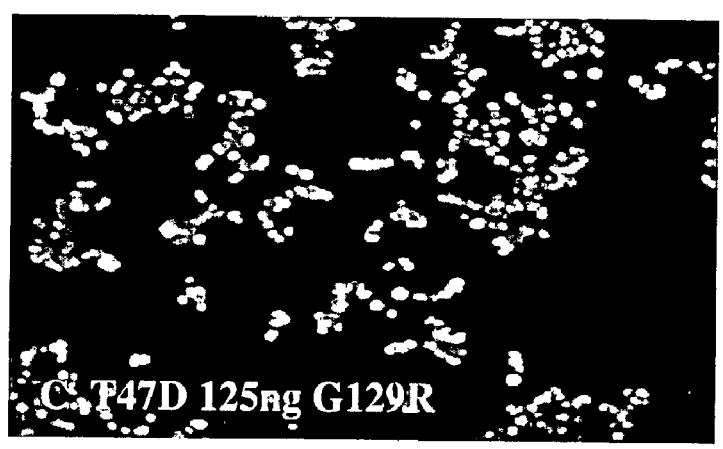
Figure 20D:
Figure 20E:
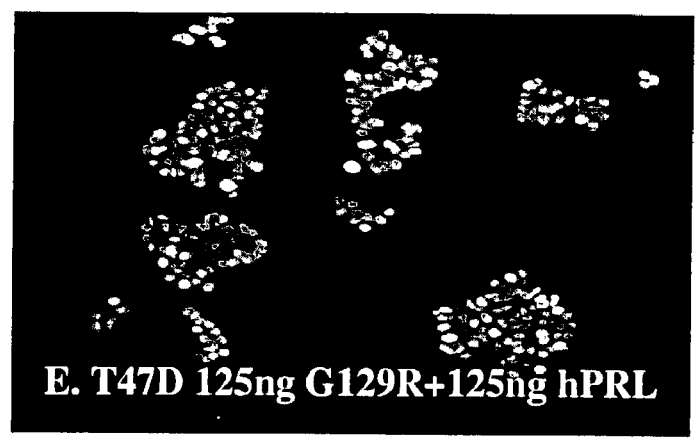
Figure 20F:
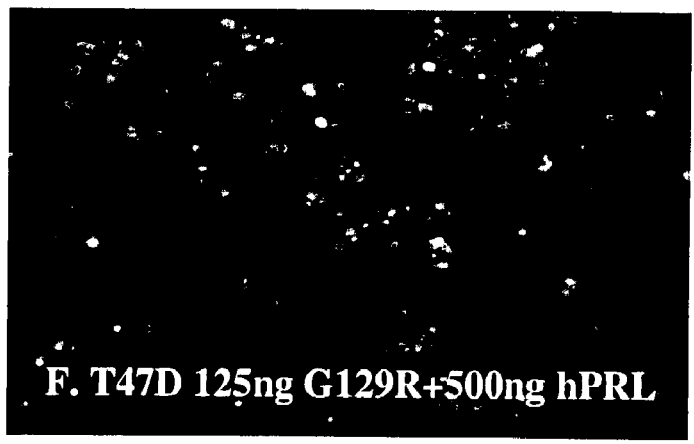
Figure 21A:
Figure 21B:
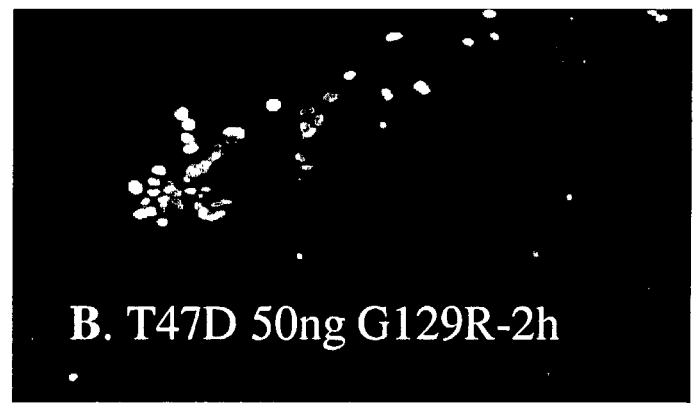
Figure 21C:
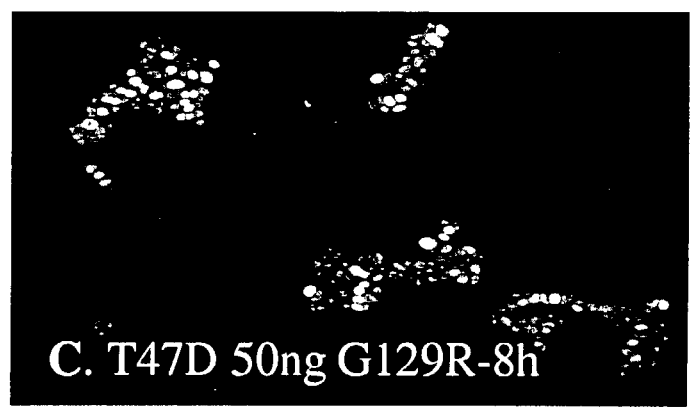
Figure 21D:
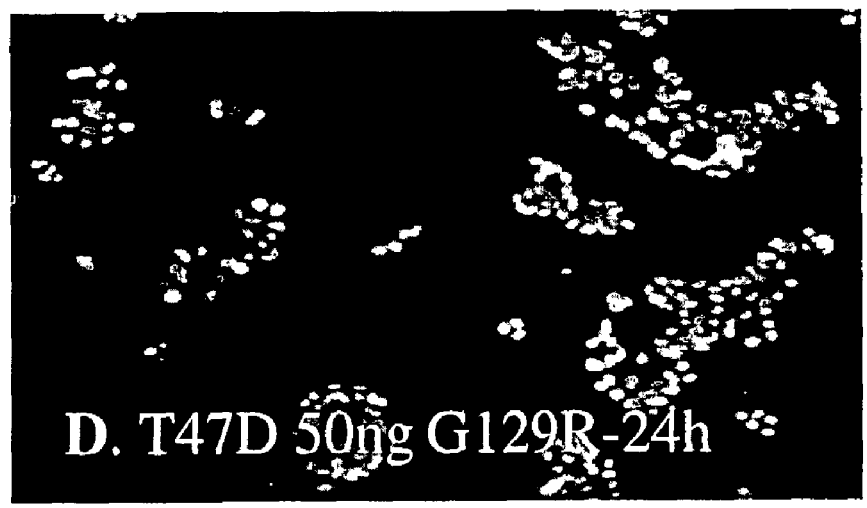
Figure 21E:
Figure 22B:
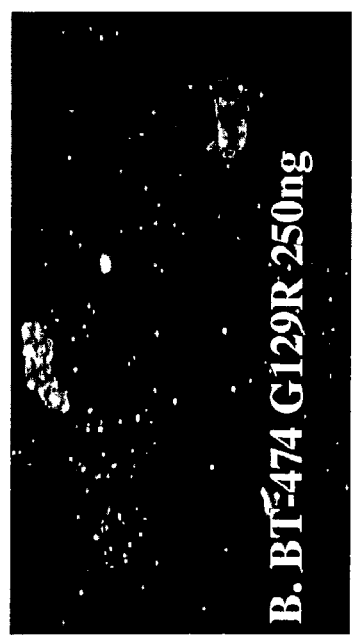
Figure 22D:
Figure 22A:
Figure 22C:
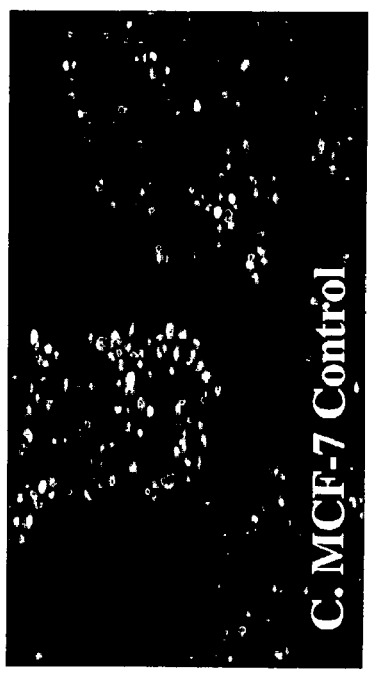
Figure 23A:
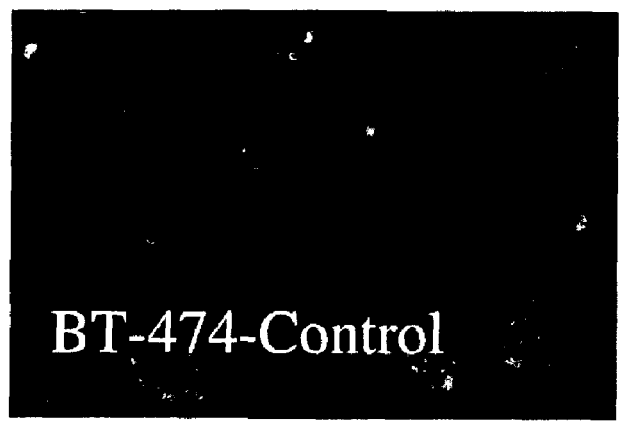
Figure 23B:
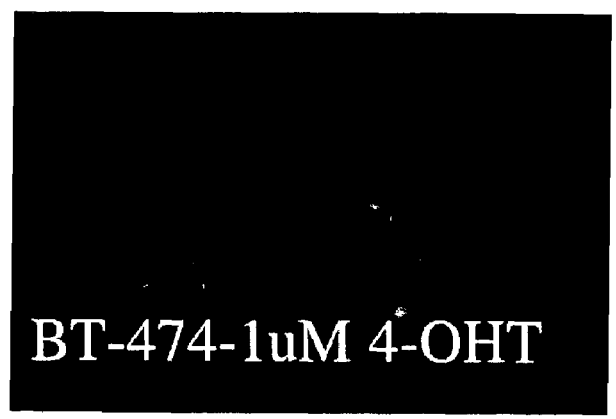
Figure 23C:
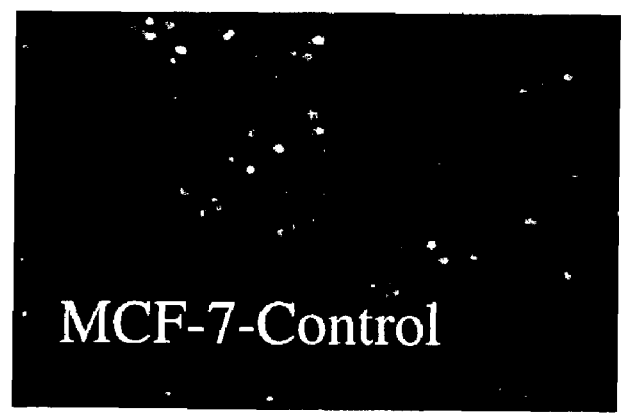
Figure 23D:
Figure 23E:
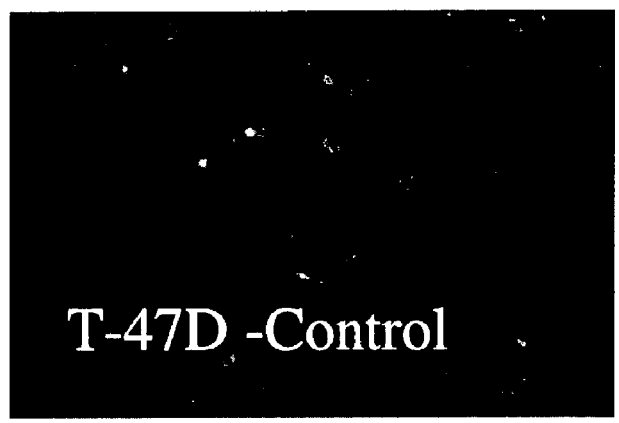
Figure 23F:
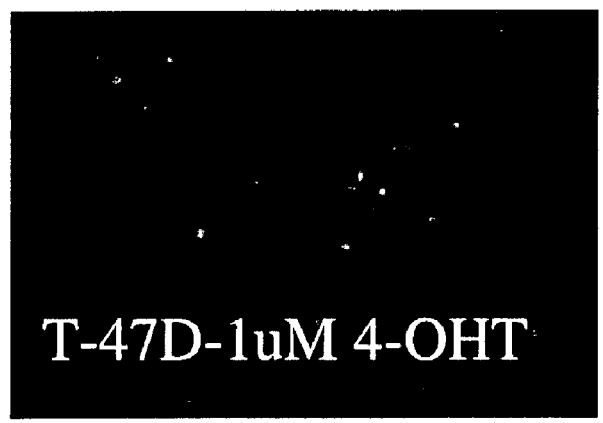

As demonstrated herein, the PRLR antagonist G129R is able to induce apoptosis as detected by DNA fragmentation in multiple human breast cancer cell lines. FIGS. 20A–F shows that G129R induced apoptosis in a dose dependent manner after 24 h treatment and that apoptosis occurs even at physiological concentrations (50 ng/ml, FIG. 20C). In order to demonstrate the specificity of G129R to the PRLR, hPRL (kindly provided by Dr. Parlow from NIH) and G129R were simultaneously used to treat the cells at a 1:1 and 1:4 ratio (FIGS. 20G–H). It is clear that G129R was able to compete with hPRL at a ratio of 1:1 (FIG. 20E) and is able to competitively reverse the DNA fragmentation induced by G129R at a 4:1 ratio (FIG. 20F). The mitogen rescue effect of hPRL is yet another indication that G129 R induces apoptosis. The same results were obtained using BT-474 cells.

DNA fragmentation in breast cancer cells is apparent even after 2 hours of treatment by G129R at a concentration of 50 ng/ml (FIGS. 21A-D). In previous studies it was shown that 4-OH-Tamoxifen synergistically inhibited the proliferation of breast cancer cells along with G129R. Therefore, 4-OH-Tamoxifen was included in this study to verify that 4-OH-Tamoxifen also induced apoptosis in breast cancer cells by DNA fragmentation. Surprisingly, 4-OH-Tamoxifen did not induce apoptosis in T-47D, MCF-7 or BT-474 cells at a concentration as high as 1 µM as assayed by the same protocol despite the fact that 4-OH-Tamoxifen was able to inhibit cell proliferation (FIGS. 22A–H). In contrast to 4-OH-Tamoxifen, 250 ng of G129R induced apoptosis DNA fragmentation in all four PRLR positive breast cancer cell lines after 24 hours treatment (FIGS. 23A–F).

In addition, the effect of hPRL-G129R on Caspase-3 activation was assayed in T-47D cells using an ApopAlert CPP32/Caspase-3 assay kit (Clontech, Palo Alto, Calif.) as presented in FIG. 24. T-47D cells were treated with 250 ng/ml of hPRL-G129R for 2 h. The assay was performed in the presence of DEVD-CHO (caspase-3 inhibitor) to demonstrate that the Caspase-3 induction by hPRL-G129R is a specific event.

The data described above indicates that breast cancer cells are adapted to utilize prolactin as a major growth factor and undergo apoptosis when deprived of it by the competitive binding of G129R to the PRLR leading to blockage of the PRL growth signal. Thus, the continued mitogenic signal provided by HPRL may override existing apoptotic signals within breast cancer cells permitting the delayed apoptosis process to proceed. The data presented herein, indicates that the prolactin receptor antagonist G129R can be used in endocrine therapy in conjunction with tamoxifen, or by itself, in the treatment of breast cancer.

In addition, two prostate cancer cells, underwent apoptosis in response to treatment with 250 ng hPRL-G129R for 24 hours as detected using TUNEL assay (FIG. 25). The samples were in duplicate and each sample constituted about 2 million cells The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Various publications are cited herein, the contents of which are hereby incorporated, by reference, in their entireties.

We claim:

1. A method of inhibiting in a subject the proliferation of a breast cancer cell which expresses a prolactin receptor, comprising exposing the cell to an effective concentration of a variant of human prolactin wherein the variant consists of human prolactin and has the substitution of the glycine at position 129.

2. The method of claim 1, wherein the substitution of the glycine at position 129 is with arginine.

3. The method of claim 1, which is used in the treatment of breast cancer in a subject in need of such treatment.

4. The method of claim 3, wherein the variant of human prolactin is administered to the subject as part of a combined therapy regimen.

5. The method of claim 4, wherein the combined therapy regimen comprises administration of an anti-estrogen agent.

6. The method of claim 5, wherein the anti-estrogen agent is tamoxifen.

7. The method of claim 2, which is used in the treatment of breast cancer in a subject in need of such treatment.

8. The method of claim 7, wherein the variant of human prolactin is administered to the subject as part of a combined therapy regimen.

9. The method of claim 8, wherein the combined therapy regimen comprises administration of an anti-estrogen agent.

10. The method of claim 9, wherein the anti-estrogen agent is tamoxifen.

11. The method of claim 1, wherein the substitution of the glycine at position 129 is with an amino acid selected from the group consisting of tryptophan, proline, leucine and lysine.

12. The method of claim 1, wherein the substitution of the glycine at position 129 is with an amino acid selected from the group consisting of valine, isoleucine, threonine, tyrosine, cysteine, methionine, arginine, histidine, phenylalanine, asparagine, glutamine, aspartic acid and glutamic acid.

13. A method of treating in a subject a breast tumor cell which expresses a prolactin receptor, comprising exposing the cell to an effective concentration of a variant of human prolactin wherein the variant consists of human prolactin and has the having a substitution of the glycine at position 129.

14. The method of claim 13, wherein the variant consists of SEQ ID NO:1 and has the substitution of the glycine at position 129.

15. The method of claim 1, wherein the variant consists of SEQ ID NO:1 and has the substitution of the glycine at position 129.

* * * * *

UNITED STATES PATENT AND TRADEMARK OFFICE
CERTIFICATE OF CORRECTION

PATENT NO. : 7,115,556 B2 Page 1 of 1
APPLICATION NO. : 10/140293
DATED : October 3, 2006
INVENTOR(S) : Wen Y. Chen et al.

It is certified that error appears in the above-identified patent and that said Letters Patent is hereby corrected as shown below:

IN THE CLAIMS

Column 65, Claim 1, line 6: Please delete "and has the substitution" and replace with -- and has a substitution -- .

Column 66, Claim 13, line 17: Please delete "and has the having a substitution" and replace with -- and has a substitution -- .

Signed and Sealed this

Eleventh Day of September, 2007

JON W. DUDAS
*Director of the United States Patent and Trademark Office*

SEQUENCE LISTING

<160> NUMBER OF SEQ ID NOS: 39

<210> SEQ ID NO 1
<211> LENGTH: 199
<212> TYPE: PRT
<213> ORGANISM: Homo sapiens

<400> SEQUENCE: 1

```
Leu Pro Ile Cys Pro Gly Gly Ala Ala Arg Cys Gln Val Thr Leu Arg
  1               5                  10                  15

Asp Leu Phe Asp Arg Ala Val Val Leu Ser His Tyr Ile His Asn Leu
             20                  25                  30

Ser Ser Glu Met Phe Ser Glu Phe Asp Lys Arg Tyr Thr His Gly Arg
         35                  40                  45

Gly Phe Ile Thr Lys Ala Ile Asn Ser Cys His Thr Ser Ser Leu Ala
     50                  55                  60

Thr Pro Glu Asp Lys Glu Gln Ala Gln Gln Met Asn Gln Lys Asp Phe
 65                  70                  75                  80

Leu Ser Leu Ile Val Ser Ile Leu Arg Ser Trp Asn Glu Pro Leu Tyr
                 85                  90                  95

His Leu Val Thr Glu Val Arg Gly Met Gln Glu Ala Pro Glu Ala Leu
            100                 105                 110

Leu Ser Lys Ala Val Glu Ile Glu Glu Gln Thr Lys Arg Leu Leu Arg
        115                 120                 125

Gly Met Glu Leu Ile Val Ser Gln Val His Pro Glu Thr Lys Glu Asn
    130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Leu Lys Cys Arg
            180                 185                 190

Ile Ile His Asn Asn Asn Cys
        195
```

<210> SEQ ID NO 2
<211> LENGTH: 197
<212> TYPE: PRT
<213> ORGANISM: Rattus sp.

<400> SEQUENCE: 2

```
Leu Pro Val Cys Ser Gly Gly Asp Cys Gln Thr Pro Leu Pro Glu Leu
  1               5                  10                  15

Phe Asp Arg Val Val Met Leu Ser His Tyr Ile His Thr Leu Tyr Thr
             20                  25                  30
```

```
Asp Met Phe Ile Glu Phe Asp Lys Gln Tyr Val Gln Asp Arg Glu Phe
         35                  40                  45

Ile Ala Lys Ala Ile Asn Asp Cys Pro Thr Ser Ser Leu Ala Thr Pro
 50                  55                  60

Glu Asp Lys Glu Gln Ala Gln Lys Val Pro Pro Glu Val Leu Leu Asn
 65                  70                  75                  80

Leu Ile Leu Ser Leu Val His Ser Trp Asn Asp Pro Leu Phe Gln Leu
                 85                  90                  95

Ile Thr Gly Leu Gly Gly Ile His Glu Ala Pro Asp Ala Ile Ile Ser
                100                 105                 110

Arg Ala Lys Glu Ile Glu Glu Gln Asn Lys Arg Leu Leu Glu Gly Ile
                115                 120                 125

Glu Lys Ile Ile Gly Gln Ala Tyr Pro Glu Ala Lys Gly Asn Glu Ile
    130                 135                 140

Tyr Leu Val Trp Ser Gln Leu Pro Ser Leu Gln Gly Val Asp Glu Glu
145                 150                 155                 160

Ser Lys Asp Leu Ala Phe Tyr Asn Asn Ile Arg Cys Leu Arg Arg Asp
                165                 170                 175

Ser His Lys Val Asp Asn Tyr Leu Lys Phe Leu Arg Cys Gln Ile Val
                180                 185                 190

His Lys Asn Asn Cys
            195

<210> SEQ ID NO 3
<211> LENGTH: 197
<212> TYPE: PRT
<213> ORGANISM: Murine sp.

<400> SEQUENCE: 3

Leu Pro Ile Cys Ser Ala Gly Asp Cys Gln Thr Ser Leu Arg Glu Leu
 1               5                  10                  15

Phe Asp Arg Val Val Ile Leu Ser His Tyr Ile His Thr Leu Tyr Thr
                 20                  25                  30

Asp Met Phe Ile Glu Phe Asp Lys Gln Tyr Val Gln Asp Arg Glu Glu
         35                  40                  45

Met Val Lys Val Ile Asn Asp Cys Pro Thr Ser Ser Leu Ala Thr Pro
 50                  55                  60

Glu Asp Lys Glu Gln Ala Leu Lys Val Pro Pro Glu Val Leu Leu Asn
 65                  70                  75                  80

Leu Ile Leu Ser Leu Val Gln Ser Ser Ser Asp Pro Leu Phe Gln Leu
                 85                  90                  95

Ile Thr Gly Val Gly Gly Ile Gln Glu Ala Pro Glu Tyr Ile Leu Ser
                100                 105                 110

Arg Ala Lys Glu Ile Glu Glu Gln Asn Lys Gln Leu Leu Glu Gly Val
                115                 120                 125

Glu Lys Ile Ile Ser Gln Ala Tyr Pro Glu Ala Lys Gly Asn Gly Ile
    130                 135                 140

Tyr Phe Val Trp Ser Gln Leu Pro Ser Leu Gln Gly Val Asp Glu Glu
145                 150                 155                 160

Ser Lys Ile Leu Ser Leu Arg Asn Thr Ile Arg Cys Leu Arg Arg Asp
                165                 170                 175

Ser His Lys Val Asp Asn Phe Leu Lys Val Leu Arg Cys Gln Ile Ala
                180                 185                 190

His Gln Asn Asn Cys
            195
```

<210> SEQ ID NO 4
<211> LENGTH: 197
<212> TYPE: PRT
<213> ORGANISM: Cricetidae sp.

<400> SEQUENCE: 4

Leu Pro Ile Cys Pro Gly Gly Asn Cys Gln Met Pro Leu Gln Glu Leu
1               5                   10                  15

Phe Asp Arg Val Ile Met Leu Ser His Tyr Ile Tyr Met Leu Ser Ala
            20                  25                  30

Asp Met Phe Ile Glu Leu Asp Lys Gln Tyr Ala Gln Asp His Glu Phe
        35                  40                  45

Ile Ala Lys Ala Ile Ser Asp Cys Pro Thr Ser Ser Leu Ala Thr Pro
    50                  55                  60

Glu Gly Lys Glu Glu Ala Gln Gln Val Pro Pro Glu Val Leu Leu Asn
65                  70                  75                  80

Leu Ile Leu Ser Leu Val His Ser Trp Asn Asp Pro Leu Phe Gln Leu
                85                  90                  95

Val Thr Glu Val Asp Gly Ile His Glu Ala Ser Asp Ala Ile Ile Ser
            100                 105                 110

Arg Ala Lys Glu Ile Gly Glu Gln Asn Lys Arg Leu Leu Glu Gly Ile
        115                 120                 125

Glu Lys Ile Leu Gly Gln Ala Tyr Pro Glu Ala Lys Gly Asn Glu Ile
    130                 135                 140

Tyr Ser Val Trp Ser Gln Phe Pro Ser Leu Gln Gly Val Asp Glu Glu
145                 150                 155                 160

Ser Arg Asp Leu Ala Ile Tyr Asn Lys Val Arg Cys Leu Arg Arg Asp
                165                 170                 175

Ser His Lys Val Asp Asn Tyr Leu Lys Leu Leu Arg Cys Arg Val Val
            180                 185                 190

His Asn Asn Asn Cys
        195

<210> SEQ ID NO 5
<211> LENGTH: 199
<212> TYPE: PRT
<213> ORGANISM: Balaenoptera sp.

<400> SEQUENCE: 5

Ile Pro Ile Cys Pro Ser Gly Ala Val Asn Cys Gln Val Ser Leu Arg
1               5                   10                  15

Asp Leu Phe Asp Arg Ala Val Ile Leu Ser His Tyr Ile His Asn Leu
            20                  25                  30

Ser Ser Glu Met Phe Asn Glu Phe Asp Lys Arg Tyr Ala Gln Gly Arg
        35                  40                  45

Gly Phe Ile Thr Lys Ala Ile Asn Ser Cys His Thr Ser Ser Leu Gln
    50                  55                  60

Thr Pro Glu Asp Lys Glu Gln Ala Gln Gln Ile His His Glu Val Leu
65                  70                  75                  80

Val Ser Leu Ile Leu Gly Val Leu Arg Ser Trp Asn Asp Pro Leu Tyr
                85                  90                  95

His Leu Val Thr Glu Val Arg Gly Met Gln Glu Ala Pro Asp Ala Ile
            100                 105                 110

Leu Ser Arg Ala Ile Gln Glu Glu Glu Asn Lys Arg Leu Leu Glu
        115                 120                 125

```
Gly Met Glu Lys Ile Val Gly Gln Val His Pro Gly Val Lys Glu Asn
        130                 135                 140

Glu Val Tyr Ser Val Trp Ser Gly Leu Pro Ser Leu Gln Met Ala Asp
145                 150                 155                 160

Glu Asp Thr Arg Leu Phe Ala Phe Tyr Asn Leu Leu His Cys Leu Arg
                165                 170                 175

Arg Asp Ser His Lys Ile Asp Ser Tyr Leu Lys Leu Leu Lys Cys Arg
                180                 185                 190

Ile Ile Tyr Asn Ser Asn Cys
                195

<210> SEQ ID NO 6
<211> LENGTH: 199
<212> TYPE: PRT
<213> ORGANISM: Mustela sp.
<220> FEATURE:
<221> NAME/KEY: MOD_RES
<222> LOCATION: (1)..(24)
<223> OTHER INFORMATION: Variable amino acid

<400> SEQUENCE: 6

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Leu Ser His Tyr Ile His Asn Leu
                 20                  25                  30

Ser Ser Glu Met Phe Asn Glu Phe Asp Lys Arg Tyr Ala Gln Gly Arg
             35                  40                  45

Gly Phe Ile Thr Lys Ala Ile Asn Ser Cys His Thr Ser Ser Leu Ser
         50                  55                  60

Thr Pro Glu Asp Lys Glu Gln Ala Gln Gln Ile His His Glu Asp Leu
 65                  70                  75                  80

Leu Asn Leu Ile Leu Arg Val Leu Arg Ser Trp Asn Asp Pro Leu Tyr
                 85                  90                  95

His Leu Val Ser Glu Val Arg Gly Met Gln Glu Ala Pro Asp Ser Ile
            100                 105                 110

Leu Ser Arg Ala Ile Glu Ile Glu Glu Gln Asn Arg Arg Leu Leu Glu
        115                 120                 125

Gly Met Glu Lys Ile Val Gly Gln Val His Pro Gly Val Arg Glu Asn
        130                 135                 140

Glu Val Tyr Ser Val Trp Ser Gly Leu Pro Ser Leu Gln Met Ala Asp
145                 150                 155                 160

Glu Asp Ser Arg Leu Phe Ala Phe Tyr Asn Leu Leu His Cys Leu Arg
                165                 170                 175

Arg Asp Ser His Lys Ile Asp Asn Tyr Leu Lys Leu Leu Lys Cys Arg
                180                 185                 190

Ile Val Tyr Asp Ser Asn Cys
                195

<210> SEQ ID NO 7
<211> LENGTH: 199
<212> TYPE: PRT
<213> ORGANISM: Capitalis sp.

<400> SEQUENCE: 7

Thr Pro Val Cys Pro Asn Gly Pro Gly Asn Cys Gln Val Ser Leu Arg
  1               5                  10                  15

Asp Leu Phe Asp Arg Ala Val Met Val Ser His Tyr Ile His Asp Leu
```

-continued

```
                20                  25                  30
Ser Ser Glu Met Phe Asn Glu Phe Asp Lys Arg Tyr Ala Gln Gly Lys
         35                  40                  45

Gly Phe Ile Thr Met Ala Ile Asn Ser Cys His Thr Ser Ser Leu Pro
     50                  55                  60

Thr Pro Glu Asp Lys Glu Gln Ala Gln Gln Thr His His Glu Val Leu
 65                  70                  75                  80

His Ser Leu Ile Leu Gly Leu Leu Arg Ser Trp Asn Asp Pro Leu Tyr
                 85                  90                  95

His Leu Val Thr Glu Val Arg Gly Met Lys Gly Ala Pro Asp Ala Ile
            100                 105                 110

Leu Ser Arg Ala Ile Glu Ile Glu Glu Glu Asn Lys Arg Leu Ile Glu
        115                 120                 125

Gly Met Glu Met Ile Phe Gly Gln Val Ile Pro Gly Ala Lys Glu Thr
    130                 135                 140

Glu Pro Tyr Pro Val Trp Ser Gly Leu Pro Ser Leu Gln Thr Lys Asp
145                 150                 155                 160

Glu Asp Ala Arg Tyr Ser Ala Phe Tyr Asn Leu Leu His Cys Leu Arg
                165                 170                 175

Arg Asp Ser Ser Lys Ile Asp Thr Tyr Leu Lys Leu Leu Asn Cys Arg
            180                 185                 190

Ile Ile Tyr Asn Asn Asn Cys
            195

<210> SEQ ID NO 8
<211> LENGTH: 199
<212> TYPE: PRT
<213> ORGANISM: Ovis sp.

<400> SEQUENCE: 8

Thr Pro Val Cys Pro Asn Gly Pro Gly Asp Cys Gln Val Ser Leu Arg
  1               5                  10                  15

Asp Leu Phe Asp Arg Ala Val Met Val Ser His Tyr Ile His Asn Leu
             20                  25                  30

Ser Ser Glu Met Glu Asn Glu Phe Asp Lys Arg Tyr Ala Gln Gly Lys
         35                  40                  45

Gly Phe Ile Thr Met Ala Ile Asn Ser Cys His Thr Ser Ser Leu Pro
     50                  55                  60

Thr Pro Glu Asp Lys Glu Gln Ala Gln Gln Thr His His Glu Val Leu
 65                  70                  75                  80

Met Ser Leu Ile Leu Gly Leu Leu Arg Ser Trp Asn Asp Pro Leu Tyr
                 85                  90                  95

His Leu Val Thr Glu Val Arg Gly Met Lys Gly Val Pro Asp Ala Ile
            100                 105                 110

Leu Ser Arg Ala Ile Glu Ile Glu Glu Glu Asn Lys Arg Leu Leu Glu
        115                 120                 125

Gly Met Glu Asn Ile Phe Gly Gln Val Ile Pro Gly Ala Lys Glu Thr
    130                 135                 140

Glu Pro Tyr Pro Val Trp Ser Gly Leu Pro Ser Leu Gln Thr Lys Asp
145                 150                 155                 160

Glu Asp Ala Arg His Ser Ala Phe Tyr Asn Leu Leu His Cys Leu Arg
                165                 170                 175

Arg Asp Ser Ser Lys Ile Asp Thr Tyr Leu Lys Leu Leu Asn Cys Arg
            180                 185                 190
```

Ile Ile Tyr Asn Asn Asn Cys
        195

<210> SEQ ID NO 9
<211> LENGTH: 199
<212> TYPE: PRT
<213> ORGANISM: Sus sp.

<400> SEQUENCE: 9

Leu Pro Glu Cys Pro Ser Gly Ala Val Asn Cys Gln Val Ser Leu Arg
 1               5                  10                  15

Asp Leu Phe Asp Arg Ala Val Ile Leu Ser His Tyr Ile His Asn Leu
            20                  25                  30

Ser Ser Glu Met Phe Asn Glu Phe Asp Lys Arg Tyr Ala Gln Gly Arg
        35                  40                  45

Gly Phe Ile Thr Lys Ala Ile Asn Ser Cys His Thr Ser Ser Leu Ser
    50                  55                  60

Thr Pro Glu Asp Lys Glu Gln Ala Gln Gln Ile His His Glu Val Leu
65                  70                  75                  80

Ile Asn Leu Ile Leu Arg Val Leu Arg Ser Trp Asn Asp Pro Leu Tyr
                85                  90                  95

His Leu Val Thr Glu Val Arg Gly Met Gln Glu Ala Pro Glu Ala Ile
            100                 105                 110

Leu Ser Arg Ala Ile Gln Glu Glu Glu Asn Lys Arg Leu Leu Glu
        115                 120                 125

Gly Met Glu Lys Ile Val Gly Gln Val His Pro Gly Ile Lys Glu Asn
    130                 135                 140

Glu Val Tyr Ser Val Trp Ser Gly Leu Pro Ser Leu Gln Met Ala Asp
145                 150                 155                 160

Glu Asp Thr Arg Leu Phe Ala Phe Tyr Asn Leu Leu His Cys Leu Arg
                165                 170                 175

Arg Asp Ser His Lys Ile Asp Asn Tyr Leu Lys Leu Leu Lys Cys Arg
            180                 185                 190

Ile Ile Tyr Asn Ser Asn Cys
        195

<210> SEQ ID NO 10
<211> LENGTH: 199
<212> TYPE: PRT
<213> ORGANISM: Camelus sp.

<400> SEQUENCE: 10

Leu Pro Ile Cys Pro Ser Gly Ala Val Asn Val Gln Val Ser Leu Arg
 1               5                  10                  15

Asp Leu Phe Asp Arg Ala Val Ile Leu Ser His Tyr Ile His Asn Leu
            20                  25                  30

Ser Ser Glu Met Phe Asn Glu Phe Asp Lys Arg Tyr Ala Gln Gly Arg
        35                  40                  45

Gly Phe Met Thr Lys Ala Ile Asn Ser Cys His Thr Ser Ser Leu Ser
    50                  55                  60

Thr Pro Glu Asp Lys Glu Gln Ala Gln Gln Ile His His Glu Asp Leu
65                  70                  75                  80

Leu Asn Leu Val Leu Arg Val Leu Arg Ser Trp Asn Asp Pro Leu Tyr
                85                  90                  95

His Leu Val Thr Glu Val Arg Gly Met Gln Glu Ala Pro Asp Ala Ile
            100                 105                 110

```
Leu Ser Arg Ala Ile Glu Ile Glu Glu Gln Asn Lys Arg Leu Leu Glu
            115                 120                 125

Gly Met Glu Lys Ile Val Gly Gln Val His Pro Gly Val Lys Glu Asn
130                 135                 140

Glu Ile Tyr Ser Val Trp Ser Gly Leu Pro Ser Leu Gln Met Ala Asp
145                 150                 155                 160

Glu Asp Thr Arg Leu Phe Ala Phe Tyr Asn Leu Leu His Cys Leu Arg
                165                 170                 175

Arg Asp Ser His Lys Ile Asp Asn Tyr Leu Lys Leu Leu Lys Cys Arg
                180                 185                 190

Ile Ile Tyr Asp Ser Asn Cys
            195

<210> SEQ ID NO 11
<211> LENGTH: 199
<212> TYPE: PRT
<213> ORGANISM: Equus sp.

<400> SEQUENCE: 11

Leu Pro Ile Cys Pro Ser Gly Ala Val Asn Cys Gln Val Ser Leu Arg
  1               5                  10                  15

Glu Leu Phe Asp Arg Ala Val Ile Leu Ser His Tyr Ile His Asn Leu
                 20                  25                  30

Ser Ser Glu Met Phe Asn Glu Phe Asp Lys Arg Tyr Ala Gln Gly Arg
            35                  40                  45

Gly Phe Val Thr Lys Ala Ile Asn Ser Cys His Thr Ser Ser Leu Ser
     50                  55                  60

Thr Pro Glu Asp Lys Glu Gln Ala Gln Gln Ile His His Glu Asp Leu
 65                  70                  75                  80

Leu Asn Leu Ile Leu Arg Val Leu Lys Ser Trp Asn Asp Pro Leu Tyr
                 85                  90                  95

His Leu Val Ser Glu Val Arg Gly Met Gln Glu Ala Pro Glu Ala Ile
                100                 105                 110

Leu Ser Lys Ala Ile Glu Ile Glu Glu Gln Asn Arg Arg Leu Leu Glu
            115                 120                 125

Gly Met Glu Lys Ile Val Gly Gln Val Gln Pro Arg Ile Lys Glu Asn
130                 135                 140

Glu Val Tyr Ser Val Trp Ser Gly Leu Pro Ser Leu Gln Met Ala Asp
145                 150                 155                 160

Glu Asp Ser Arg Leu Phe Ala Phe Tyr Asn Leu Leu His Cys Leu Arg
                165                 170                 175

Arg Asp Ser His Lys Ile Asp Asn Tyr Leu Lys Leu Leu Lys Cys Arg
                180                 185                 190

Ile Val Tyr Asn Ser Asn Cys
            195

<210> SEQ ID NO 12
<211> LENGTH: 199
<212> TYPE: PRT
<213> ORGANISM: Elephas maximus

<400> SEQUENCE: 12

Ile Pro Val Cys Pro Arg Gly Ser Val Arg Cys Gln Val Ser Leu Pro
  1               5                  10                  15

Asp Leu Phe Asp Arg Ala Val Met Leu Ser His Tyr Ile His Ser Leu
                 20                  25                  30
```

```
Ser Ser Asp Met Phe His Glu Phe Asn Lys Gln Tyr Ala Leu Gly Arg
            35                  40                  45

Gly Phe Ile Pro Arg Ala Ile Asn Ser Cys His Thr Ser Ser Ile Ser
        50                  55                  60

Thr Pro Glu Asp Lys Asp Gln Ala Gln Gln Thr His His Glu Val Leu
65                  70                  75                  80

Met Asp Leu Ile Leu Gly Leu Leu Arg Ser Trp Asn Asp Pro Leu Asp
                85                  90                  95

His Leu Ala Ser Glu Val His Ser Leu Pro Lys Ala Pro Ser Ala Leu
            100                 105                 110

Leu Thr Lys Ala Thr Glu Val Lys Glu Glu Asn Gln Arg Leu Leu Glu
        115                 120                 125

Gly Ile Glu Lys Ile Val Asp Gln Val His Pro Gly Ala Lys Glu Asn
130                 135                 140

Lys Ala Tyr Ser Val Trp Ser Gly Leu Pro Ser Leu Gln Thr Thr Asp
145                 150                 155                 160

Glu Asp Ala Arg Leu Phe Ala Phe Tyr Asn Leu Phe Arg Cys Leu Arg
                165                 170                 175

Arg Asp Ser His Lys Ile Asp Ser Tyr Leu Lys Leu Leu Lys Cys Arg
            180                 185                 190

Ile Val Tyr Asn Asn Asn Cys
            195

<210> SEQ ID NO 13
<211> LENGTH: 199
<212> TYPE: PRT
<213> ORGANISM: Unknown Organism
<220> FEATURE:
<223> OTHER INFORMATION: Description of Unknown Organism: Ancestral
      mammal

<400> SEQUENCE: 13

Leu Pro Ile Cys Pro Ser Gly Ala Val Asn Cys Gln Val Ser Leu Arg
1               5                   10                  15

Asp Leu Phe Asp Arg Ala Val Ile Leu Ser His Tyr Ile His Asn Leu
            20                  25                  30

Ser Ser Glu Met Phe Asn Glu Phe Asp Lys Arg Tyr Ala Gln Gly Arg
        35                  40                  45

Gly Phe Ile Thr Lys Ala Ile Asn Ser Cys His Thr Ser Ser Leu Ser
    50                  55                  60

Thr Pro Glu Asp Lys Glu Gln Ala Gln Gln Ile His His Glu Val Leu
65                  70                  75                  80

Leu Asn Leu Ile Leu Gly Leu Leu Arg Ser Trp Asn Asp Pro Leu Tyr
                85                  90                  95

His Leu Val Thr Glu Val Arg Gly Met Gln Glu Ala Pro Glu Ala Ile
            100                 105                 110

Leu Ser Arg Ala Ile Glu Ile Glu Glu Asn Lys Arg Leu Leu Glu
        115                 120                 125

Gly Met Glu Lys Ile Val Gly Gln Val His Pro Gly Ala Lys Glu Asn
130                 135                 140

Glu Ile Tyr Ser Val Trp Ser Gly Leu Pro Ser Leu Gln Met Ala Asp
145                 150                 155                 160

Glu Asp Ser Arg Leu Phe Ala Phe Tyr Asn Leu Leu His Cys Leu Arg
                165                 170                 175

Arg Asp Ser His Lys Ile Asp Asn Tyr Leu Lys Leu Leu Lys Cys Arg
            180                 185                 190
```

Ile Ile Tyr Asn Asn Asn Cys
        195

<210> SEQ ID NO 14
<211> LENGTH: 199
<212> TYPE: PRT
<213> ORGANISM: Gallus sp.

<400> SEQUENCE: 14

Leu Pro Ile Cys Pro Ile Gly Ser Val Asn Cys Gln Val Ser Leu Gly
 1               5                  10                  15

Glu Leu Phe Asp Arg Ala Val Lys Leu Ser His Tyr Ile His Tyr Leu
             20                  25                  30

Ser Ser Glu Ile Phe Asn Glu Phe Asp Glu Arg Tyr Ala Gln Gly Arg
         35                  40                  45

Gly Phe Ile Thr Lys Ala Val Asn Gly Cys His Thr Ser Ser Leu Thr
     50                  55                  60

Thr Pro Glu Asp Lys Glu Gln Ala Gln Gln Ile His His Glu Asp Leu
 65                  70                  75                  80

Leu Asn Leu Val Val Gly Val Leu Arg Ser Trp Asn Asp Pro Leu Leu
                 85                  90                  95

His Leu Ala Ser Glu Val Gln Arg Ile Lys Glu Ala Pro Asp Thr Ile
            100                 105                 110

Leu Trp Lys Ala Val Glu Ile Glu Glu Gln Asn Lys Arg Leu Leu Glu
        115                 120                 125

Gly Met Glu Lys Ile Val Gly Arg Val His Ser Gly His Ala Gly Asn
    130                 135                 140

Glu Ile Tyr Ser His Ser Asp Gly Leu Pro Ser Leu Gln Leu Ala Asp
145                 150                 155                 160

Glu Asp Ser Arg Leu Phe Ala Phe Tyr Asn Leu Leu His Cys His Arg
                165                 170                 175

Arg Asp Ser His Lys Ile Asp Asn Tyr Leu Lys Val Leu Lys Cys Arg
            180                 185                 190

Leu Ile His Asp Ser Asn Cys
        195

<210> SEQ ID NO 15
<211> LENGTH: 199
<212> TYPE: PRT
<213> ORGANISM: Meleagris gallopavo

<400> SEQUENCE: 15

Leu Pro Ile Cys Ser Ser Gly Ser Val Asn Cys Gly Val Ser Leu Gly
 1               5                  10                  15

Glu Leu Phe Asp Arg Ala Val Arg Leu Ser His Tyr Ile His Phe Leu
             20                  25                  30

Ser Ser Glu Ile Phe Asn Glu Phe Asp Glu Arg Tyr Ala Gln Gly Arg
         35                  40                  45

Gly Phe Ile Thr Lys Ala Val Asn Gly Cys His Thr Ser Ser Leu Thr
     50                  55                  60

Thr Pro Glu Asp Lys Glu Gln Thr Gln Gln Ile His His Glu Leu Leu
 65                  70                  75                  80

Leu Asn Leu Ile Leu Gly Val Leu Arg Ser Trp Asn Asp Pro Leu Ile
                 85                  90                  95

His Leu Ala Ser Glu Val Gln Arg Ile Lys Glu Ala Pro Asp Thr Ile
            100                 105                 110

```
Leu Trp Lys Ala Val Glu Ile Glu Glu Gln Asn Lys Arg Leu Leu Glu
        115                 120                 125

Gly Met Glu Lys Ile Val Gly Arg Ile His Ser Gly Asp Ala Gly Asn
        130                 135                 140

Glu Val Phe Ser Gln Trp Asp Gly Leu Pro Ser Leu Gln Leu Ala Asp
145                 150                 155                 160

Glu Asp Ser Arg Leu Phe Ala Phe Tyr Asn Leu Leu His Cys Leu Arg
                165                 170                 175

Arg Asp Ser His Lys Ile Asp Asn Tyr Leu Lys Val Leu Lys Cys Arg
                180                 185                 190

Leu Ile His Asp Asn Asn Cys
        195
```

```
<210> SEQ ID NO 16
<211> LENGTH: 198
<212> TYPE: PRT
<213> ORGANISM: Unknown Organism
<220> FEATURE:
<223> OTHER INFORMATION: Description of Unknown Organism: Undetermined
      genus/species of Sea turtle

<400> SEQUENCE: 16
```

```
Leu Pro Ile Cys Pro Ser Gly Ser Val Gly Cys Gln Val Ser Leu Glu
1               5                   10                  15

Asn Leu Phe Asp Arg Ala Val Lys Leu Ser His Tyr Ile His Ser Leu
                20                  25                  30

Ser Ser Glu Met Phe Asn Glu Phe Asp Glu Arg Tyr Ala Gln Gly Arg
            35                  40                  45

Gly Phe Leu Thr Lys Ala Ile Asn Gly Cys His Thr Ser Ser Leu Thr
        50                  55                  60

Thr Pro Glu Asp Lys Glu Gln Ala Gln Gln Ile His His Glu Asp Leu
65                  70                  75                  80

Leu Asn Leu Val Leu Gly Val Leu Arg Ser Trp Asn Asp Pro Leu Leu
                85                  90                  95

His Leu Val Ser Glu Val Gln Ser Ile Lys Glu Ala Pro Asp Thr Ile
                100                 105                 110

Leu Lys Ala Val Glu Ile Glu Glu Gln Asp Lys Arg Leu Leu Glu Gly
        115                 120                 125

Met Glu Lys Ile Val Gly Gln Val His Pro Gly Glu Ile Glu Asn Glu
        130                 135                 140

Val Tyr Ser Pro Trp Ser Gly Leu Pro Ser Leu Gln Gln Val Asp Glu
145                 150                 155                 160

Asp Ser Arg Leu Phe Ala Phe Tyr Asn Leu Leu His Cys Leu Arg Arg
                165                 170                 175

Asp Ser His Lys Ile Asp Asn Tyr Leu Lys Leu Leu Lys Cys Arg Leu
                180                 185                 190

Ile His Asp Asn Asp Cys
        195
```

```
<210> SEQ ID NO 17
<211> LENGTH: 199
<212> TYPE: PRT
<213> ORGANISM: Crocodylus sp.

<400> SEQUENCE: 17
```

```
Leu Pro Ile Cys Pro Ser Gly Ser Val Asn Cys Gln Val Ser Leu Gly
1               5                   10                  15
```

```
Glu Leu Phe Asp Arg Ala Val Lys Leu Ser His Tyr Ile His Phe Leu
             20                  25                  30

Ser Ser Glu Met Phe Asn Glu Phe Asp Glu Arg Tyr Ala Gln Gly Arg
         35                  40                  45

Gly Phe Ile Thr Lys Ala Val Asn Gly Cys His Thr Ala Ser Leu Thr
     50                  55                  60

Thr Pro Glu Asp Lys Glu Gln Ala Gln Gln Ile His His Glu Asp Leu
 65                  70                  75                  80

Leu Asn Leu Val Leu Gly Val Leu Arg Ser Trp Asn Asp Pro Leu Leu
                 85                  90                  95

His Leu Val Thr Glu Val Gln Arg Ile Lys Glu Ala Pro Asp Thr Ile
            100                 105                 110

Leu Trp Lys Ala Val Glu Ile Glu Glu Gln Asn Lys Arg Leu Leu Glu
        115                 120                 125

Gly Met Glu Lys Ile Ile Gly Arg Val Gln Pro Gly Asp Thr Gly Asn
    130                 135                 140

Glu Val Tyr Ser Arg Trp Ser Gly Leu Pro Ser Leu Gln Leu Ala Asp
145                 150                 155                 160

Glu Asp Ser Arg Leu Phe Ala Phe Tyr Asn Leu Leu His Cys Gly Arg
                165                 170                 175

Arg Asp Ser His Lys Ile Asp Asn Tyr Leu Lys Leu Leu Lys Cys Arg
            180                 185                 190

Leu Ile His Asp Ser Asn Cys
        195

<210> SEQ ID NO 18
<211> LENGTH: 199
<212> TYPE: PRT
<213> ORGANISM: Lacertus sp.

<400> SEQUENCE: 18

Leu Pro Ile Cys Pro Ser Gly Ser Val Asn Cys Gln Val Ser Leu Gly
 1               5                  10                  15

Glu Leu Phe Asp Arg Ala Val Lys Leu Ser His Tyr Ile His Phe Leu
             20                  25                  30

Ser Ser Glu Met Phe Asn Glu Phe Asp Glu Arg Tyr Ala Gln Gly Arg
         35                  40                  45

Gly Phe Ile Thr Lys Ala Val Asn Gly Cys His Thr Ala Ser Leu Thr
     50                  55                  60

Thr Pro Glu Asp Lys Glu Gln Ala Gln Gln Ile His His Glu Asp Leu
 65                  70                  75                  80

Leu Asn Leu Val Leu Gly Val Leu Arg Ser Trp Asn Asp Pro Leu Leu
                 85                  90                  95

His Leu Val Thr Glu Val Gln Arg Ile Lys Glu Ala Pro Asp Thr Ile
            100                 105                 110

Leu Trp Lys Ala Val Glu Ile Glu Glu Gln Asn Lys Arg Leu Leu Glu
        115                 120                 125

Gly Met Glu Lys Val Ile Gly Arg Val Gln Pro Gly Asp Thr Gly Asn
    130                 135                 140

Glu Val Tyr Ser Arg Trp Ser Gly Leu Pro Ser Leu Gln Leu Ala Asp
145                 150                 155                 160

Glu Asp Ser Arg Leu Phe Ala Phe Tyr Asn Leu Leu His Cys Gly Arg
                165                 170                 175

Arg Asp Ser His Lys Ile Asp Asn Tyr Leu Lys Leu Leu Lys Cys Arg
```

```
            180                 185                 190
Leu Ile His Asp Ser Asn Cys
        195

<210> SEQ ID NO 19
<211> LENGTH: 199
<212> TYPE: PRT
<213> ORGANISM: Unknown Organism
<220> FEATURE:
<223> OTHER INFORMATION: Description of Unknown Organism: Ancestral
      amniote
<220> FEATURE:
<221> NAME/KEY: MOD_RES
<222> LOCATION: (31)
<223> OTHER INFORMATION: Variable amino acid
<220> FEATURE:
<221> NAME/KEY: MOD_RES
<222> LOCATION: (158)
<223> OTHER INFORMATION: Variable amino acid

<400> SEQUENCE: 19

Leu Pro Ile Cys Pro Ser Gly Ala Val Asn Cys Gln Val Ser Leu Arg
  1               5                  10                  15

Asp Leu Phe Asp Arg Ala Val Lys Leu Ser His Tyr Ile His Xaa Leu
             20                  25                  30

Ser Ser Glu Met Phe Asn Glu Phe Asp Lys Arg Tyr Ala Gln Gly Arg
         35                  40                  45

Gly Phe Ile Thr Lys Ala Ile Asn Ser Cys His Thr Ser Ser Leu Thr
     50                  55                  60

Thr Pro Glu Asp Lys Glu Gln Ala Gln Gln Ile His His Glu Val Leu
 65                  70                  75                  80

Leu Asn Leu Ile Leu Gly Val Leu Arg Ser Trp Asn Asp Pro Leu Leu
                 85                  90                  95

His Leu Val Thr Glu Val Arg Gly Met Lys Glu Ala Pro Asp Ala Ile
            100                 105                 110

Leu Ser Lys Ala Ile Glu Ile Glu Glu Gln Asn Lys Arg Leu Leu Glu
        115                 120                 125

Gly Met Glu Lys Ile Val Gly Gln Val His Pro Gly Ala Lys Glu Asn
    130                 135                 140

Glu Val Tyr Ser Val Trp Ser Gly Leu Pro Ser Leu Gln Xaa Ala Asp
145                 150                 155                 160

Glu Asp Ser Arg Leu Phe Ala Phe Tyr Asn Leu Leu His Cys Leu Arg
                165                 170                 175

Arg Asp Ser His Lys Ile Asp Asn Tyr Leu Lys Leu Leu Lys Cys Arg
            180                 185                 190

Ile Ile His Asn Asn Cys
        195

<210> SEQ ID NO 20
<211> LENGTH: 199
<212> TYPE: PRT
<213> ORGANISM: Xenopus sp.

<400> SEQUENCE: 20

Leu Pro Ile Cys Pro Asp Gly Gly Thr Asn Cys Gln Met Ser Thr Gly
  1               5                  10                  15

Ala Leu Phe Asp Lys Ala Val Lys Leu Ser His Tyr Ile His Ser Leu
             20                  25                  30

Ser Ser Glu Met Phe Asn Glu Phe Asp Glu Arg Phe Thr Pro Ser Arg
         35                  40                  45
```

```
Arg Phe Leu Ala Lys Ser Ile Met Ser Cys His Thr Ser Ser Leu Asn
         50                  55                  60

Thr Pro Glu Asp Arg Glu Gln Ala Gln Gln Ile Gln His Glu Asp Leu
 65                  70                  75                  80

Leu Asn Leu Val Met Arg Val Leu Lys Ser Trp Asn Asp Pro Leu Leu
                 85                  90                  95

His Met Val Gly Glu Val Gln Asp Ile Arg Glu Ala Pro Asp Thr Ile
                100                 105                 110

Leu Trp Lys Thr Val Glu Val Glu Gln Thr Lys Arg Leu Leu Glu
                115                 120                 125

Gly Met Glu Lys Ile Val Gly Arg Ile His Pro Phe Asp Leu Glu Asn
130                 135                 140

Asp Val Asn Ser Leu Trp Ser Gly Pro Pro Ala Ala Gln Ser Ala Asp
145                 150                 155                 160

Glu Asn Ser Arg Leu Phe Gly Phe Tyr Asn Leu Leu His Cys Leu Arg
                165                 170                 175

Arg Asp Ser His Leu Ile Asp Asn Tyr Leu Lys Leu Lys Cys Ala
                180                 185                 190

Leu Ile His Asp Ser Asn Cys
195

<210> SEQ ID NO 21
<211> LENGTH: 198
<212> TYPE: PRT
<213> ORGANISM: Rana catesbeiana

<400> SEQUENCE: 21

Gln Pro Ile Cys Pro Asn Gly Gly Thr Asn Cys Gln Ile Pro Thr Ser
 1               5                  10                  15

Ala Leu Phe Asp Arg Ala Val Lys Leu Ser His Tyr Ile His Ser Leu
                 20                  25                  30

Ser Ser Glu Met Phe Asn Glu Phe Asp Glu Arg Phe Thr Pro Gly Arg
             35                  40                  45

Arg Phe Leu Ala Lys Ser Gly Ile Ser Cys His Thr Ser Ser Leu Asn
         50                  55                  60

Thr Pro Glu Asp Lys Glu Gln Ala Arg Gln Ile Gln His Glu Asp Leu
 65                  70                  75                  80

Leu Asn Leu Val Leu Lys Val Leu Arg Ser Trp Asn Asp Pro Leu Val
                 85                  90                  95

His Met Val Ser Glu Val Gln Asp Ile Arg Glu Ala Pro Asp Thr Ile
                100                 105                 110

Leu Trp Lys Thr Val Glu Val Glu Gln Thr Lys Arg Leu Leu Glu
                115                 120                 125

Gly Met Glu Arg Ile Ile Gly Arg Ile Gln Pro Gly Asp Leu Glu Asn
130                 135                 140

Glu Ile Tyr Ser Pro Trp Pro Gly Pro Ala Ser Ile Pro Gly Asp Glu
145                 150                 155                 160

Asn Ser Arg Leu Phe Ala Phe Tyr Asn Leu Leu His Cys Leu Arg Arg
                165                 170                 175

Asp Ser His Lys Ile Asp Asn Tyr Leu Lys Leu Leu Lys Cys Arg Leu
                180                 185                 190

Ile His Glu Gly Asn Cys
195
```

```
<210> SEQ ID NO 22
<211> LENGTH: 199
<212> TYPE: PRT
<213> ORGANISM: Dipneusti sp.

<400> SEQUENCE: 22

Leu Pro Ile Cys Ala Asn Gly Ser Thr Asn Cys His Ala Ile Pro Leu
 1               5                  10                  15

Asp Asp Leu Phe Glu Phe Val Val Lys Leu Ala His Arg Ile His Ser
            20                  25                  30

Leu Thr Ser Asp Met Phe Asn Glu Phe Asp Glu Arg Tyr Ala Gln Gly
        35                  40                  45

Arg Gly Phe Ile Ser Arg Ala Ile Asn Asn Cys His Thr Ser Ser Leu
    50                  55                  60

Thr Thr Pro Glu Ala Lys Glu Asn Ala Gln Lys Phe His His Asp Asp
65                  70                  75                  80

Leu Leu Arg Leu Val Met Lys Val Leu Arg Ser Trp Asn Asp Pro Leu
                85                  90                  95

Leu Gln Leu Val Ser Glu Val Gln Gly Ile Gly Glu Ala Pro Gly Thr
            100                 105                 110

Ile Leu Trp Lys Val Thr Glu Val Glu Asp Gln Thr Lys Gln Leu Ile
        115                 120                 125

Glu Gly Met Glu Lys Ile Leu Ser Ala Met His Pro Asn Gly Leu Asp
    130                 135                 140

Asn Glu Val Leu Ser Leu Trp Pro Met Pro Gly Ala Met His Ala Gly
145                 150                 155                 160

Asp Gly Ser Lys Leu Phe Ala Leu Tyr Asn Leu Leu His Cys Phe Arg
                165                 170                 175

Arg Asp Ser Phe Lys Ile Asp Ser Tyr Leu Lys Leu Leu Arg Cys Ala
            180                 185                 190

Leu Phe His Glu Gly Gly Cys
        195

<210> SEQ ID NO 23
<211> LENGTH: 188
<212> TYPE: PRT
<213> ORGANISM: Oreochromis aureus

<400> SEQUENCE: 23

Val Pro Ile Asn Glu Leu Leu Glu Arg Ala Ser Gln His Ser Asp Lys
 1               5                  10                  15

Leu His Ser Leu Ser Thr Thr Leu Thr Gln Glu Leu Asp Ser His Phe
            20                  25                  30

Pro Pro Ile Gly Arg Val Ile Met Pro Arg Pro Ala Met Cys His Thr
        35                  40                  45

Ser Ser Leu Gln Thr Pro Ile Asp Lys Asp Gln Ala Leu Gln Val Ser
    50                  55                  60

Glu Ser Asp Leu Met Ser Leu Ala Arg Ser Leu Leu Gln Ala Trp Ser
65                  70                  75                  80

Asp Pro Leu Val Val Leu Ser Ser Ala Ser Thr Leu Pro His Pro
                85                  90                  95

Ala Gln Ser Ser Ile Phe Asn Lys Ile Gln Glu Met Gln Gln Tyr Ser
            100                 105                 110

Lys Ser Leu Lys Asp Gly Leu Asp Val Leu Ser Ser Lys Met Gly Ser
        115                 120                 125

Pro Ala Gln Ala Ile Thr Ser Leu Pro Tyr Arg Gly Gly Thr Asn Leu
```

```
            130                 135                 140
Gly His Asp Lys Ile Thr Lys Leu Ile Asn Phe Asn Phe Leu Leu Ser
145                 150                 155                 160

Cys Leu Arg Arg Asp Ser His Lys Ile Asp Ser Phe Leu Lys Val Leu
                165                 170                 175

Arg Cys Arg Ala Ala Lys Met Gln Pro Glu Met Cys
            180                 185

<210> SEQ ID NO 24
<211> LENGTH: 177
<212> TYPE: PRT
<213> ORGANISM: Oreochromis aureus

<400> SEQUENCE: 24

Val Pro Ile Asn Asp Leu Ile Tyr Arg Ala Ser Gln Gln Ser Asp Lys
  1               5                  10                  15

Leu His Ala Leu Ser Thr Met Leu Thr Gln Glu Leu Gly Ser Glu Ala
                 20                  25                  30

Phe Pro Ile Asp Arg Val Leu Ala Cys His Thr Ser Ser Leu Gln Thr
             35                  40                  45

Pro Thr Asp Lys Glu Gln Ala Leu Gln Val Ser Glu Ser Asp Leu Leu
         50                  55                  60

Ser Leu Ala Arg Ser Leu Leu Gln Ala Trp Ser Asp Pro Leu Glu Val
 65                  70                  75                  80

Leu Ser Ser Ser Thr Asn Val Leu Pro Tyr Ser Ala Gln Ser Thr Leu
                 85                  90                  95

Ser Lys Thr Ile Gln Lys Met Gln Glu His Ser Lys Asp Leu Lys Asp
                100                 105                 110

Gly Leu Asp Ile Leu Ser Ser Lys Met Gly Pro Ala Ala Gln Thr Ile
            115                 120                 125

Thr Ser Leu Pro Phe Ile Glu Thr Asn Glu Ile Gly Gln Asp Lys Ile
        130                 135                 140

Thr Lys Leu Leu Ser Cys Phe Arg Arg Asp Ser His Lys Ile Asp Ser
145                 150                 155                 160

Phe Leu Lys Val Leu Arg Cys Arg Ala Ala Asn Met Gln Pro Gln Val
                165                 170                 175

Cys

SEQ ID NO 25
<211> LENGTH: 187
<212> TYPE: PRT
<213> ORGANISM: Cyprinus carpio

<400> SEQUENCE: 25

Val Gly Leu Asn Asp Leu Leu Glu Arg Ala Ser Glu Leu Ser Asp Lys
  1               5                  10                  15

Leu His Ser Leu Ser Thr Ser Leu Thr Asn Asp Leu Asp Ser His Phe
                 20                  25                  30

Pro Pro Val Gly Arg Val Met Met Pro Arg Pro Ser Met Cys His Thr
             35                  40                  45

Ser Ser Leu Gln Val Pro Asn Asp Lys Asp Gln Ala Leu Lys Val Pro
         50                  55                  60

Glu Asp Pro Leu Leu Ser Leu Ala Arg Ser Leu Leu Leu Ala Trp Ser
 65                  70                  75                  80

Asp Pro Leu Ala Leu Leu Ser Ser Glu Ala Ser Ser Leu Ala His Pro
                 85                  90                  95
```

```
Glu Arg Asn Thr Ile Asp Ser Lys Thr Lys Glu Leu Gln Glu Asn Ile
            100                 105                 110

Asn Ser Leu Gly Ala Gly Leu Glu His Val Phe Asn Lys Met Asp Ser
        115                 120                 125

Thr Ser Asp Asn Leu Ser Ser Leu Pro Phe Tyr Thr Asn Ser Leu Gly
    130                 135                 140

Glu Asp Lys Thr Ser Arg Leu Val Asn Phe His Phe Leu Leu Ser Cys
145                 150                 155                 160

Phe Arg Arg Asp Ser His Lys Ile Asp Ser Phe Leu Lys Val Leu Arg
                165                 170                 175

Cys Arg Ala Ala Lys Lys Arg Pro Glu Met Cys
            180                 185

<210> SEQ ID NO 26
<211> LENGTH: 187
<212> TYPE: PRT
<213> ORGANISM: Hypophthalmichthys nobilis

<400> SEQUENCE: 26

Val Gly Leu Asn Asp Leu Leu Glu Arg Ala Ser Gln Leu Ser Asp Lys
1               5                   10                  15

Leu His Ser Leu Ser Thr Ser Leu Thr Asn Asp Leu Asp Ser His Phe
            20                  25                  30

Pro Pro Val Gly Arg Val Met Met Pro Arg Pro Ser Met Cys His Ile
        35                  40                  45

Ser Ser Leu Gln Ile Pro Asn Asp Lys Asp Gln Ala Leu Lys Val Pro
    50                  55                  60

Glu Asp Glu Leu Leu Ser Leu Ala Arg Ser Leu Leu Leu Ala Trp Ser
65                  70                  75                  80

Asp Pro Leu Ala Leu Leu Ser Ser Glu Ala Ser Ser Leu Ala His Pro
                85                  90                  95

Glu Arg Asn Thr Ile Asn Ser Lys Thr Lys Glu Leu Gln Asp Asn Ile
            100                 105                 110

Asn Ser Leu Gly Ala Gly Leu Glu Arg Val Val His Lys Met Gly Ser
        115                 120                 125

Ser Ser Asp Asn Leu Ser Ser Leu Pro Phe Tyr Ser Asn Ser Leu Gly
    130                 135                 140

Gln Asp Lys Thr Ser Arg Leu Val Asn Phe His Phe Leu Leu Ser Cys
145                 150                 155                 160

Phe Arg Arg Asp Ser His Lys Ile Asp Ser Phe Leu Lys Val Leu Arg
                165                 170                 175

Cys Arg Ala Ala Lys Lys Arg Pro Glu Met Cys
            180                 185

<210> SEQ ID NO 27
<211> LENGTH: 187
<212> TYPE: PRT
<213> ORGANISM: Hypophthalmichthys molitrix

<400> SEQUENCE: 27

Val Gly Leu Asn Asp Leu Leu Glu Arg Ala Ser Gln Leu Ser Asp Lys
1               5                   10                  15

Leu His Ser Leu Ser Thr Ser Leu Thr Asn Asp Leu Asp Ser His Phe
            20                  25                  30

Pro Pro Val Gly Arg Val Met Met Pro Arg Pro Ser Met Cys His Thr
        35                  40                  45
```

```
Ser Ser Leu Gln Ile Pro Asn Asp Lys Asp Gln Ala Leu Lys Val Pro
     50                  55                  60

Glu Asp Glu Leu Leu Ser Leu Ala Arg Ser Leu Leu Leu Ala Trp Ser
 65                  70                  75                  80

Asp Pro Leu Ala Leu Leu Ser Ser Lys Ala Ser Ser Leu Ala His Pro
                 85                  90                  95

Glu Arg Asn Thr Ile Asn Ser Lys Thr Lys Glu Leu Gln Asp Asn Ile
            100                 105                 110

Asn Ser Leu Val Pro Gly Leu Glu His Val Val His Lys Met Gly Ser
        115                 120                 125

Ser Ser Asp Asn Leu Ser Ser Leu Pro Phe Tyr Ser Asn Ser Leu Gly
    130                 135                 140

Gln Asp Lys Thr Ser Arg Leu Val Asn Phe His Phe Leu Leu Ser Cys
145                 150                 155                 160

Phe Arg Arg Asp Ser His Lys Ile Asp Ser Phe Leu Lys Val Leu Arg
                165                 170                 175

Cys Arg Ala Ala Lys Lys Arg Pro Glu Met Cys
            180                 185
```

<210> SEQ ID NO 28
<211> LENGTH: 187
<212> TYPE: PRT
<213> ORGANISM: Oncorhynchus keta

<400> SEQUENCE: 28

```
Ile Gly Leu Ser Asp Leu Met Glu Arg Ala Ser Gln Arg Ser Asp Lys
  1               5                  10                  15

Leu His Ser Leu Ser Thr Ser Leu Thr Lys Asp Leu Asp Ser His Phe
             20                  25                  30

Pro Pro Met Gly Arg Val Met Met Pro Arg Pro Ser Met Cys His Thr
         35                  40                  45

Ser Ser Leu Gln Thr Pro Lys Asp Lys Glu Gln Ala Leu Lys Val Ser
     50                  55                  60

Glu Asn Glu Leu Ile Ser Leu Ala Arg Ser Leu Leu Leu Ala Trp Asn
 65                  70                  75                  80

Asp Pro Leu Leu Leu Leu Ser Ser Glu Ala Pro Thr Cys Pro His Pro
                 85                  90                  95

Ser Asn Gly Asp Ile Ser Ser Lys Ile Arg Glu Leu Gln Asp Tyr Ser
            100                 105                 110

Lys Ser Leu Gly Asp Gly Leu Asp Ile Met Val Asn Lys Met Gly Pro
        115                 120                 125

Ser Ser Gln Tyr Ile Ser Ile Pro Phe Lys Gly Gly Asp Leu Gly
    130                 135                 140

Asn Asp Lys Thr Ser Arg Leu Ile Asn Phe His Phe Leu Met Ser Cys
145                 150                 155                 160

Phe Arg Arg Asp Ser His Lys Ile Asp Ser Phe Leu Lys Val Leu Arg
                165                 170                 175

Cys Arg Ala Thr Lys Met Arg Pro Glu Thr Cys
            180                 185
```

<210> SEQ ID NO 29
<211> LENGTH: 189
<212> TYPE: PRT
<213> ORGANISM: Oncorhynchus tshawytscha

<400> SEQUENCE: 29

```
Ile Gly Leu Ser Asp Leu Met Glu Arg Ala Ser Gln Arg Ser Asp Lys
  1               5                  10                  15

Leu His Ser Leu Ser Thr Ser Leu Thr Lys Asp Leu Asp Ser His Phe
             20                  25                  30

Pro Pro Met Gly Arg Val Met Met Pro Arg Pro Ser Met Cys His Thr
             35                  40                  45

Ser Ser Leu Gln Thr Pro Lys Asp Lys Glu Gln Ala Leu Lys Val Ser
         50                  55                  60

Glu Asn Glu Leu Ile Ser Leu Ala Arg Tyr Leu Leu Leu Ala Trp Asn
 65                  70                  75                  80

Asp Pro Leu Leu Leu Ser Ser Glu Ala Pro Thr Leu Pro His Thr
                 85                  90                  95

Pro Ser Asn Gly Asp Ile Ser Ser Lys Ile Arg Glu Leu Gln Asp Tyr
             100                 105                 110

Ser Lys Ser Leu Gly Asp Gly Leu Asp Ile Met Val Asn Lys Met Gly
             115                 120                 125

Pro Ser Ser Gln Tyr Ile Ser Ser Ile Pro Phe Lys Gly Gly Asp Leu
         130                 135                 140

Gly Asn Asp Lys Thr Ser Pro Arg Leu Ile Asn Phe His Phe Leu Met
145                 150                 155                 160

Ser Cys Phe Arg Arg Asp Ser His Lys Ile Asp Ser Phe Leu Lys Val
                 165                 170                 175

Leu Arg Cys Arg Ala Thr Asn Met Arg Pro Glu Thr Cys
                 180                 185
```

<210> SEQ ID NO 30
<211> LENGTH: 187
<212> TYPE: PRT
<213> ORGANISM: Tructa sp.

<400> SEQUENCE: 30

```
Ile Gly Leu Ser Asp Leu Met Glu Arg Ala Ser Gln Arg Ser Asp Lys
  1               5                  10                  15

Leu His Ser Leu Ser Thr Ser Leu Thr Lys Asp Leu Asp Ser His Phe
             20                  25                  30

Pro Pro Met Gly Arg Val Met Met Pro Arg Pro Ser Met Cys His Thr
             35                  40                  45

Ser Ser Leu Gln Thr Pro Lys Asp Lys Glu Gly Ala Leu Lys Val Ser
         50                  55                  60

Glu Asn Glu Leu Ile Ser Leu Ala Arg Ser Leu Leu Leu Ala Trp Asn
 65                  70                  75                  80

Asp Pro Leu Leu Leu Ser Ser Glu Ala Pro Thr Leu Pro His Pro
                 85                  90                  95

Ser Asn Gly Asp Ile Ser Ser Lys Ile Arg Glu Leu Gln Asp Tyr Ser
             100                 105                 110

Lys Ser Leu Gly Asp Gly Leu Asp Ile Met Val Asn Lys Met Gly Pro
             115                 120                 125

Ser Ser Gln Tyr Ile Ser Ser Ile Pro Phe Lys Gly Gly Asp Leu Gly
         130                 135                 140

Asn Asp Lys Thr Ser Arg Leu Ile Asn Phe His Phe Leu Met Ser Cys
145                 150                 155                 160

Phe Arg Arg Asp Ser His Lys Ile Asp Ser Phe Leu Lys Val Leu Arg
                 165                 170                 175

Cys Arg Ala Thr Lys Met Arg Pro Glu Ala Cys
```

```
                    180                 185

<210> SEQ ID NO 31
<211> LENGTH: 187
<212> TYPE: PRT
<213> ORGANISM: Unknown Organism
<220> FEATURE:
<223> OTHER INFORMATION: Description of Unknown Organism: Ancestral
      boney fish
<220> FEATURE:
<221> NAME/KEY: MOD_RES
<222> LOCATION: (186)
<223> OTHER INFORMATION: Variable amino acid

<400> SEQUENCE: 31

Ile Gly Leu Ser Asp Leu Met Glu Arg Ala Ser Gln Arg Ser Asp Lys
 1               5                  10                  15

Leu His Ser Leu Ser Thr Ser Leu Thr Lys Asp Leu Asp Ser His Phe
            20                  25                  30

Pro Pro Met Gly Arg Val Met Met Pro Arg Pro Ser Met Cys His Thr
        35                  40                  45

Ser Ser Leu Gln Thr Pro Lys Asp Lys Glu Gln Ala Leu Lys Val Ser
    50                  55                  60

Glu Asn Glu Leu Ile Ser Leu Ala Arg Ser Leu Leu Leu Ala Trp Asn
65                  70                  75                  80

Asp Pro Leu Leu Leu Leu Ser Ser Glu Ala Pro Thr Leu Pro His Pro
                85                  90                  95

Ser Asn Gly Asp Ile Ser Ser Lys Ile Arg Glu Leu Gln Asp Tyr Ser
            100                 105                 110

Lys Ser Leu Gly Asp Gly Leu Asp Ile Met Val Asn Lys Met Gly Pro
        115                 120                 125

Ser Ser Gln Tyr Ile Ser Ser Ile Pro Phe Lys Gly Gly Asp Leu Gly
    130                 135                 140

Asn Asp Lys Thr Ser Arg Leu Ile Asn Phe His Phe Leu Met Ser Cys
145                 150                 155                 160

Phe Arg Arg Asp Ser His Lys Ile Asp Ser Phe Leu Lys Val Leu Arg
                165                 170                 175

Cys Arg Ala Thr Lys Met Arg Pro Glu Xaa Cys
            180                 185

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: 6X His tag

<400> SEQUENCE: 32

His His His His His His
 1               5

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 33
gcttagcagt tgttgttgtg                                             20
```

```
<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 34
atgaacatca aaggat                                                     16

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cggctcctag agaggatgga gct                                             23

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 36
gcacttcagt atccatggtc tggt                                            24

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 37
agaaggcagc caacatgaag                                                 20

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cttctagagc gcatggagct cata                                            24

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ccctctagac tcgagcggcc gcc                                             23
```